(12) United States Patent
Bannantine et al.

(10) Patent No.: US 11,981,750 B2
(45) Date of Patent: May 14, 2024

(54) **ANTIGENIC TRIPEPTIDES DERIVED FROM *MYCOBACTERIUM AVIUM* SUBSP. *PARATUBERCULOSIS* S-TYPE STRAINS, DERIVATIVES AND USES THEREOF**

(71) Applicants: INSTITUT PASTEUR, Paris (FR); INSTITUT NATIONAL DE RECHERCHE POUR L'AGRICULTURE L'ALIMENTATION ET L'ENVIRONNEMENT, Paris (FR); THE UNITED STATES OF AMERICA, AS REPRESENTED BY THE SECRETARY OF AGRICULTURE, Washington, DC (US)

(72) Inventors: John P. Bannantine, Ames, IA (US); Gilles Etienne, Toulouse (FR); Sylvie Bay, Paris (FR); Franck Biet, Notre Dame D'Oe (FR)

(73) Assignees: INSTITUT PASTEUR, Paris (FR); INSTITUT NATIONAL DE RECHERCHE POUR L'AGRICULTURE L'ALIMENTATION ET L'ENVIRONNEMENT, Paris (FR); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 1 day.

(21) Appl. No.: 17/938,865

(22) Filed: Oct. 7, 2022

(65) Prior Publication Data

US 2023/0046953 A1 Feb. 16, 2023

Related U.S. Application Data

(62) Division of application No. 16/470,962, filed as application No. PCT/EP2017/083924 on Dec. 20, 2017, now Pat. No. 11,498,942.

(30) Foreign Application Priority Data

Dec. 20, 2016 (WO) ................. PCT/IB2016/002018

(51) Int. Cl.
| | |
|---|---|
| *C07K 5/087* | (2006.01) |
| *A61K 39/04* | (2006.01) |
| *A61K 47/54* | (2017.01) |
| *A61K 47/60* | (2017.01) |
| *C07K 7/06* | (2006.01) |
| *C12Q 1/689* | (2018.01) |
| *G01N 33/569* | (2006.01) |

(52) U.S. Cl.
CPC ............ *C07K 5/0812* (2013.01); *A61K 39/04* (2013.01); *A61K 47/542* (2017.08); *A61K 47/60* (2017.08); *C07K 7/06* (2013.01); *C12Q 1/689* (2013.01); *G01N 33/5695* (2013.01); *G01N 2333/5428* (2013.01); *G01N 2333/57* (2013.01); *G01N 2469/20* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 5,750,767 A | 5/1998 | Carpino et al. | |
| 8,883,173 B2 | 11/2014 | Reyrat et al. | |

FOREIGN PATENT DOCUMENTS

| | | |
|---|---|---|
| WO | 03/104493 A1 | 12/2003 |
| WO | 2009/053844 A1 | 4/2009 |

OTHER PUBLICATIONS

Wen-Ren Li et al, (2000) Synlett, pp. 1608-1612.
Cunningham B R et al, (1997) Bioorganic & Medicinal Chemistry Letters, Pergamon, Amsterdam, pp. 19-24.
Balraju V et al, (2006), Tetrahedron Letters, Elsevier, Amsterdam, pp. 3569-3571.
Pawar Sachin A et al, (2012), European Journal of Medicinal Chemistry, Editions Scientifique Elsevier, Paris, pp. 144-154.
Erapalapati V. et al, (2006) Journal of Polymer Science, Part A : Polymer Chemistry pp. 2501-2509.
Garner P et al., (2006) Tetrahedron Letters, Elsevier, Amsterdam, pp. 483-486.
Oka T et al, (1973) Archives of Biochemistry and Biophysics, Academic Press, pp. 543-551.
Mullican M D et al, (1994), Bioorganic & Medicinal Chemistry Letters, Pergamon, Amsterdam, pp. 2359-2364.

(Continued)

Primary Examiner — Brian Gangle
(74) Attorney, Agent, or Firm — Arrigo, Lee, Guttman & Mouta-Bellum LLP

(57) ABSTRACT

The present invention is directed to an isolated synthetic tripeptide of formula H-D-Phe-N-Methyl-L-Val-L-Ala-OMe (SEQ ID NO:1), or a derivative thereof, and to the corresponding lipotripeptides, which are specific to *Mycobacterium avium* subsp. *paratuberculosis* (Map) S-type strain, as well as derivatives and conjugates thereof. The invention also concerns the use of these antigens in different methods and tests for detecting Map infection, especially by detecting humoral response and cell mediated response of infected animals. The invention is also directed to a genetic signature of Map and a mass spectrometry and NMR spectroscopy signature of Map presence or infection.

14 Claims, 17 Drawing Sheets

Figure 2A:
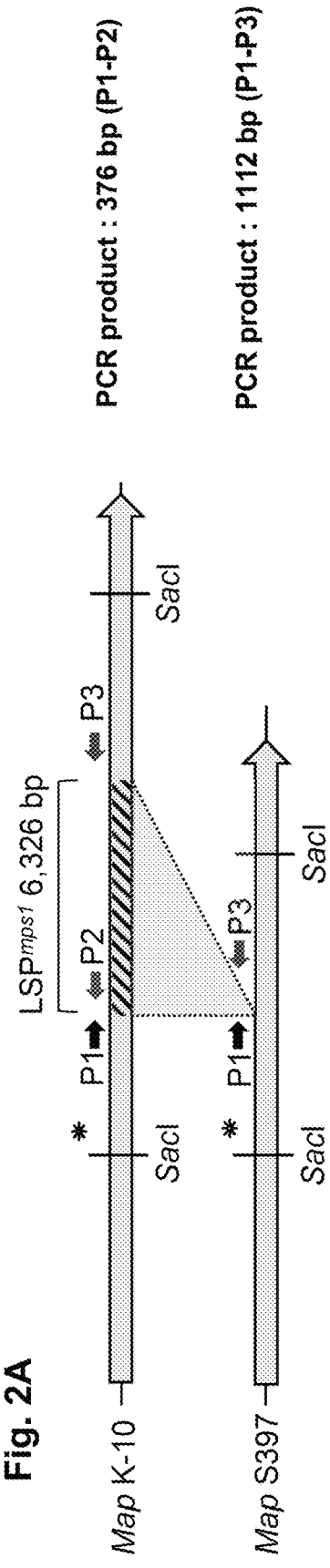

Specification includes a Sequence Listing.

(56) References Cited

OTHER PUBLICATIONS

Sorg G et al, (2005), Journal of Peptide Scie, John Wiley and Sons Ltd, pp. 142-152.
Gratias R et al, (1998), Journal of the American Chemical Society, pp. 4763-4770.
K. Dohmann et al, (2003), Journal of Clinical Microbiology (2003), pp. 5215-5223.
Thibault, V.C. et al, (2008). J. Clin. Microbiol. 46: 4091-4094.
Marsh, I.B., et al (2006). J. Bacteriol. 188: 2290-2293.
Wang, H. et al, (2014). Proc. Natl. Acad. Sci. U. S. A. 111: 9259-9264.
Biet, F. et al, (2008). Vaccine 26: 257-268.
Li, L., et al (2005). Proc. Natl. Acad. Sci. U. S. A. 102: 12344-12349.
Eckstein, T.M., S. et al, (2006). J. Biol. Chem. 281: 5209-5215.
Bannantine, J.P. et al, (2012). BMC Genomics 13: 89.
Semret, M. et al, (2006). J. Clin. Microbiol. 44: 881-887.
Holbert, S., M. et al, (2015). Res. Vet. Sci. 102: 118-121.
Nahms, (2008) Johne's disease on U.S. dairies, 1991-2007. USDA-APHIS-VS-CEAH Fort Collins, CO. Center for Epidemiology and Animal Health: 1-4.
Riviere, M. et al, (1996). Eur. J. Biochem. 241: 682-690.
Rottig, M., et al, (2011). Nucleic Acids Res. 39: W362-367.
Dukkipati V. et al, Vet. Microbiol. Nov. 15, 2016;195:136-143.
International Search Report and Written Opinion for PCT Application No. PCT/EP2017/083924, dated Jun. 8, 2018, which is related to this subject application.

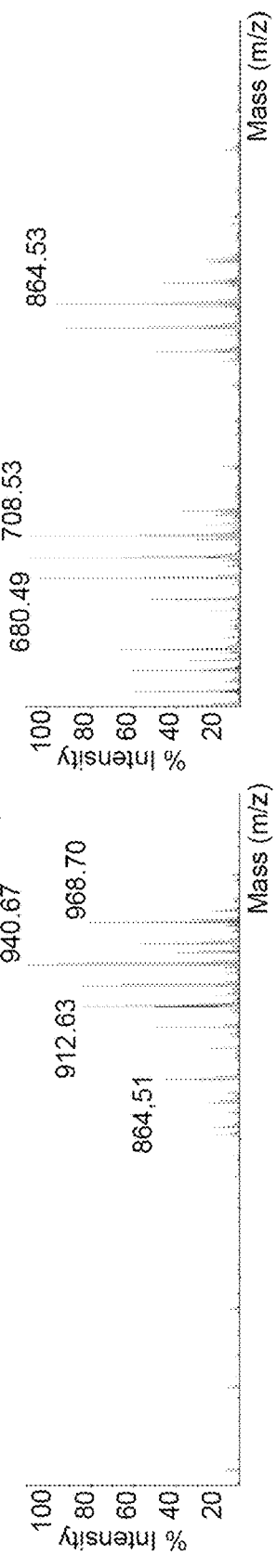

Fig. 4A
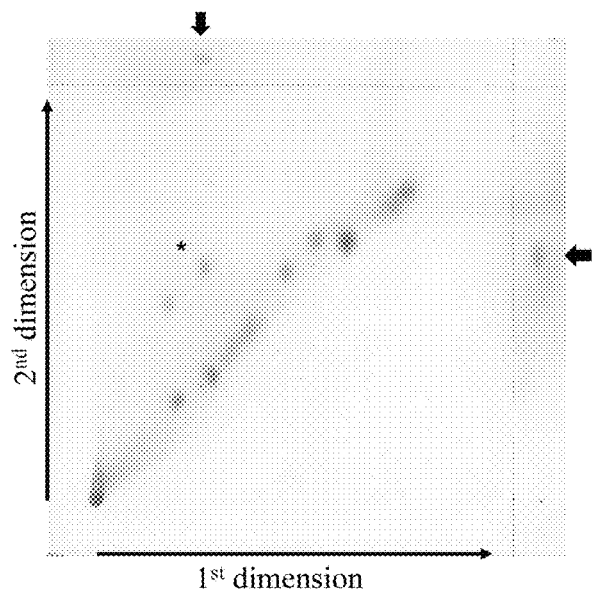
1st dimension
Fig. 4B
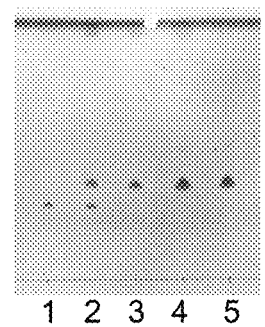
1 2 3 4 5
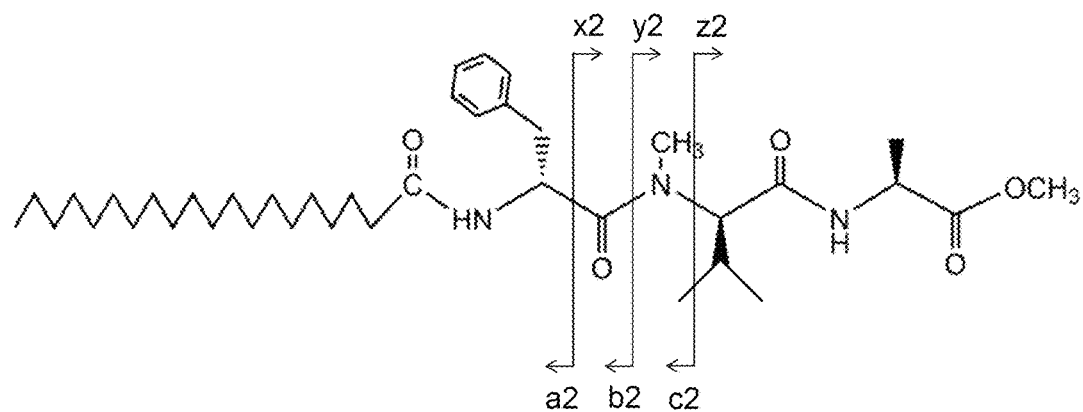
FIG.5

```
MapK10   1 MKRGDRAYPVTRGQLDIWLAEQTGHLDVAWQLGVLVRIDGAIDPALLHQTMRHVVGEAES  60
           +KRGDRAYPVTRGQLDIWLAEQTGHLDVAWQLGVLVRIDGAIDPALLHQTMRHVVGEAES
S397     1 VKRGDRAYPVTRGQLDIWLAEQTGHLDVAWQLGVLVRIDGAIDPALLHQTMRHVVGEAES  60

MapK10  61 LRASFFEADGQVFQKAVEYSDVDLTFYDLSGSSDPEREVREMTASIQRTPMPLTGPMIKF 120
           LRASFFEADGQVFQKAVEYSDVDLTFYDLSGSSDPEREVREMTASIQRTPMPLTGPM KF
S397    61 LRASFFEADGQVFQKAVEYSDVDLTFYDLSGSSDPEREVREMTASIQRTPMPLTGPMTKF 120

MapK10 121 ALFRTGSAEYYWFTTCHHIAIDGMGIALVGRRIAAVYTALASGKPIPPAFFGSLQDLVGG 180
           ALFRTGSAEYYWFTTCHHIAIDGMGIALVGRRIAAVYTALASGKPIPPAFFGSLQDLVGG
S397   121 ALFRTGSAEYYWFTTCHHIAIDGMGIALVGRRIAAVYTALASGKPIPPAFFGSLQDLVGG 180

MapK10 181 ELEYEASAKFLEDKDYWLAHRPGDGTAGHPPRPADDGRDPYSPSPPVQLDESVIGSVKEL 240
           ELEYEASAKFLEDKDYWLAHRPGDGTAGHPPRPADDGRDPYSPSPPVQLDESVIGSVKEL
S397   181 ELEYEASAKFLEDKDYWLAHRPGDGTAGHPPRPADDGRDPYSPSPPVQLDESVIGSVKEL 240

MapK10 241 SKALGIRRSSVLTAACALLVRGWCADGSDEVVLDFPVSRRVDPKSKTHPGMLAGVVPLVL 300
           SKALGIRRSSVLTAACALLVRGWCADGSDEVVLDFPVSRRVDPKSKTHPGMLAGVVPLVL
S397   241 SKALGIRRSSVLTAACALLVRGWCADGSDEVVLDFPVSRRVDPKSKTHPGMLAGVVPLVL 300

MapK10 301 HAPAAATFADFCRHVDQRSREALRHQQFPTRTLDGEGDFSGPRQAPNRVVVNFVPARLTL 360
           HAPAAATFADFCRHVDQRSREALRHQQFPTRTLDGEGDFSGPRQAPNRVVVNFVPARLTL
S397   301 HAPAAATFADFCRHVDQRSREALRHQQFPTRTLDGEGDFSGPRQAPNRVVVNFVPARLTL 360

MapK10 361 SLADVPATATYTSFGPVGHFGLFFLGFGDQQFLSTVGTGQPLANFDATDLAERLQRILAA 420
           SLADVPATATYTSFGPVGHFGLFFLGFGDQQFLSTVGTGQPLANFDATDLAERLQRILAA
S397   361 SLADVPATATYTSFGPVGHFGLFFLGFGDQQFLSTVGTGQPLANFDATDLAERLQRILAA 420

MapK10 421 MAADPARLLSSLDVLRDPEHAQLEALGNTAVLTRTPGPAVSVPELFATQVARAPQDVALV 480
           MAADPARLLSSLDVLRDPEHAQLEALGNTAVLTRTPGPAVSVPELFATQVARAPQDVALV
S397   421 MAADPARLLSSLDVLRDPEHAQLEALGNTAVLTRTPGPAVSVPELFATQVARAPQDVALV 480

MapK10 481 CEGRSLTYRQLDEASNRLAHLLAGLGAGPGQSVALLFSRSAEAVASILAVLKTGAAYLPI 540
           CEGRSLTYRQLDEASNRLAHLLAGLGAGPGQSVALLFSRSAEA+ +IL VLK+GAAYLPI
S397   481 CEGRSLTYRQLDEASNRLAHLLAGLGAGPGQSVALLFSRSAEAIVAILGVLKSGAAYLPI 540

MapK10 541 DPAAPETRIGFMLADAKPVAALSTAELAGRLEG-HGMTVIDVNDPRIQDRPATALPVPAA 599
           DPA P RIGFMLADA P+ A+STAELA RL G H + VIDV+DP I+ P++ALP P A
S397   541 DPALPGERIGFMLADAAPMVAISTAELAPRLHGQHDVPVIDVHDPAIEAAPSSALPPPGA 600

MapK10 600 DGVAYVIYTSGTTGVPKGVAVTHRNVTQLLGSLDAGLPPAGVWSQCHSYAFDVSVWEIFG 659
           D +AY+IYTSGTTGVPKGVAV+HRNVTQLL + D+GLP GVWSQ HS AFDVSVWEIFG
S397   601 DDIAYLIYTSGTTGVPKGVAVSHRNVTQLL-TADSGLPREGVWSQWHSLAFDVSVWEIFG 659

MapK10 660 ALLRGGRLVVVPEDVTRAPEELHDVLNEQVSVLTQTPSAVAMLSPQGLESVSLVVVGEA 719
           ALL GGRLVV+P+ V R+P++ H +L++EQVSVL+QTPSA LSP+GLE ++LVV GEA
S397   660 ALLHGGRLVVIPDSVVRSPDDFHALLLDEQVSVLSQTPSAAGTLSPEGLEDLTLVVAGEA 719

MapK10 720 CPAEVVDRWSPGRVMVNAYGPTETTMCVAISAPLAPGMGSPPIGVPVDGAGLFVLDAWLR 779
           CPAE+VDRW PGR M+NAYGPTETTMCVAISAPLAPGMGSPPIGVPVDGAGLFVLDAWLR
S397   720 CPAELVDRWAPGRTMINAYGPTETTMCVAISAPLAPGMGSPPIGVPVDGAGLFVLDAWLR 779

MapK10 780 PVPPGVVGELYVGGAGVACGYWRRGGLTASWFVACPFGAPGARMYRTGDLVCWRSDGQLD 839
           PVPPGVVGELYV GAGVACGYWRRGGLTAS FVACPFGAPGARMYRTGDLVCWRSDGQLD
S397   780 PVPPGVVGELYVAGAGVACGYWRRGGLTASRFVACPFGAPGARMYRTGDLVCWRSDGQLD 839

MapK10 840 YRGRADEQVKVRGYRIELGEVQAALAALDDVDQAVVIAREDRPGGKRLVGYITGTADPAE 899
           YRGRADEQVKVRGYRIELGEVQAALAALDDVDQAVVIAREDRPGGKRLVGYITGTADPAE
S397   840 YRGRADEQVKVRGYRIELGEVQAALAALDDVDQAVVIAREDRPGGKRLVGYITGTADPAE 899
```

FIG. 6A

```
MapK10  900 VRTALAQRLPVYMVPAAVVALDAIPLTPNGKLDTRALPTPEYTGSRYRAPSNAVEETVAG  959
            VRTALAQRLPVYMVPAAVVALDAIPLTPNGKLDTRALPTPEY+ YRAP + EE +AG
S397    900 VRTALAQRLPVYMVPAAVVALDAIPLTPNGKLDTRALPTPEYSTGEYRAPESPTEEILAG  959

MapK10  960 IYAHVLGVERVGVDDSFFDLGGDSISALQVVARARAAGLTCRPRDVFVEQTVARLARVVG 1019
            IYA VLGVERVGVD+SFFDLGGDSISA++VVARARAAGLTCRPRDVFVEQTVARLARVVG
S397    960 IYAEVLGVERVGVDESFFDLGGDSISAMRVVARARAAGLTCRPRDVFVEQTVARLARVVG 1019

MapK10 1020 SGDRAAEVADEGVGPVPPTPIMRWLQAAERAGGATDQFNQTVLVQAPAGVTETEVAIVLQ 1079
            SGDRAAEVADEGVGPVPPTPIMRWLQAAERAGGATDQFNQTVLVQAPAGVTETEVAIVLQ
S397    1020 SGDRAAEVADEGVGPVPPTPIMRWLQAAERAGGATDQFNQTVLVQAPAGVTETEVAIVLQ 1079

MapK10 1080 ALVDRHAMLRLRVTDDGADGWSFEVPEAGSVQARDCLRSVDALSDEALLAARARLNPAAG 1139
            ALVDRHAMLRLRVTDDGADGWSFEVPEAGSVQARDCLRSVDALSDEALLAARARLNPAAG
S397    1080 ALVDRHAMLRLRVTDDGADGWSFEVPEAGSVQARDCLRSVDALSDEALLAARARLNPAAG 1139

MapK10 1140 TMLAALWVEATGQLAVIIHHLAVDAVSWWILLEDLNIAWALHRAGQPVELAPAGTSFARW 1199
            TMLAALWVEATGQLAVIIHHLAVDAVSWWILLEDLNIAWALHRAGQPVELAPAGTSFARW
S397    1140 TMLAALWVEATGQLAVIIHHLAVDAVSWWILLEDLNIAWALHRAGQPVELAPAGTSFARW 1199

MapK10 1200 ARLLDEHARDPEVVGQLDRWKTVTSTPAALPAPRPDVDTYASAGRLSVELDAETTAMLLG 1259
            ARLLDEHARDPEVVGQLDRWKTVTSTPAALPAPRPDVDTYASAGRLSVELDAETTAMLLG
S397    1200 ARLLDEHARDPEVVGQLDRWKTVTSTPAALPAPRPDVDTYASAGRLSVELDAETTAMLLG 1259

MapK10 1260 EVPAAFHAGIHDILLIAFGLAWTEFLGEPGAPIGIDVEGHGRHEELGADIDLSRTVGWFT 1319
            EVPAAFHAGIHDILLIAFGLAWTEFLGEPGAPIGIDVEGHGRHEELGADIDLSRTVGWFT
S397    1260 EVPAAFHAGIHDILLIAFGLAWTEFLGEPGAPIGIDVEGHGRHEELGADIDLSRTVGWFT 1319

MapK10 1320 AKYPVSLDVAGLRWPQVAAGDPALGPVLKRAKEQLRTLPEPLTYGLLRYLNTDVDLAGAD 1379
            AKYPVSLDVAGLRWPQVAAGDPALGPVLKRAKEQLRTLPEPLTYGLLRYLNTDVDLAGAD
S397    1320 AKYPVSLDVAGLRWPQVAAGDPALGPVLKRAKEQLRTLPEPLTYGLLRYLNTDVDLAGAD 1379

MapK10 1380 PPIAFNYLGRQGAASDSAADGWRISQDMSLLGAAAAVPMPLMHAVELNAGTIDTGAGPHL 1439
            PPIAFNYLGRQGAASDSAADGWRISQDMSLLGAAAAVPMPLMHAVELNAGTIDTGAGPHL
S397    1380 PPIAFNYLGRQGAASDSAADGWRISQDMSLLGAAAAVPMPLMHAVELNAGTIDTGAGPHL 1439

MapK10 1440 HAEWTWAPSVLGAEQITRVSRLWFEALAGVCAHVRSGGGGGLTPSDIAPARLTQQQIDEL 1499
            HAEWTWAPSVLGAEQITRVSRLWFEALAGVCAHVRSGGGG LTPSDIAPARLTQQQIDEL
S397    1440 HAEWTWAPSVLGAEQITRVSRLWFEALAGVCAHVRSGGGG-LTPSDIAPARLTQQQIDEL 1498

MapK10 1500 QSRHRIADILPLTPLQQGLLFHSSTAQGNDGMDDMYAVQLDFTLTGPLDADRLREAVRTV 1559
            QSRHRIADILPLTPLQQGLLFHSSTAQGNDGMDDMYAVQLDFTLTGPLDADRLREAVRTV
S397    1499 QSRHRIADILPLTPLQQGLLFHSSTAQGNDGMDDMYAVQLDFTLTGPLDADRLREAVRTV 1558

MapK10 1560 VHRHPHLAALFCDQYDEPVQIIPADPAVEWRYVELDGTGAADADDLIEQLCAAERAAVAD 1619
            VHRHPHLAALFCDQYDEPVQIIPADPAVEWRYVELDGTGAADADDLIEQLCAAERAAVAD
S397    1559 VHRHPHLAALFCDQYDEPVQIIPADPAVEWRYVELDGTGAADADDLIEQLCAAERAAVAD 1618

MapK10 1620 LAGQPVFRTALVRTGGDRHRFVLTSHHILLDGWSLPILLREIFAGYYGQRLPAAGSYRAF 1679
            LAGQPVFRTALVRTGGDRHRFVLTSHHILLDGWSLPILLREIFAGYYGQRLPAAGSYRAF
S397    1619 LAGQPVFRTALVRTGGDRHRFVLTSHHILLDGWSLPILLREIFAGYYGQRLPAAGSYRAF 1678

MapK10 1680 LTWLAERDLDAARRAWGEVLSGFDTPTLVAPEGRLGQGRRGFEKSCVPEQTTRALGELAR 1739
            LTWLAERDLDAARRAWGEVLSGFDTPTLVAPEGRLGQGRRGFEKSCVPEQTTRALGELAR
S397    1679 LTWLAERDLDAARRAWGEVLSGFDTPTLVAPEGRLGQGRRGFEKSCVPEQTTRALGELAR 1738

MapK10 1740 SCHTTLSTVLQAAWAVVLTSLTGRHDVVFGTPRSRVGQLEVDDAEQMVGLLINTVPVRAE 1799
            SCHTTLSTVLQAAWAVVLTSLTGRHDVVFGTPRSRVGQLEVDDAEQMVGLLIN VPVRAE
S397    1739 SCHTTLSTVLQAAWAVVLTSLTGRHDVVFGTPRSRVGQLEVDDAEQMVGLLINAVPVRAE 1798
```

FIG. 6B

```
MapK10  1800  ITATTTTAQLLAQLQNSHNDTLEHQHLALNEIHRVTGHDQLFDTLFVYENYPIDSGMTLG  1859
              ITATTTTAQLLAQLQNSHNDTLEHQHLALNEIHRVTGHDQLFDTLFVYENYPIDSGMTLG
S397    1799  ITATTTTAQLLAQLQNSHNDTLEHQHLALNEIHRVTGHDQLFDTLFVYENYPIDSGMTLG  1858

MapK10  1860  ADGLAIAEFTNREYNHYPLTVEALPGPELGLHIEFDTDVFDTASIESLVQRLQRVLVAMS  1919
              ADGLAIAEFTNREYNHYPLTVEALPGPELGLHIEFDTDVFDTASIESLVQRLQRVLVAMS
S397    1859  ADGLAIAEFTNREYNHYPLTVEALPGPELGLHIEFDTDVFDTASIESLVQRLQRVLVAMS  1918

MapK10  1920  TDPDRRLSSLDLLDRGERELVLSTMSGAGVSAPIGVAPQLLAAAVAADPDAPAIVDGARE  1979
              TDPDRRLSSLDLLDRGERELVLSTMSGAGVSAPIGVAPQLLAAAVAADPDAPAIVDGARE
S397    1919  TDPDRRLSSLDLLDRGERELVLSTMSGAGVSAPIGVAPQLLAAAVAADPDAPAIVDGARE  1978

MapK10  1980  LSYRELDDWSTRLARKLIQHGVGPEHAAGVAIERCAELVVAWWAVTKVGGVYAPVNLDHP  2039
              LSYRELDDWSTRLARKLIQHGVGPEHAAGVAIERCAELVVAWWAVTK GGVYAPVNLD+P
S397    1979  LSYRELDDWSTRLARKLIQHGVGPEHAAGVAIERCAELVVAWWAVTKAGGVYAPVNLDYP  2038

MapK10  2040  VERIASVLDTVNAVCVLTCGTDEVAGAGPRPILRIDGLDLSGHSTEPITDADRRSPLRAD  2099
              VERIASVLDTVNAVCVLTCGTDEVAGAGPRPILRIDGLDLSGHSTEPITDADRRSPLRAD
S397    2039  VERIASVLDTVNAVCVLTCGTDEVAGAGPRPILRIDGLDLSGHSTEPITDADRRSPLRAD  2098

MapK10  2100  DTAYLIFTSGSTGVPKGVAVSHTGLLGWAAAQRELFGLGADARVLMVASPTFDASVGELL  2159
              DTAYLIFTSGSTGVPKGVAVSHTGLLGWAAAQRELFGLGADARVLMVASPTFDASVGELL
S397    2099  DTAYLIFTSGSTGVPKGVAVSHTGLLGWAAAQRELFGLGADARVLMVASPTFDASVGELL  2158

MapK10  2160  LAAGSGAALIVAPPQVYAGEALTALLHNQRVGTAILTPTVISTLDRGRLDGLHTLVAVGE  2219
              LAAGSGAALIVAPPQVYAGEALTALLHNQRVGTAILTPTVISTLDRGRLDGLHTLVAVGE
S397    2159  LAAGSGAALIVAPPQVYAGEALTALLHNQRVGTAILTPTVISTLDRGRLDGLHTLVAVGE  2218

MapK10  2220  ACLPELVDGWAPGRQMFNGYGPSETTIWVTCARLTAGHPVRIGAPIPGVCARVLDGWLKP  2279
              ACLPELVDGWAPGRQMFNGYGPSETTIWVTCARLTAGHPVRIGAPIPGVCARVLDGWLKP
S397    2219  ACLPELVDGWAPGRQMFNGYGPSETTIWVTCARLTAGHPVRIGAPIPGVCARVLDGWLKP  2278

MapK10  2280  VPVGVVGELYLSGPALGHGYLGRVDLTAERFVANPFGGPGERMYRTGDLVRWTPEGTLDY  2339
              VPVGVVGELYLSGPALGHGYLGRVDLTAERFVANPFGGPGERMYRTGDLVRWTPEGTLDY
S397    2279  VPVGVVGELYLSGPALGHGYLGRVDLTAERFVANPFGGPGERMYRTGDLVRWTPEGTLDY  2338

MapK10  2340  LGRADNQIKLRGQRIELGEIENTLLACPQVTQAAVTVQDSAAGSQLVAYVTLDHGPSDAD  2399
              LGRADNQIKLRGQRIELGEIENTLLACPQVTQAAVTVQDSAAGSQLVAYVTLDHGPSDAD
S397    2339  LGRADNQIKLRGQRIELGEIENTLLACPQVTQAAVTVQDSAAGSQLVAYVTLDHGPSDAD  2398

MapK10  2400  VRHDTDDADDVAQWRHLYDDLYGADLAATFGEDFRGWNSSYTGEPIPLQEMAEWRSATVD  2459
              VRHDTDDADDVAQWRHLYDDLYGADLAATFGEDFRGWNSSYTGEPIPLQEMAEWRSATVD
S397    2399  VRHDTDDADDVAQWRHLYDDLYGADLAATFGEDFRGWNSSYTGEPIPLQEMAEWRSATVD  2458

MapK10  2460  RIMSLRPRRVLEIGAGSGLLLSQIAPRCDRYVATDFSAVAIDNLARSMEQLQLPWRDRVE  2519
              RIMSLRPRRVLEIGAGSGLLLSQIAPRCDRYVATDFSAVAIDNLARSMEQLQLPWRDRVE
S397    2459  RIMSLRPRRVLEIGAGSGLLLSQIAPRCDRYVATDFSAVAIDNLARSMEQLQLPWRDRVE  2518

MapK10  2520  LLTQPAHVTDGLPPGHFDTIVINSVVQYFPNAGYLADVIDNALELLAPGGSLFIGDVRNH  2579
              LLTQPAHVTDGLPPGHFDTIVINSVVQYFPNAGYLADVIDNALELLAPGGSLFIGDVRNH
S397    2519  LLTQPAHVTDGLPPGHFDTIVINSVVQYFPNAGYLADVIDNALELLAPGGSLFIGDVRNH  2578

MapK10  2580  ALQGAFQTGIALARGGGADAAEIRQRVRHAMLGETELLLAPEFFTNWADSRPAAAGLDIQ  2639
              ALQGAFQTGIALARGGGADAAEIRQRVRHAMLGETELLLAPEFFTNWADSRPAAAGLDIQ
S397    2579  ALQGAFQTGIALARGGGADAAEIRQRVRHAMLGETELLLAPEFFTNWADSRPAAAGLDIQ  2638

MapK10  2640  LKRGLSDNELNRYRYDVVIHKAPAPVRSVAAAPTWSWTDCTDCAGLRDQLAARRPAVVRV  2699
              LKRGLSDNELNRYRYDVVIHKAPAPVRSVAAAPTWSWTDCTDCAGLRDQLAARRPAVVRV
S397    2639  LKRGLSDNELNRYRYDVVIHKAPAPVRSVAAAPTWSWTDCTDCAGLRDQLAARRPAVVRV  2698
```

FIG. 6C

```
MapK10  2700  TDIPQAGVIDDVRVEAALAAGLPVADALAAAGSDTAAAVAEELHRVGEATGYRVAVTWGA  2759
              TDIPQAGVIDDVRVEAALAAGLPVADALAAAGSDTAAAVAEELHRVGEATGYRVAVTWGA
S397    2699  TDIPQAGVIDDVRVEAALAAGLPVADALAAAGSDTAAAVAEELHRVGEATGYRVAVTWGA  2758

MapK10  2760  QPGTLSAVFVQDGDQAAEPLTDLYLPPAGARQRTRHANDPRANTKIAQVRERLNAWLPEY  2819
              QPGTLSAVFVQDGDQAAEPLTDLYLPPAGARQRTRHANDPRANTKIAQVRERLNAWLPEY
S397    2759  QPGTLSAVFVQDGDQAAEPLTDLYLPPAGARQRTRHANDPRANTKIAQVRERLNAWLPEY  2818

MapK10  2820  MVPTHIVALDEFPMTTSGKLDRKALPAPDYQDADRYRAPSTAVEEILVGIYGQVLGLERV  2879
              MVPTHIVALDEFPMTTSGKLDRKALPAPDYQDADRYRAPSTAVEEILVGIYGQVLGLERV
S397    2819  MVPTHIVALDEFPMTTSGKLDRKALPAPDYQDADRYRAPSTAVEEILVGIYGQVLGLERV  2878

MapK10  2880  GVDDSFFDLGGDSLSAMRLIAAVNASLNTDLGVRTVFEAPTAAELALRVGSEADRPEPLV  2939
              GVDDSFFDLGGDSLSAMRLIAAVNASLNTDLGVRTVFEAPTAAELALRVGSEADRPEPLV
S397    2879  GVDDSFFDLGGDSLSAMRLIAAVNASLNTDLGVRTVFEAPTAAELALRVGSEADRPEPLV  2938

MapK10  2940  AGERPAVIPLSFAQTRLWFIDQFQGPSPMYNITVALRLSGRLDADALRAALADVVARHES  2999
              AGERPAVIPLSFAQTRLWFIDQFQGPSPMYNITVALRLSGRLDADALRAALADVVARHES
S397    2939  AGERPAVIPLSFAQTRLWFIDQFQGPSPMYNITVALRLSGRLDADALRAALADVVARHES  2998

MapK10  3000  LRTVFATADGTPQQVVIPADRIGFACDVVDARGWPEDRLREAMSAAARYTFDLSAESPLH  3059
              LRTVFATAD TPQQVVIPADRIGFACDVVDARGWPEDRLREAMSAAARYTFDLSAESPLH
S397    2999  LRTVFATADATPQQVVIPADRIGFACDVVDARGWPEDRLREAMSAAARYTFDLSAESPLH  3058

MapK10  3060  TELFARGDDEHVLVVAVHHIAADGWSITPFARDLGVAYASRCAGRDPDWAPLPVQYADYT  3119
              TELFARGDDEHVLVVAVHHIAADGWSITPFARDLGVAYASRCAGRDPDWAPLPVQYADYT
S397    3059  TELFARGDDEHVLVVAVHHIAADGWSITPFARDLGVAYASRCAGRDPDWAPLPVQYADYT  3118

MapK10  3120  LWQRAHLGDVDDPGSRIAAQLDFWTDALAGLPERLQLPTDRPYPAVADHRGARLAVDWPA  3179
              LWQRAHLGDVDDPGSRIAAQLDFWTDALAGLPERLQLPTDRPYPAVADHRGARLAVDWPA
S397    3119  LWQRAHLGDVDDPGSRIAAQLDFWTDALAGLPERLQLPTDRPYPAVADHRGARLAVDWPA  3178

MapK10  5290  ELQQRIGDVAHRHNATSFMVIQTALTVLLAKLGANPDVAVGFPIAGRRDPALDDLVGFFV  5349
              ELQQRIGDVAHRH+ATSFMVIQTALTVLLAKLGANPDVAVGFPIAGRRDPALDDLVGFFV
S397    3179  ELQQRIGDVAHRHDATSFMVIQTALTVLLAKLGANPDVAVGFPIAGRRDPALDDLVGFFV  3238

MapK10  5350  NTLVLRVDAAGDPSFTELLARVRTRSLEAFEHQDVPFEVLVERLNPTRSLTHHPLVQVML  5409
              NTLVLRVDAAGDPSFTELLARVRTRSLEAFEHQDVPFEVLVERLNPTRSLTHHPLVQVML
S397    3239  NTLVLRVDAAGDPSFTELLARVRTRSLEAFEHQDVPFEVLVERLNPTRSLTHHPLVQVML  3298

MapK10  5410  AWQNFAGQDTGPAAGLSLGDVEITPIPVDTHTARMDLTFSVGERWCESGEPGGIGGTVEF  5469
              AWQNFAGQDTGPAAGLSLGDVEITPIPVDTHTARMDLTFSVGERWCESGEPGGIGGTVEF
S397    3299  AWQNFAGQDTGPAAGLSLGDVEITPIPVDTHTARMDLTFSVGERWCESGEPGGIGGTVEF  3358

MapK10  5470  RTDVFDPDSIQTLIGRLRRVLEAMTDDPTQSVWSVDLLDAGEHARLDTLGNRAALTGPPP  5529
              RTDVFDPDSIQTLIGRLRRVLEAMTDDPTQSVWSVDLLDAGEHARLDTLGNRAALTGPPP
S397    3359  RTDVFDPDSIQTLIGRLRRVLEAMTDDPTQSVWSVDLLDAGEHARLDTLGNRAALTGPPP  3418

MapK10  5530  RFDSLPTLFAEQAARTPDAVALVCGGRRMTYRELDEAANRVAHLLRVRGAGPGHTVALLF  5589
              RFDSLPTLFAEQAARTPDAVALVCGGRRMTYRELDEA+NR+AHLL GAGPG +VALLF
S397    3419  RFDSLPTLFAEQAARTPDAVALVCGGRRMTYRELDEASNRLAHLLAGLGAGPGQSVALLF  3478

MapK10  5590  SRSAEAIVAILGVLKSGAAYLPIDPALPGERIGFMLADAAPMVAISTAELAPRLHGQHDV  5649
              SRSAEAIVAILGVLKSGAAYLPIDPALPGERIGFMLADAAPMVAISTAELAPRLHGQHDV
S397    3479  SRSAEAIVAILGVLKSGAAYLPIDPALPGERIGFMLADAAPMVAISTAELAPRLHGQHDV  3538

MapK10  5650  PVIDVHDPAIEAAPSSALPPPGADDIAYLIYTSGTTGVPKGVAVSHRNVTQLLTADSGLP  5709
              PVIDVHDPAIEAAPSSALPPPGADDIAYLIYTSGTTGVPKGVAVSHRNVTQLLTADSGLP
S397    3539  PVIDVHDPAIEAAPSSALPPPGADDIAYLIYTSGTTGVPKGVAVSHRNVTQLLTADSGLP  3598
```

FIG. 6D

```
MapK10  5710  REGVWSQWHSLAFDVSVWEIFGALLHGGRLVVIPDSVVRSPDDFHALLLDEQVSVLSQTP  5769
              REGVWSQWHSLAFDVSVWEIFGALLHGGRLVVIPDSVVRSPDDFHALLLDEQVSVLSQTP
S397    3599  REGVWSQWHSLAFDVSVWEIFGALLHGGRLVVIPDSVVRSPDDFHALLLDEQVSVLSQTP  3658

MapK10  5770  SAAGTLSPEGLEDLTLVVAGEACPAELVDRWAPGRTMINAYGPTEATVYTAISAPLQPGS  5829
              SAAGTLSPEGLEDLTLVVAGEACPAELVDRWAPGRTMINAYGPTEATVYTAISAPLQPGS
S397    3659  SAAGTLSPEGLEDLTLVVAGEACPAELVDRWAPGRTMINAYGPTEATVYTAISAPLQPGS  3718

MapK10  5830  PAGVPIGFPVPGAGLFVLDESLRPVPPGVVGELYVGGAGVACGYWRRGGLTASWFVACPF  5889
              PAGVPIGFPVPGAGLFVLDESLRPVPPGVVGELYV GAGVACGYWRRGGLTAS FVACPF
S397    3719  PAGVPIGFPVPGAGLFVLDESLRPVPPGVVGELYVAGAGVACGYWRRGGLTASRFVACPF  3778

MapK10  5890  GAPGARMYRTGDLVCWRSDGQLDYRGRADEQVKVRGYRIELGEVQAALAGLDDVEQAVVI  5949
              GAPGARMYRTGDLVCWRSDGQLDYRGRADEQVKVRGYRIELGEVQAALA LDDV+QAVVI
S397    3779  GAPGARMYRTGDLVCWRSDGQLDYRGRADEQVKVRGYRIELGEVQAALAALDDVDQAVVI  3838

MapK10  5950  AREDRPGGKRLVGYITGTADPAEVRTALAQRLPVYMVPAAVVALDAIPLTPNGKLDTRAL  6009
              AREDRPGGKRLVGYITGTADPAEVRTALAQRLPVYMVPAAVVALDAIPLTPNGKLDTRAL
S397    3839  AREDRPGGKRLVGYITGTADPAEVRTALAQRLPVYMVPAAVVALDAIPLTPNGKLDTRAL  3898

MapK10  6010  PTPEYTGSRYRAPSNAVEETVAGIYAHVLGVERVGVDDSFFDLGGDSISAMRVITAINAS  6069
              PTPEYTGSRYRAPSNAVEETVAGIYAHVLGVERVGVDDSFFDLGGDSISAMRVITAINAS
S397    3899  PTPEYTGSRYRAPSNAVEETVAGIYAHVLGVERVGVDDSFFDLGGDSISAMRVITAINAS  3958

MapK10  6070  LGVELAVRTLFEAPTVASLSWRAQTDTARGGQAEEIVPVQTLKEGTGAPLFCIHAAGGLS  6129
              LGVELAVRTLFEAPTVASLSWRAQTDTARGGQAEEIVPVQTLKEGTGAPLFCIHAAGGLS
S397    3959  LGVELAVRTLFEAPTVASLSWRAQTDTARGGQAEEIVPVQTLKEGTGAPLFCIHAAGGLS  4018

MapK10  6130  WSYQVLGNHLDCPIIGIQQAEPQHAAPRSIREMAQSYADRIQETYPDGPYHLVGWSFGGV  6189
              WSYQVLGNHLDCPIIGIQQAEPQHAAPRSIREMAQSYADRIQETYPDGPYHLVGWSFGGV
S397    4019  WSYQVLGNHLDCPIIGIQQAEPQHAAPRSIREMAQSYADRIQETYPDGPYHLVGWSFGGV  4078

MapK10  6190  VAHELAIELQRRGCAIARLVLLDAQPGLDGSVTAPDAALAEQHMMEEALRSHLAAADHDQ  6249
              VAHELAIELQRRGCAIARLVLLDAQPGLDGSVTAPDAALAEQHMMEEALRSHLAAADHDQ
S397    4079  VAHELAIELQRRGCAIARLVLLDAQPGLDGSVTAPDAALAEQHMMEEALRSHLAAADHDQ  4138

MapK10  6250  PHAHRQFNQLVREAGAEGMSRHKRLFDVLFGNARNNIERSKIHEPGVFLGDTIFSAVRD  6309
              PHAHRQFNQLVREAGAEGMSRHKRLFDVLFGNARNNIERSKIHEPGVFLGDTIFSAVRD
S397    4139  PHAHRQFNQLVREAGAEGMSRHKRLFDVLFGNARNNIERSKIHEPGVFLGDTIFSAVRD  4198

MapK10  6310  HEDRSAFLAENWRPYVAGDIVIHEIDCTHDEILNADVVDSYGQRLGQLLGAQRRRELTPP  6369
              HEDRSAFLAENWRPYVAGDIVIHEIDCTHDEILNADVVDSYGQRLGQLLGAQRRRELTPP
S397    4199  HEDRSAFLAENWRPYVAGDIVIHEIDCTHDEILNADVVDSYGQRLGQLLGAQRRRELTPP  4258

MapK10  6370  QRFGADPGDDEPPVR  6384
              QRFGADPGDDEPPVR
S397    4259  QRFGADPGDDEPPVR  4273
```

FIG. 6E

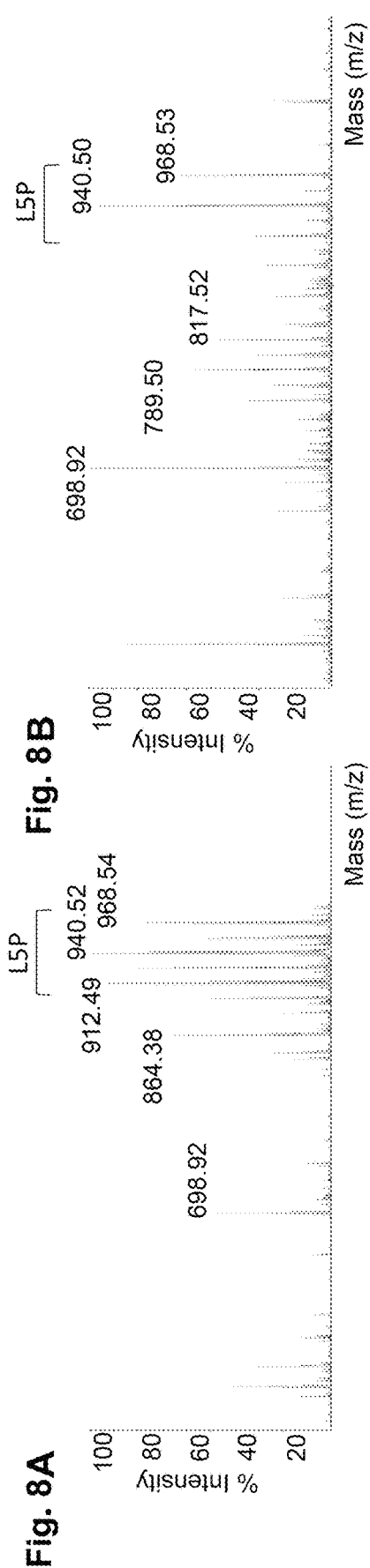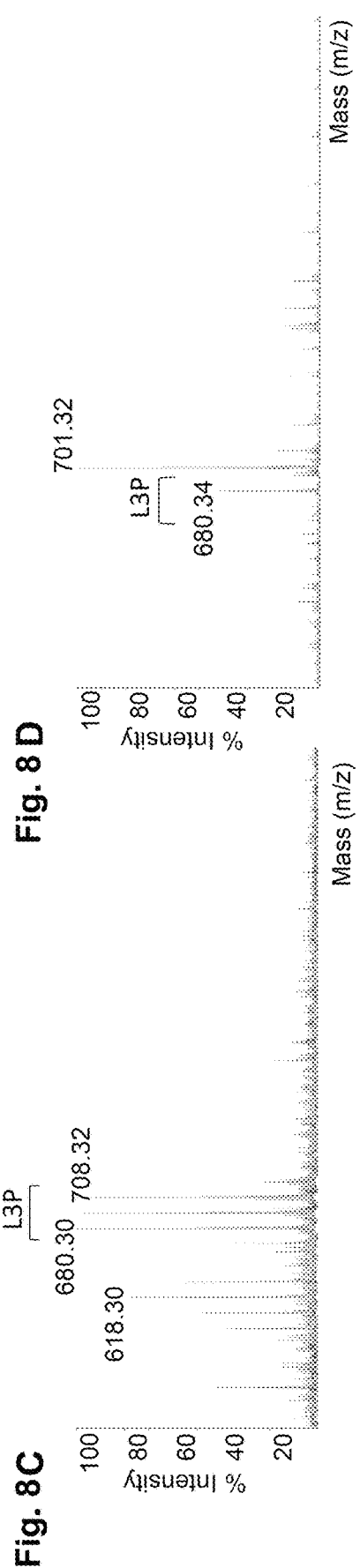

ANTIGENIC TRIPEPTIDES DERIVED FROM *MYCOBACTERIUM AVIUM* SUBSP. *PARATUBERCULOSIS* S-TYPE STRAINS, DERIVATIVES AND USES THEREOF

CROSS-REFERENCE TO RELATED APPLICATIONS

This application is a divisional of U.S. application Ser. No. 16/470,962, filed Jun. 18, 2019, which is the U.S. National Stage Entry of PCT/EP2017/083924, filed Dec. 20, 2017, which claims the benefit of U.S. PCT/162016/002018 filed on Dec. 20, 2016, the contents of which are incorporated herein by reference in their entirety for all purposes.

REFERENCE TO SEQUENCE LISTING SUBMITTED ELECTRONICALLY

The contents of the electronic sequence listing (B12263WOUS1.xml; Size: 59,213 bytes; and Date of Creation: Oct. 7, 2022) is herein incorporated by reference in its entirety.

The present invention is directed to the diagnosis, prevention and treatment of diseases resulting from infections by *Mycobacterium avium* subsp. *paratuberculosis*.

*Mycobacterium* is a genus of Actinobacteria and includes pathogens known to cause serious diseases in mammals, including tuberculosis and leprosy.

The mycobacterial cell envelope is unique among prokaryotes in that it contains unusual lipid and carbohydrate compounds, such as lipoarabinomannan and mycolic acids. The mycomembrane, an unusual outer membrane, corresponds to the permeability barrier of which inner leaflet is formed by a parallel arrangement of mycolic acids covalently linked to parietal backbone. Mycolic acids are the main components of this mycomembrane and constitute up to 60% of the lipid content of the cell wall. The outer-most layers of the cell envelope, or capsule, are composed of several types of glycolipids embedded in the saccharidic matrix surrounding the bacillus. The three major classes of type- or species-specific glycolipids include the lipooligosaccharides, phenolic glycolipids and glycopeptidolipids (GPLs). It is not clear why different lipids exist among these species of mycobacteria, but these differences have been exploited to catalog and distinguish species in this genus. Rapid growing mycobacteria, including *M. chelonae, M. scrofulaceum, M. abscessus*, and slow growing mycobacteria such as *M. avium* subsp. *avium* produce GPLs in their cell envelope (Ripoll et al., 2007). Recently, *M. abscessus* strains showing rough colony morphology were found to lack GPLs and the majority of these variants could be linked to a detrimental mutation in one of eight genes in the GPL locus.

*Mycobacterium avium* subsp. *paratuberculosis* (Map or MAP) infects different animals, essentially mammals, including bovine, ovine and caprine animals; the most commonly infected animals being cattle, sheep, goats. In addition to domesticated farm animals, Map also infects wild animals such as red deer, rabbits, bisons and buffalo.

Map is the causative agent of Johne's disease in cattle and other ruminants, a chronic progressive intestinal disease that is difficult to accurately diagnose, especially in the early stages of disease. One of the difficulties in the early diagnosis of Map infection is indeed that the pathogen remains latent for years without development of any clinical signs or disease. Infected but healthy animals, transmit the pathogen either in utero, through contaminated colostrum or milk, or through manure as MAP is shed from infected animals in feces, thus spreading the infection.

This problem of silent transmission has hindered efforts to control or eliminate the disease from dairy herds. Johne's disease is widely distributed on five continents and the most affected countries are in North America, Europe and Australia. According to the most recent National Animal Health Monitoring System survey (NAHMS, 2008), Johne's disease prevalence has increased to over 90% of U.S. dairy herds. Four distinct stages of disease progression have been described as silent infection, subclinical disease, clinical disease, and advanced clinical disease. The last two stages often develop after several years of infection. Typical advanced stage signs are weight loss, diarrhea, lethargy, and increased weakness. However, the economic toll on the dairy industry is the primary motivation for efforts at disease control. A United States Department of Agriculture (USDA) study estimated the loss of approximately $200 per cow each year with an overall economic loss of between $200 million to $250 million dollars annually to the U.S. dairy industry. There is no treatment to Johne's disease in cattle and the affected animals are culled when they begin to exhibit clinical signs of disease, especially decreased milk production for cows.

The accurate and early diagnosis of the disease is thus of outmost importance. In this respect, a suitable diagnostic must be able to discriminate between Map infection and infection by other *M. avium*, such as *M. avium* subsp. *avium* (Maa or MAA), and also infection by *M. bovis*, the causative agent of tuberculosis in cattle (bovine tuberculosis). Moreover, insofar as the animals positively diagnosed are culled, one important need is also to provide a diagnostic test limiting the undetermined results, i.e. those results which do not allow any decision to be made on the basis of the diagnosis result.

Recently, it has also been shown that Map is associated to Crohn's Disease (CD) in humans. CD is a gastrointestinal disorder, characterized inter alia by severe abdominal pain, diarrhea, bowel obstruction. Map is suspected to be involved in the disease process of CD or other gastrointestinal disorders.

Although the importance of Johne's disease in cattle and the potential involvement in CD, the causative mycobacteria Map is not yet entirely characterized, especially due to the difficulty in culturing the mycobacteria. Map is indeed an extremely slow-growing mycobacteria and requires fastidious culture conditions to grow.

Two lineages of Map have recently been identified, which are classified as type I/III or S-type (ovine) and type II or C-type (bovine) strains. The S-type isolates are readily distinguishable from C-type isolates inter alia based on genome sequencing studies.

There is thus a need for improved diagnostic tests to detect specifically paratuberculosis infection, which are simple, rapid, noninvasive, that can be performed by veterinarians or producers without expensive laboratory equipment and which limits the undetermined results. There is also a need for veterinary diagnostics that are sensitive (to detect MAP at early stages of infection) and specific (identity of MAP and not other microorganisms) to eliminate MAP from the commercial food supply especially due to its suspected involvement on CD.

Bacteriologic culture is the most accurate method of diagnosis, since it can detect infection during both the subclinical and clinical stages of disease, but it is time-consuming, requiring as many as 12 weeks of incubation, and is also labor-intensive. The intradermal skin test evaluates the delayed-type hypersensitivity reaction of an animal by injection of *M. avium* subsp. *paratuberculosis* extracts; however, problems involving antigenic cross-reactivity with other mycobacteria have limited its usefulness. Serologic tests for diagnosis of paratuberculosis based on mycobacterial whole-cell antigen mixtures or secreted proteins are relatively easy to perform but suffer from a lack of specificity, especially for the S-type. In tests that measure a cell-mediated host response, it has been demonstrated that young animals and uninfected cattle often respond to mycobacterial whole-cell antigen mixtures or secreted proteins in the gamma interferon test without showing any evidence of infection.

In this respect, it is noted that most of the previously known antigen-based diagnostic tests for Johne's disease used a complex mixture of antigens, many of which are highly conserved among mycobacterial species; they thus give high number of false positive reactions. Moreover, there are only around 40 genes which have been identified as exclusively present in the MAP genome in comparison to the closely related *M. avium* subsp. *Avium* (Maa or MAA). Therefore, considering the high degree of similarity between MAP and MAA, specific antigens for use in diagnostic tests and vaccines for MAP-infection have been difficult to identify and considerable research has been directed towards the discovery of MAP specific antigens with potential diagnostic value.

In this search for *M. avium* subsp. *paratuberculosis*-specific antigens, the present inventors have previously discovered that all Map strains they tested produce a lipopentapeptide (L5P) instead of GPLs produced by many non-tuberculous mycobacteria such as *M. avium* subsp. *avium* (Maa). The sequence of the pentapeptide is based on Phe-Val-Ile-Phe-Ala, the lipopentapeptide L5P is produced by the non-ribosomal protein synthase (Nrp) of Map. The inventors have previously chemically synthesized L5P and shown that L5P is the target for a highly specific humoral response and that the major epitopes of the L5P are localized in the peptidyl moiety of the molecule (see also example 2 of the present experimental section). They also showed that L5P is the target for a specific humoral response in a subset of human patients with Crohn disease (CD). The L5P is thus a molecular signature of Map, opening now possibilities for the diagnosis of Map infection. This antigen has been used successfully in the serodiagnosis of Johne's disease in cattle (see inter alia WO2009/053844 and U.S. Pat. No. 8,883,173) and in T-cell assay (Holbert et al., 2015).

The inventors have however now shown that the lipopentapeptide L5P, is a signature specific to C-type Map, and is absent from S-type.

There is thus a need for improved diagnostic tests to detect *M. paratuberculosis* infection, and especially diagnostic tests specific to S-type Map. There is thus inter alia a need for an antigenic signature specific to S-type Map, as specific and sensitive as the signature recently identified by the inventors for the C-type isolates of Map. A good diagnostic antigen is ideally one that is able to be recognized by the immune cells and antibodies of MAP-affected animals, even in subclinical stages of infection, thus allowing diagnosis on the basis of humoral response and cell mediated response of infected animals.

Moreover, for the diagnosis of Map infection, either C-type or S-type, as with many other animal diseases, efforts need to be concentrated on the development of tests that can be performed by veterinarians or animal producers without expensive laboratory equipment. In this context, there is inter alia a need for tests which make use of hydrosoluble antigens, not requiring the use of solvents like methanol or ethanol.

Non-ribosomally synthesized peptides include a diverse class of important metabolites such as antibiotics. Non-ribosomal peptides (NRP) are usually 3-10 amino acids in length and are synthesized by large multi-modular enzymes called non-ribosomal-peptide synthetases (NRPSs). As the name implies, these peptides are not assembled by ribosome, but rather are RNA template and ribosomal independent to allow for maximum biological flexibility by incorporating many unique amino acids. In Map the mps1 gene encodes a NRPS with 5 modules that have been previously shown to be involved in production of the pentapeptidic moiety of the lipopentapeptide (L5P) (Biet et al., 2008).

The present inventors have now demonstrated that, depending on the strain type, Map produce different lipopeptide components. They have demonstrated by biochemical and physico-chemical analyses that typical lipopeptides from Map are different in S-type (lipotripeptide) and C-type strains (lipopentapeptide). They have inter alia found that the Map S-type produces the tripeptide H-D-Phe-N-Me-L-Val-L-Ala-OMe (SEQ ID NO:1), attached in N-terminal to a lipid moiety, namely a 20-carbon saturated fatty acid chain; this lipotripeptide will be designated L3P in the following. They have moreover demonstrated that this lipotripeptide is cell surface exposed, and have proven the immunoreactivity of this compound, as well as its capacity to induce humoral response and cell-mediated response.

In the context of the present invention, the amino-acids are designated by their usual symbols in the three-letters code; DPhe or D-Phe designates D-Phenylalanine, NMeVal or N-Me-Val designates N-methylated valine, Ala-OMe designates O-methyl esterified Alanine.

These findings of the inventors allow them to propose this tripeptide, as well as variants, derivatives and conjugates thereof as a signature of Map S-type, and the use thereof for the diagnosis or treatment of Map-associated diseases, especially Map S-type.

Moreover, the inventors have also demonstrated that specific chemical modifications to the lipopentapeptide produced by C-type strains give rise to a hydrosoluble analogue of this lipopentapeptide, having the same immunoreactivity as the natural or synthetic lipopentapeptide. These findings of the inventors allow them to propose hydrosoluble analogues of the lipotripeptide and of the lipopentapeptide Map S-type and C-type respectively.

DETAILED DESCRIPTION OF THE INVENTION

The present invention is directed to the L3P lipotripeptide and its peptidyl moiety specific to S-type strain, as well as derivatives and conjugates thereof; the invention also concerns the use of these antigens in different methods and tests for detecting Map infection, especially by detecting humoral response and cell mediated response of infected animals. The invention is also directed to a genetic signature and a MALDI-TOF (Matrix-Assisted Laser Desorption Ionization-Time Of Flight) spectrometry signature of S-type MAP.

The present inventors have also been able to identify a hydrosoluble analogue of the lipopentapeptide L5P, which is as specific as the natural L5P and thus suitable in diagnosis of Map, especially C-type Map.

According to a first aspect, the invention is directed to a tripeptide corresponding to the peptidyl moiety of the lipotripeptide specific to Map S-type, namely the tripeptide H-D-Phe-N-Methyl-L-Val-L-Ala-OMe, and to variants thereof. This tripeptide is indeed specific to S-type strains or isolates of Map as demonstrated by the inventors, and is recognized by antibodies specific to Map S-type.

The invention thus more generally concerns a tripeptide comprising a N-terminal Phenylalanine, a Valine and a C-terminal Alanine, linked by peptide bonds, and to variants thereof. The three amino acids F (Phe), V (Val) and A (Ala) may be naturally occurring amino acids, or non-canonical variants thereof.

In this respect, in a tripeptide according to the invention, the N-terminal phenylalanine residue is preferably a D-Phenylalanine. The Valine and Alanine are preferably L amino acids.

Moreover, it is preferred that the Valine be modified, namely by incorporation of an N-alkyl moiety, especially a methyl moiety, thus mimicking the natural tripeptide.

Similarly, the C-terminal Alanine is preferably O-modified, especially by incorporation of an O-alkyl ester moiety, preferably a O-methyl, thus mimicking the natural tripeptide.

The tripeptide according to the invention is thus preferably to be chosen in the group consisting in.

(a) a tripeptide of formula H-D-Phe-N-Methyl-L-Val-L-Ala-OMe,
(b) a tripeptide of formula H-L-Phe-N-Methyl-L-Val-L-Ala-OMe,
(c) a tripeptide of formula H-D-Phe-L-Val-L-Ala-OMe;
(d) a tripeptide of formula H-D-Phe-N-Methyl-L-Val-L-Ala-OH;
(e) a tripeptide of formula H-L-Phe-L-Val-L-Ala-OMe;
(f) a tripeptide of formula H-D-Phe-L-Val-L-Ala-OH;
(g) a tripeptide of formula H-L-Phe-N-Methyl-L-Val-L-Ala-OH; and
(h) a tripeptide of formula H-L-Phe-L-Val-L-Ala-OH.

The tripeptide according to the present invention is preferably a synthetic tripeptide, by opposition to a native tripeptide, namely a tripeptide which has not been synthesized by mycobacteria.

A preferred tripeptide is an isolated tripeptide, namely not part of a mycobacteria cell envelope.

The invention also provides tripeptide variants of the tripeptides defined above, namely tripeptide variants of the tripeptides (a) to (h), obtained for example by one or more of the following chemical modifications:
- replacement of L-Val by D-Val, replacement of L-Ala by D-Ala, or simultaneous replacement of L-Val and L-Ala by D-Val and D-Ala;
- modification of the peptidic bond or peptide backbone, inter alia via N-hydroxylation, ester linkages (α-hydroxy acids); insertion of extra methylene groups (β- and γ-amino acids); peptoids, azapeptides, oligoureas, arylamides, oligohydrazides; or a peptidomimetic of the tripeptide with modified backbone or linkage;
- retro-inversion of the tripeptide sequence;
- N-alkylation of the azote atom of Phe, Val and/or Ala, preferably N-methylation or N-ethylation of the Val and/or Ala, preferably of the Val;
- Replacement of the —OH or —OCH$_3$ group at the C-terminus of the Alanine, by another O-alkyl moiety, preferably by O-ethyl or O-butyl;
- Amidation of the C-terminus of Ala.

A tripeptide or tripeptide variant according to the invention is able to react with specific anti-Map antibodies, inter alia in Elisa tests as described in the experimental section.

"Specific anti-Map antibodies" herein refers to antibodies which are directed against antigenic determinants present in *Mycobacterium avium* subsp. *paratuberculosis* (Map) and absent in other species of mycobacteria and also absent in other subspecies of *M. avium*, i.e. said antibodies react with Map and do not cross-react with other mycobacteria. Preferably, said antibodies belong to the IgM, IgG1 or IgG2 class. It is preferred that specific anti-Map antibodies according to the invention are antibodies directed against S-type Map.

A tripeptide or tripeptide variant according to the invention is able to specifically react with specific anti-Map S-type antibodies. Specific anti-Map S-type antibodies are for example antibodies found in the serum of animals infected by Map S-type, which do not cross react with antigens of other mycobacteria, especially do not cross react with antigens of Maa and *M. bovis*. Cross-reaction with antibodies specific to Map C-type is however expected, due to the similar structure of L5P, characterizing C-type strains, and of L3P, characterizing the S-type strains. Specifically, a tripeptide or tripeptide variant according to the invention reacts with the same antibodies as those recognizing natural or synthetic L3P disclosed in this invention and in the experimental section.

In place or in addition to the above-mentioned modifications, the invention also concerns a tripeptide conjugate, consisting or comprising a tripeptide or tripeptide variant as disclosed above, further modified by:
- addition of a non-peptide protecting or capping moiety at the N-terminus, at the C-terminus, or simultaneously at the N- and C-terminus,
- N-acylation of the N-terminal Phe, preferably N-acetylation, inter alia N-acylation with a $C_1$ to $C_{30}$ acyl moiety, which is not a fatty acid moiety,
- glycosylation, biotinylation, labeling, including labeling by a fluorophore, conjugation to a protein carrier, derivatization with a bi-functional spacer arm for further conjugation (either in liquid phase or on a solid support);
- N-acylation of the N-terminal Phe with a $C_1$ to $C_{30}$ aliphatic acyl moiety, most preferably a $C_{10}$ to $C_{28}$ fatty acid moiety, and even most preferably with a $C_{18}$-$C_{22}$ saturated or unsaturated fatty acid moiety.

A preferred conjugate of the present invention is obtained by N-acylation of the N-terminal Phe by a lipid, preferably a saturated or unsaturated fatty acid moiety, thus giving rise to a lipotripeptide.

A preferred $C_{10}$ to $C_{28}$ fatty acid moiety is a $C_{10}$ to $C_{28}$ saturated or unsaturated fatty acid moiety, preferably saturated fatty acid moiety, and most preferably a $C_{18}$-$C_{22}$ saturated fatty acid moiety. According to a most preferred embodiment, the terminal Phe is N-acylated with an eicosanoic acid acyl chain.

A tripeptide conjugate according to the invention is able to specifically react with specific anti-Map antibodies, inter alia in Elisa tests as described in the experimental section, and more preferably with anti-Map S-type antibodies. Specifically, a tripeptide conjugate according to the invention reacts with the same antibodies as those recognizing natural or synthetic L3P disclosed in this invention and in the experimental section.

According to a specific embodiment of the tripeptide, tripeptide variant or tripeptide conjugate as disclosed above, the methyl ester present at the C-terminus of Ala in the natural tripeptide is substituted by another alkyl ester, inter alia ethyl ester, propyl or butyl ester, or the C-terminal Ala is amidated, preferably by protein conjugation, or with a polyethylene glycol moiety. According to a preferred embodiment, the C-terminal Ala is amidated with a polyethylene glycol (PEG) moiety. Such a PEG moiety has advantageously the formula —$(CH_2)_3$—$O(CH_2CH_2O)_2$—$(CH_2)_3NHCOCH_2OCH_2COOH$, such that the C-terminus of the tripeptide, tripeptide variant or tripeptide conjugate has the formula —$C(O)$—$NH$—$(CH_2)_3$—$O(CH_2CH_2O)_2$—$(CH_2)_3N\ HCOCH_2OCH_2COOH$.

Alternatively, or in addition to this modification at the C-terminus, the N-terminus of the Phe may also be modified by addition of a PEG moiety, which is the same or different from the PEG moiety potentially added at the C-terminus. A particularly preferred PEG moiety has the formula $X$—$(CH_2CH_2O)_n$—$CO$—$NH$ wherein X is an amine or alkyl moiety and n is an integer, preferably n is 1, 2, 3, 4 or 5.

A tripeptide, tripeptide variant or tripeptide conjugate according to this embodiment also, is able to specifically react with specific anti-Map antibodies, as detailed for the previous embodiments of the invention. The inventors have indeed demonstrated that the addition of the PEG moiety increases the hydrosolubility of the compound, without interfering with the ability of an oligopeptide to interact with specific antibodies, by showing in example 2, that the hydrosoluble analogue of L5P has the same immunogenicity as natural L5P; these results can be extended to the chemically related tripeptide, tripeptide variant and conjugate as disclosed.

Figure 9:
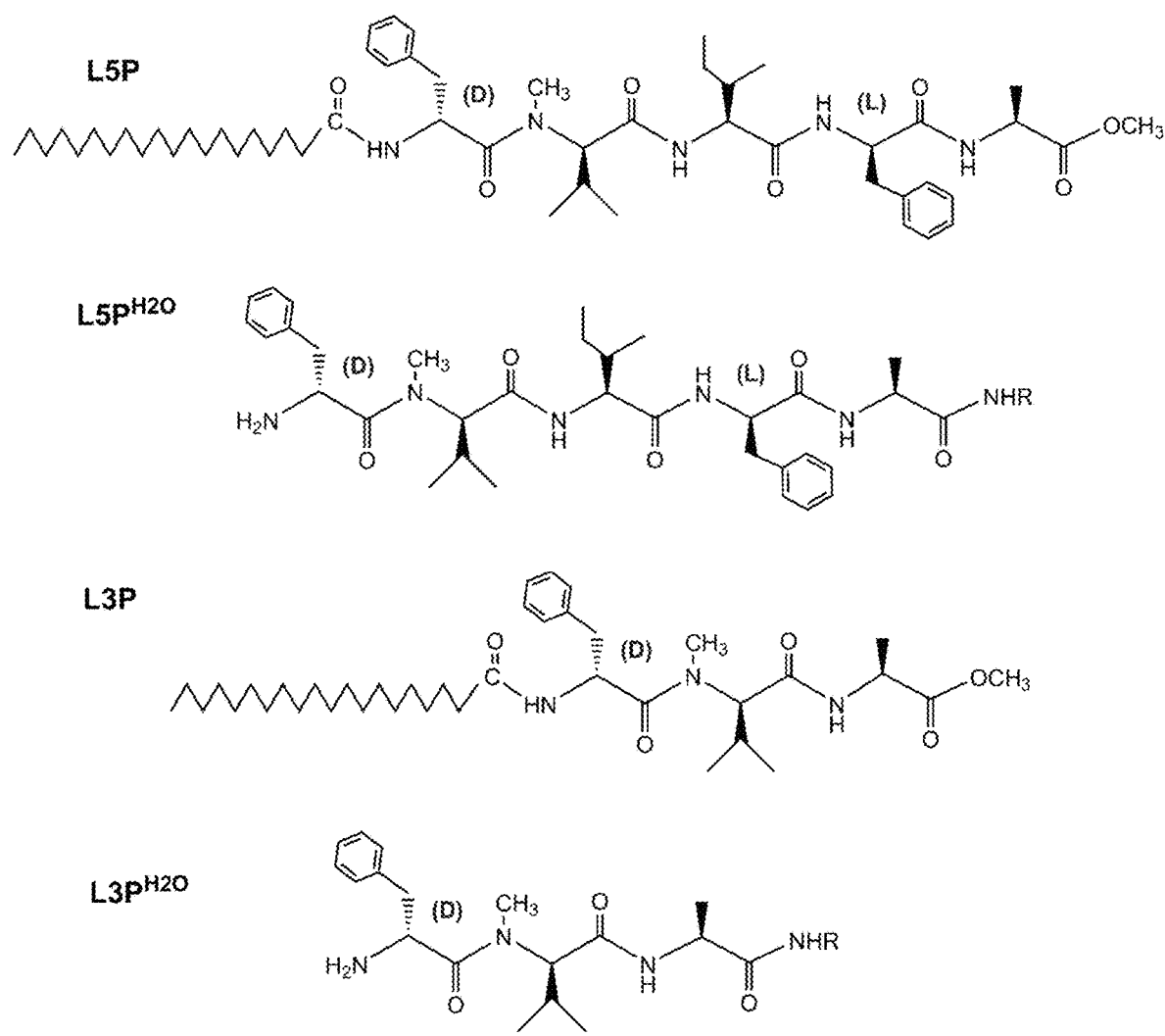

According to a more preferred embodiment, the invention is directed to a tripeptide, wherein the C-terminal Ala is amidated with a polyethylene glycol (PEG) moiety and wherein the $NH_2$ group of the N-terminal Phenylalanine is unmodified. Such a compound is illustrated in FIG. 9.

The different compounds of the invention, namely tripeptides, tripeptides variants and tripeptide conjugates can be prepared by conventional processes for synthesizing proteins, such as, for example, solid phase peptide synthesis, and classical chemistry.

If needed, the tripeptides or tripeptide variants can be labelled or coupled to a solid support. Labels and solid supports suitable for immunoassays, and methods for labelling peptides as well as for coupling them to said supports are well known to the skilled person.

According to a second aspect, the invention is directed to an antigen which is specific to *M. avium* subsp. *paratuberculosis* (Map) S-type, preferably for use in diagnosing Map infection in an animal. Such an antigen is to be chosen from the group consisting in a tripeptide or tripeptide variant of the invention, and a tripeptide conjugate of the invention, as detailed according to the first aspect of the invention. All the preferred embodiments detailed in the preceding section in connection with the first aspect of the invention are applicable to this second aspect of the invention.

The antigen of the invention is the first identified antigen which is specific to Map S-type, even if cross-reactivity with C-type is to be expected due to the close chemical structure of L3P and L5P. There is indeed no commercially available antigen specific to Map S-type. This new antigen, specific to S-type, has a thus high diagnostic value. In this respect, it is to be noted that the diagnosis of Map infection in sheep, carried out with the lipopentapeptide present in C-type, is insufficiently specific, as it gives a high number of undetermined results and false negatives (see inter alia FIG. 13).

The antigens of the invention are preferably to be used for diagnosis of Map infection in an animal susceptible to Map infection, preferably a mammal, most preferably in ovine or caprine animal.

The antigen is inter alia capable of discriminating between an infection by *M. avium* subsp. *paratuberculosis* (Map) S-type and infection by Maa or *M. bovis*.

According to a third aspect, the invention is moreover relative to different methods using the specificity and sensitivity of the new antigens of the invention, namely to methods for specifically detecting the presence of Map and/or quantifying Map, especially Map S-type in a sample, methods for diagnosing Map infection, especially Map S-type infection, methods for detecting humoral immune response and cell-mediated immune response against Map, especially Map S-type. The methods are advantageously used to detect, diagnose or quantify Map S-type in a subject prone to Map S-type infection.

In one embodiment, the invention is directed to a method for the detection of specific anti-Map antibodies, or for their quantification, in a sample, comprising contacting said sample with an antigen specific to Map. The antigen to be used in this method is an antigen as described above according to the second aspect of the invention, namely an antigen chosen from the group consisting in a tripeptide or tripeptide variant of the invention, and a tripeptide conjugate of the invention, according to the first aspect of the invention. The contacting step is to be carried out under conditions allowing the formation of an antigen-antibody complex with said antigen.

The method is preferably a method for the specific detection of antibodies against S-type strains of Map. The antigen used in the method is indeed based on the tripeptide Phe-Val-Ala, which is specific to the S-type of Map and not present in C-type Map or other mycobacteria. Due to the structure similarity between the S-type tripeptide and the C-type pentapeptide, it is however expected that the method detects both anti-Map S-type antibodies and anti-Map C-type antibodies, collectively referred to as "specific anti-Map antibodies", in the sample. In any case, the method allows to accurately detect anti-Map antibodies and to specifically detect anti-Map S-type antibodies.

The detection method is advantageously to be carried out ex vivo or even preferably in vitro.

According to this method, the detection of an antigen-antibody complex with the antigen of the invention is indicative of the presence of specific anti-Map antibodies and more preferably of anti-Map S-type antibodies. The antigen-antibody complex can further be quantified, in order to quantify the anti-Map antibodies, present in the sample. Such a quantification may be of importance, inter alia for differentiating animals at different stages of Map infection, e.g. for determining their infectivity level.

The method can be carried out simultaneously or sequentially with other antigens, either specific to other pathogens, for example in the context of a general sanitary control, or specific to Map C-type should it be necessary to discriminate between C-type and S-type strains. The antigen of the invention can advantageously be used in detection methods already known and inter alia in the methods disclosed in WO2009/053844.

The method of the invention can also be carried out with more than one antigen according to the invention, for example with two distinct antigens, e.g. at least one tripeptide or tripeptide variant of the invention, and at least one tripeptide conjugate, especially one lipotripeptide, namely a tripeptide conjugated to a fatty acid.

This method may also be carried out with a sample obtained from a human patient affected by Crohn's Disease, for example in order to decipher the link between Map and CD.

According to a further embodiment, the application is directed to a method for diagnosing Map infection in a subject, comprising contacting a sample obtained from said subject with an antigen according to the second aspect of the present invention.

According to this embodiment, the detection of an antigen-antibody complex with said antigen of the invention is indicative of Map infection or of a previous Map infection history, in the subject, i.e. indicative whether the subject has been infected by Map, provided that the subject has not been vaccinated against Map. This method is particularly suitable for detecting Map S-type infection, especially in animals more prone to S-type than C-type infection, like sheep and goats.

The method according to this aspect can discriminate between Map infection and *M. bovis* infection or *M. bovis* vaccination, in an animal. This feature is important, especially for cattle vaccinated against *M. bovis* infection.

The diagnostic method as described is particularly suitable for diagnosing Map infection in animals at early stages of infection, namely before the classical symptoms of Map infection arise, especially in sheep and goats. This diagnostic method may also be carried out in humans, with a view to study the link between infection by Map and CD occurrence.

As described above in the context of the detection methods, the diagnosis method of the invention can be carried out simultaneously or sequentially with additional distinct antigens, either specific to other pathogens, or specific to Map C-type. The antigen of the invention can moreover advantageously be added to the diagnosis methods already known and inter alia to the methods disclosed in WO2009/053844.

The method can also be carried out with more than one antigen according to the invention, for example with at least one tripeptide or tripeptide variant of the invention, and at least one tripeptide conjugate, especially one lipotripeptide, namely a tripeptide conjugated to a fatty acid.

According to a still further embodiment, the invention is also directed to a method for detecting humoral immune response directed against Map in a subject, comprising contacting a biological sample obtained from said subject with an antigen of the invention. This method of detecting humoral response is preferably carried out ex vivo or in vitro. The detection of an antigen-antibody complex with the antigen of the invention is indicative of humoral immune response directed against Map. The humoral response detected by this method may be either the result of Map infection, of a previous Map infection, or of Map vaccination.

This method is particularly suitable for detecting humoral immune response directed against Map S-type, especially in animals more prone to S-type than C-type infection, like sheep and goats, as the antigens is specific to Map S-type.

The method according to this aspect can discriminate between humoral immune response against Map and response against *M. bovis*.

The method as described is particularly suitable for detecting humoral immune response against Map infection in animal at early stages of infection, namely before the classical symptoms of Map infection arise, especially in sheep and goats.

As described above regarding the other methods of the invention, this method can be carried out simultaneously or sequentially with additional distinct antigens, either specific to other pathogens or specific to Map C-type. The method can also be carried out with more than one antigen according to the invention, for example with at least a tripeptide or tripeptide variant of the invention, and at least a tripeptide conjugate, especially a lipotripeptide, e.g.; a tripeptide conjugated to a fatty acid.

In the different methods of the invention as described, the detection of the antigen-antibody complex is preferably carried out by ELISA (enzyme-linked immunosorbent assay), by radioimmunoassay, electrophoresis, immunofluorescence or Western Blot. The antigen of the invention, used in the methods, thus advantageously comprises any tag or chemical group aiming at facilitating the detection of the antigen-antibody complex, for example a fluorophore or an enzymatic moiety.

For the different methods of the invention which are carried out on a sample, the sample may be any appropriate biological sample obtained inter alia from a subject, preferably from an animal and more preferably from a mammal. Appropriate sample are blood sample, serum sample, faeces sample, milk sample, lymph node biopsy, gut biopsy and urine sample. Other samples are inter alia biopsies of bowel tissues and tissue from bowel resection, especially in humans affected by Crohn's Disease. Particularly preferred samples are blood, serum, faeces and milk.

The different methods according to this third aspect of the invention are particularly advantageous in that they do not require any step of pre-adsorption of the sample with antigens of mycobacteria which are not *M. avium*, they especially do not require pre-adsorption step with antigens of *M. phlei*. The methods of the invention are thus preferably carried out without such pre-adsorption steps, as required by the commercially available diagnostic tests.

The diagnostic tests based on the host response and focused on detecting an antibody response have however some drawbacks. Early-diagnosis of MAP infection using serodiagnostic assays is sometimes hindered by the fact that affected animals can take a long time, to develop detectable serum antibody responses, at least using existing antigens. This drawback is partially overcome by the new antigens of the invention, which allow to detect serum antibody responses at an earlier stage than with previously existing antigens.

Moreover, other approaches for early diagnosis include the identification of MAP-specific antigens that detect cell mediated immune (CMI) responses such as the secretion of antigen-specific IFNγ or lymphocytes proliferation, elicited early after exposure to mycobacteria. The inventors have shown that the antigens based on the lipopeptide present in the envelope of Map are antigens that are also suitable to elicit cell mediated immune response. This point is illustrated in Holbert et al, 2015, with L5P and the results are expected to be also applicable to L3P, given the intrinsic nature of these compounds and their close chemical structure. As demonstrated in example 3 and FIG. 15, the CMI response, inter alia upregulation of T-cells proliferation, is even stronger with L3P than with L5P.

In another embodiment, the invention is thus also directed to a method for evaluating cell-mediated immune (CMI) response directed against Map in a subject, using the antigens of the invention. Preferably the cell-mediated immune response detected using the antigens of the invention is a T-cell response, and more preferably a CD25+ CD8 T cell response.

The antigen of the invention, as defined above, can indeed be used for evaluating in vitro or in vivo the T-cell immune response directed against Map, and especially against Map S-type. This can be done by the usual techniques for in vitro or in vivo detection of the cellular immune response.

For instance, a method for evaluating the T-cell immune response of a subject with respect to Map, especially Map S-type, is based on the detection of the activated T lymphocytes after incubation with the antigen of the invention, under conditions allowing the activation of the T lymphocytes present in a sample.

More specifically the invention is directed to a method for evaluating the CMI response directed against Map in a subject, comprising the steps of:
A) contacting a biological sample obtained from said subject with an antigen of the invention, and
B) detecting cytokine expression by the cells present in the biological sample or detecting lymphoproliferation.

The detection of cytokine expression or the detection of lymphoproliferation, depending on the nature of step B, is indicative of a cell immune response directed against Map in the subject.

This method of detecting CMI response is preferably carried out ex vivo or in vitro.

The method may also be carried out in vivo; in such an embodiment, the antigen of the invention is to be administered to the subject, and then the delayed-type hypersensitivity cell-mediated immune responses are detected by skin tests.

The method is particularly suitable for detecting CMI response directed against Map S-type, especially in animals more susceptible to S-type than C-type infection, like sheep and goats. As confirmed by the example 3, such a method however also allows detection of Map C-type infection. The method according to this aspect can discriminate between CMI response against Map and response against *M. bovis*.

The cytokine expression to be detected at step B) of the method is preferably IFNγ or IL-10, and more preferably IFNγ.

The sample to be used in carrying out this method is preferably as described above for the other methods of the invention. Particularly preferred samples are blood or PBMC isolated from blood.

In any of the methods disclosed above, the subject is preferably an animal more prone to Map S-type infection than Map C-type infection, especially an ovine or caprine animal, preferably sheep or goat. Given the link between Map infection and CD in human, the subject may also be a human, preferably a human affected by CD, or suspected to be infected by MAP.

As already detailed, the different methods according to the third aspect of the invention can be carried out simultaneously or sequentially with additional distinct antigens, either specific to other pathogens or specific to Map C-type, should it be necessary to discriminate between C-type and S-type strains. The methods can also be carried out with more than one antigen according to the invention, for example with at least one tripeptide or tripeptide variant of the invention, and at least one tripeptide conjugate, especially one lipotripeptide, namely a tripeptide conjugated to a fatty acid. The methods can also be carried out with at least one antigen according to the invention in combination with at least one antigen specific to C-type strains, such as a derivative or analogue of L5P as disclosed in WO2009/053844 or in the present invention, namely a hydrosoluble analogue of L5P.

All the methods as described can advantageously be carried out inter alia with samples obtained from non-symptomatic cattle.

According to a fourth aspect, the invention also concerns a composition comprising an antigen of the invention, thus specific to *M. avium* subsp. *paratuberculosis* (Map) S-type, for use as immunogenic composition. The immunogenic composition advantageously comprises additional components, in addition to the antigen of the invention. It may comprise adjuvants and/or pharmaceutically acceptable carriers. Suitable carriers are for example large macromolecules such as proteins, polysaccharides, amino acid copolymers, liposomes. Suitable adjuvants are inter alia aluminium salts, muramylpeptides, or CpG oligodeoxynucleotides. In a composition according to this aspect of the invention, the antigen to be used is preferably a tripeptide conjugate according to the $1^{st}$ aspect of the invention, specifically conjugated to a compound known to trigger an immune response.

An immunogenic composition may also comprise additional distinct antigens, either specific to other mycobacteria or to other pathogens, or different antigens according to the invention. For example, the immunogenic composition may comprise a tripeptide, tripeptide variant or tripeptide conjugate according to the invention, in combination with at least one further antigen, for example an antigen specific to Map C-type strains, inter alia the L5P tripeptide disclosed in WO2009/053844 or a variant or derivative thereof, or an hydrosoluble analogue of L5P as disclosed in a further aspect of the present invention. The immunogenic composition may also advantageously comprise different antigens according to the invention, e.g. at least two different, or at least 3, 4 or 5 different, for example one or more tripeptide or tripeptide variant and one or more tripeptide conjugate according to the invention.

Such an immunogenic composition may be useful for immunizing a subject against Map S-type infection, especially for vaccinating a subject against Map S-type infection. When the composition comprises a combination of an antigen of the invention with an antigen based on L5P, such a composition allows the vaccination of a subject against Map infection, irrespective of the Map strain. The immunizing composition according to the invention may also be used for generating an immune response in humans, with a view to preventing Crohn's Disease, especially for generating a protective immune response.

When used as a vaccine, the immunogenic composition of the invention is preferably used as a booster dose.

The invention thus also concerns a method for vaccinating a subject against infection by Map S-type, comprising administering to said subject an immunogenic composition as disclosed above. Such a vaccine is particularly appropriate for animals susceptible to Map S-type infection, and especially cattle, even more preferably ovine and caprine animals, such a sheep and goats.

According to still another aspect, the invention is also directed to a diagnostic kit for diagnosing *Mycobacterium avium* subsp. *paratuberculosis* (Map) infection in a subject, comprising an antigen according to the invention, and reagents for detecting an antigen-antibody complex.

Preferably such a kit also comprises controls, especially positive and negative controls, representative of presence and absence of Map infection. The diagnostic kit according to the invention is particularly suitable for diagnosing Map S-type infection, especially in animals more frequently infected by S-type than by C-type strains, especially ovine and caprine animals, such as sheep and goats. The kit may also comprise additional antigens, especially antigens specific to C-type strains, such as derivative or analogue of L5P as disclosed in WO2009/053844 or in the present invention, namely a hydrosoluble analogue of L5P. The kit may also comprise additional antigen specific to pathogens frequently infecting cattle, such as antigen specific to *M. bovis*.

Such a kit may for example be a dipstick diagnostic device.

According to still another aspect, the invention is also directed to different methods for detecting the presence of *M. avium* subsp. *paratuberculosis* (Map) S-type, or determining that a tested bacterium is Map S-type, by non-immunological methods.

The present inventors have indeed analyzed the msp1 gene of S-type and C-type strains, and have shown (see example 1) that there is a deletion of around 6.3 kb in the msp1 gene of S-type strain with respect to the corresponding gene of C-type strains. This genetic difference can advantageously be used to characterize a tested bacterium as a Map S-type, or to detect the presence of Map S-strain in a sample.

The invention is thus also directed to a method for genetically determining whether a tested bacterium is Map S-strain or for detecting the presence of Map S-strain in a sample, comprising:

a) amplifying the genomic DNA of the tested mycobacterium, or the DNA present in the sample, with the following primers:

```
forward primer P1
                               (SEQ ID NO: 10)
GTGCAGTACGCCGACTACAC
and reverse primer P3
                               (SEQ ID NO : 12)
ACCGGGAAAACAGCAGTG,
``` and
b) detecting an amplified product having a length of about 1112 bases.

The amplification step is preferably carried out by PCR. The detection is carried out by any appropriate method, well known to the skilled person. The length of the amplified product is preferably about 1112 bases, plus or minus 10%, namely between 1000 bases and 1224 bases. It cannot be excluded that an amplified fragment of a length of about 7.4 kb be obtained. The presence of such an amplified fragment, in the absence of a fragment of about 1112 bp, is not characterizing a Map S-strain, but rather a Map C-strain.

The sample is preferably a biological sample, especially a sample as disclosed according to the other aspects of the invention.

The invention also concerns a method for genetically discriminating between a *Mycobacterium avium* subsp. *paratuberculosis* (Map) C-type and S-type, comprising:

c) amplifying the genomic DNA of a mycobacterium with the following primers:

```
forward primer P1
                               (SEQ ID NO: 10)
GTGCAGTACGCCGACTACAC;

reverse primer P2:
                               (SEQ ID NO: 11)
AGAAACCGATCAGCTCGTCG
and reverse primer P3
                               (SEQ ID NO : 12)
ACCGGGAAAACAGCAGTG.
``` d) detecting an amplified product;
wherein an amplified product of a length of about 356 bases is indicative of C-type and an amplified product of a length of about 1112 bases is indicative of S-type. The length of the amplified product characterizing the C-type strain is 356 bases, plus or minus 10%, namely between 320 bases and 392 bases.

The inventors have also demonstrated that, by analyzing a biological sample by mass spectrometry or by NMR, the presence of the lipotripeptide L3P consisting in the tripeptide H-D-Phe-N-Methyl-L-Val-L-Ala-OMe (SEQ ID NO:1), wherein the N-terminal Phenylalanine is N-acylated with an eicosanoic acid acyl chain, which is indicative of the presence of Map S-strain, gives rise to a signal characteristic of said L3P; for example a peak at a mass-to-charge ratio (m/z) of 680 atomic mass units (amu), together with extra peaks differing by 14 amu (i.e. one methylene unit) assigned to variable lengths of the fatty acid moiety, when the sample is analyzed by mass spectrometry, especially MALDI-TOF.

Such peaks are not present in sample comprising only C-type, and more generally in samples not comprising Map S-type (FIG. 1).

The invention is thus also directed to a method for detecting the presence of Map S-strain in a sample, comprising:

e) analyzing by mass spectrometry the sample, e.g. by MALDI-TOF;
f) detecting a peak at a mass-to-charge ratio (m/z) of 680 atomic mass units (amu) and potentially also peaks differing by 14 amu, inter alia 694 amu and/or 708 amu, which are as intense as 680 amu.

The detection of such a peak or peaks allows to conclude that the sample comprises Map S-type envelope, and thus is indicative of Map S-type presence or infection.

The mass spectrometry is preferably MALDI-TOF.

The sample to be used is preferably a biological sample, especially a biological sample as detailed previously. A particularly preferred biological sample according to this embodiment of the invention is a sample from lymph nodes.

When lymph nodes are used, a suitable protocol is the following: the lymph nodes frozen at −20° C. are incubated in liquid nitrogen and crushed in a mortar (diameter 15 cm) with a pestle until a fine powder is obtained. The powder thus obtained is transferred with liquid nitrogen into a 50 mL tube. The tube is then set to −20° C., unclogged, while the nitrogen evaporates and then sent under cold conditions to lipid chloroform extraction then and treated to mass analysis.

By way of contrast, the detection of a peak of 940 amu is indicative of the presence of Map C-type in the sample. The method as disclosed thus allows the rapid and specific detection of Map S-type infection, and also allows to discriminate between S-type and C-type infections.

The inventors have also demonstrated, using NMR spectroscopy, the presence of L3P in a biological sample. Indeed $^1$H-NMR spectra of purified native and synthetic L3P show similar profiles with the typical signals for L3P, including peak multiplicities, coupling constants and chemical shifts (FIG. 7).

Figures 7A, 7B, 7C:
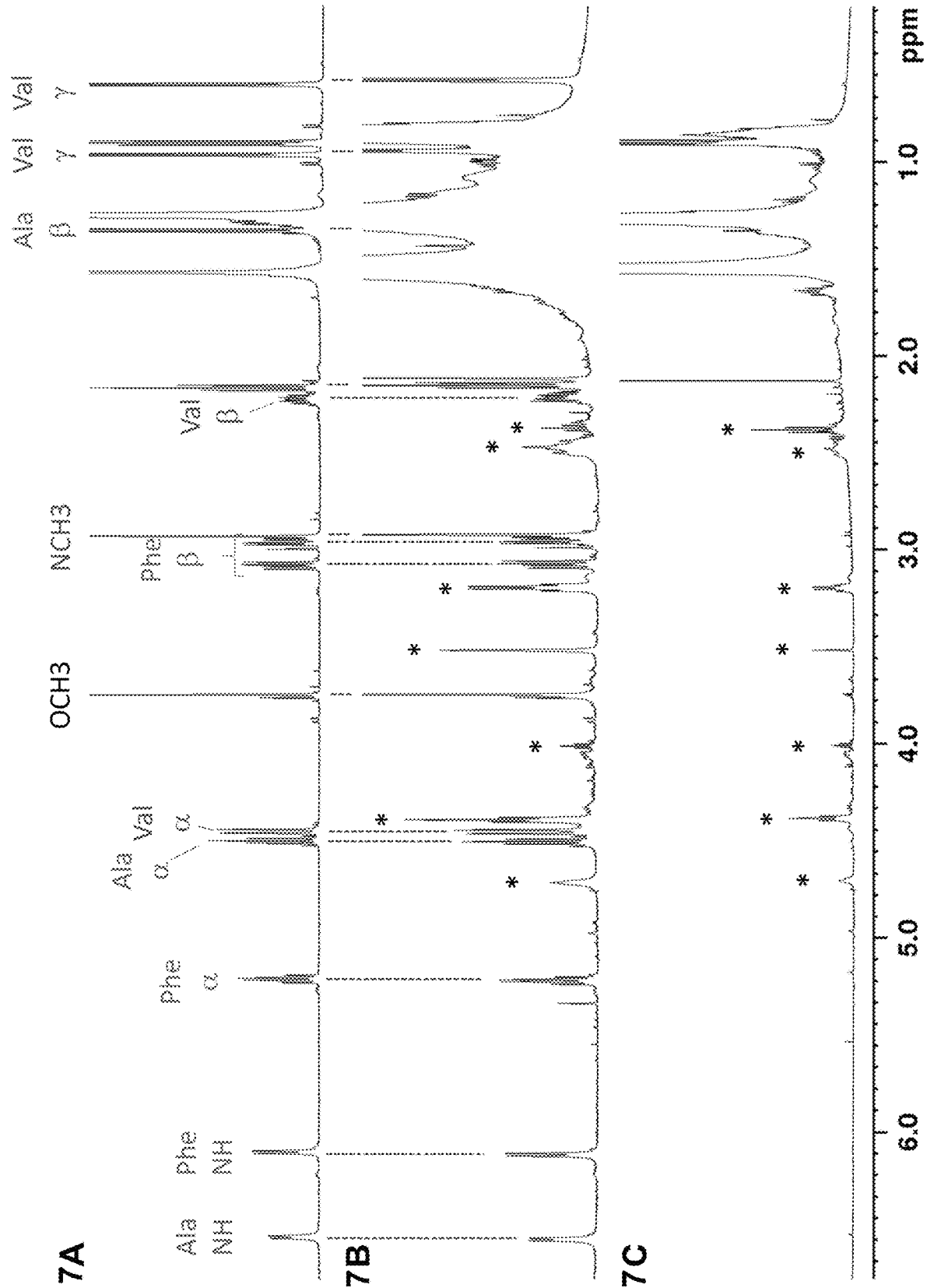

The invention is thus also directed to a method for detecting the presence of Map S-strain in a sample, comprising:

analyzing by NMR spectroscopy the sample;
detecting the typical signals of L3P as depicted in FIG. 7A, especially the main peaks as depicted in FIG. 7A.

The present inventors have also identified specific modifications of the lipopeptides of *M. avium* subsp. *paratuberculosis*, namely of the lipopentapeptide of C-strains and of the lipotripeptide of S-strains, greatly enhancing the hydrosolubility of these lipopeptides. These lipopeptides are indeed naturally not hydrosoluble, but soluble in methanol or ethanol. These solvents may prove to be difficult to manipulate, especially with a view to developing rapid and easy-to-use diagnosis kits, which can be performed by veterinarians or producers without expensive laboratory equipment.

Accordingly, the invention is also directed to a pentapeptide conjugate comprising a pentapeptide core having the sequence H-Phe-Val-Ile-Phe-Ala-OH (SEQ ID NO:13), wherein the 5 amino acids are independently natural amino acids or modified amino acids, either D or L amino acids, and wherein the pentapeptide core is further modified by one or more of the following modifications:
- g) the C-terminal Alanine is amidated with a polyethylene glycol (PEG) moiety;
- h) the C-terminal Alanine is amidated with a PEG moiety and the N-terminal Phenylalanine is N acylated;
- i) the N terminal Phenylalanine is modified by addition of a PEG moiety;
- j) the C-terminal Alanine is amidated with a PEG moiety and the N-terminal Phenylalanine is modified by addition of a PEG moiety, which is identical or different to the C-terminal PEG moiety.

The pentapeptide core may advantageously have the H-D-Phe-N-Methyl-L-Val-L-Ala-O-Me (SEQ ID NO:14) and the modifications disclosed above. Such a lipopentapeptide analogue is illustrated in FIG. 9.

A particularly preferred PEG moiety according to this aspect of the invention is the PEG moiety having the formula $(CH_2)_3—O(CH_2CH_2O)_2—(CH_2)_3NHCOCH_2OCH_2COOH$.

The pentapeptide conjugates as disclosed above are hydrosoluble analogues of the lipopentapeptide disclosed in WO2009/053844. They can be used in the different diagnosis and detection methods disclosed in WO2009/053844, in place of the synthetic lipopentapeptide, which is not hydrosoluble. The pentapeptide analogues of the invention are thus advantageously used in methods for diagnosing Map infection in a subject, preferably Map C-type infection. They can also be used in the different methods disclosed in the present invention, in combination with a tripeptide, tripeptide variant or conjugate according to the invention, for example in methods aiming at discriminating C-type strains and S-type strains.

The tripeptide conjugates comprising the same modifications as detailed above for the pentapeptide conjugate, and having as peptidyl core the tripeptide according to the invention, are also within the scope of the invention.

The present invention will be further illustrated by the experimental section which follows, which refers to the identification of L3P and its study, including its specific reactivity with anti-Map antibodies, as well as the design of hydrosoluble analogues of the lipopeptide L5P. These examples are given only by way of illustration of the invention and do not constitute in any way a limitation thereof.

LEGEND OF THE FIGURES

FIG. 1A-D: Mass spectrometry analysis of the lipids from Map. MALDI-TOF spectra of chloroform/methanol-extracted lipids from C-type Map K-10 (A), S-type Map S397 (B), purified native L3P (C) and synthetic L3P (D). The peak at 940 amu corresponds to L5P in the lipid extract of the C-type strain K-10, but is absent from the native lipids extracted from S397. The peak at 680 amu corresponds to the L3P.

Figure 2C:
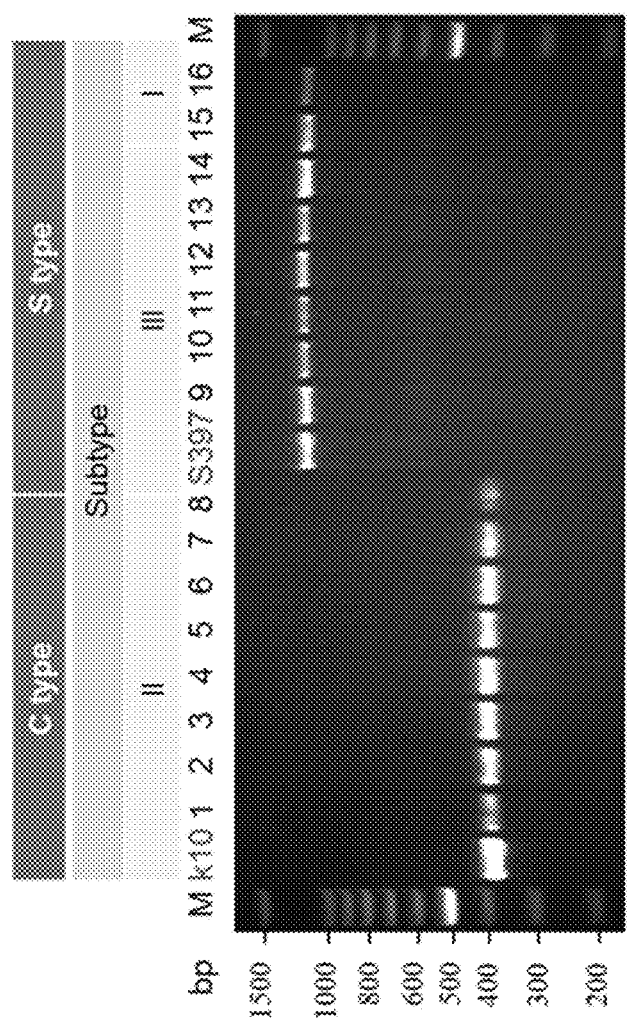
Figure 2B:
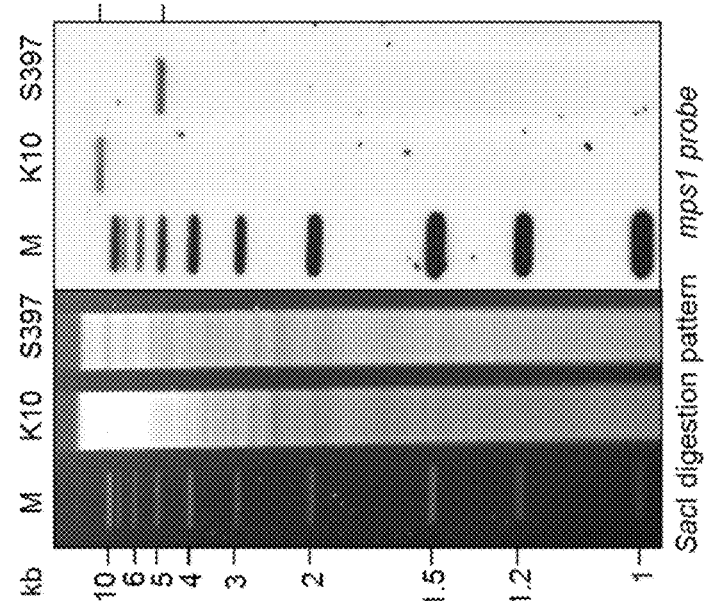

FIG. 2A-C: DNA analysis of the mps1 deletion in the S-type strains. (A) Schematic illustration showing the mps1 coding region in K-10 and S397. The larger arrow indicates the mps1 coding sequence with the SacI sites and primer binding locations shown. The asterisk shows the location of the labeled probe used in the experiment. The shaded area represents the 6.3 kb segment that is present uniquely in the K-10 strain. The same primers were used for the experiment in panel C. (B) Agarose gel and Southern blot of SacI-digested genomic DNAs. The right half of panel B shows the respective sizes of the SacI fragment after hybridization with the labeled probe. Molecular size standards (M) are indicated in kilobase pairs in the left margin. The K-10 fragment is over 10 kb and the S397 fragment is approximately 6.5 kb. (C) Amplification products from a panel of C- and S-type Map DNAs using a three-primer amplification approach where P1 is the forward primer and P2 and P3 are the reverse primers used in a single reaction. The primers were designed such that the resulting PCR products would be of different sizes depending on the presence or absence of the $LSP^{mps1}$. This experiment was performed using a collection of 18 C-type and S-type strains previously characterized and genotyped (Biet et al., 2012). See Table 1 for details about these strains.

Figure 3:
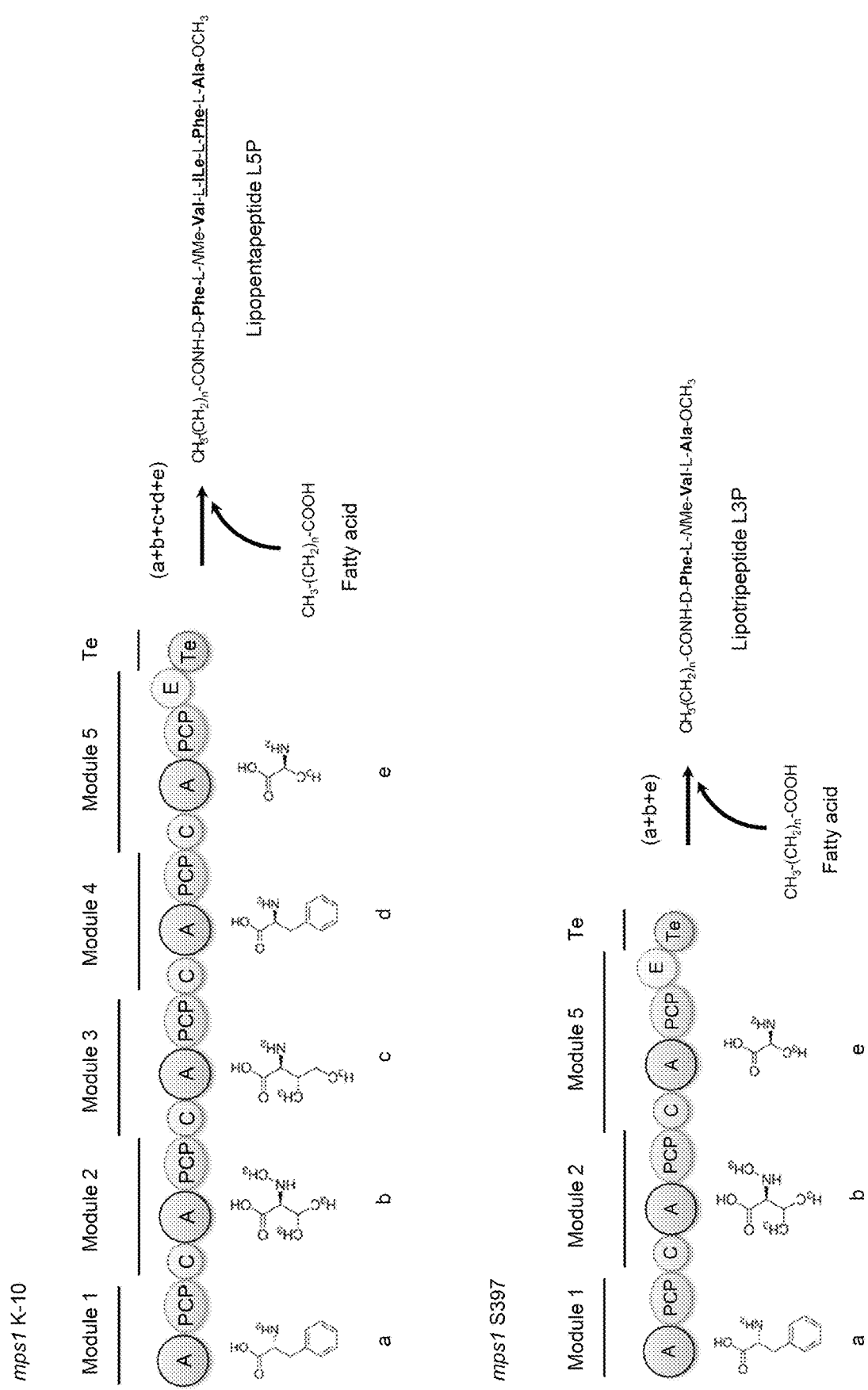

FIG. 3: Proposed model for NRP assembly of L3P and L5P in Map. Shown are the modules and domains predicted for Mps1 in K-10 and S397. Based on comparative sequence analysis, modules 3 and 4 are predicted to be absent in S397. When the 3- and 5-amino acid peptide moieties are combined with the fatty acid (n=18-20), the lipopeptide emerges. The underlined amino acids in L5P are missing in L3P. C=condensation domain; A=adenylation domain; PCP=peptidyl carrier domain; E=epimerisation domain and Te=thioesterase domain to release the full-length peptide chain.

FIG. 4A-B: S-type Map contains L3P. (A) 2-D TLC of total S397 lipids (500 µg spotted), using chloroform/methanol (96:4) as first dimension and toluene/acetone (80:20) as second dimension, and chemically synthesized L3P (15 µg) as a marker (black arrows). The asterisk indicates the position of native L3P. (B) 1-D TLC of the purified native L3P (line 3), compared to the synthetic controls L5P (line 1) and L3P (line 5) using chloroform/methanol (95:5) as the solvent system. The samples are also loaded as mixtures of the adjacent spots: synthetic L5P and purified native L3P (line 2), purified native L3P and synthetic L3P (line 4). The TLC plates were sprayed with 10% copper sulfate in 8% phosphoric acid, and lipids were visualized by heating.

FIG. 5: Tandem MS spectra of purified native and synthetic L3P show identical fragmentation patterns. L3P purified from S397 lipids was analyzed by MALDI-TOF MS/MS and compared to synthetic L3P and LSP. Structure of L3P and typical fragmentation at the Phe-N-Methyl-Val bond. Table 2 reports the ions originating from the fragmentation at the Phe-N-Methyl-Val bond.

FIG. 6A-E: Alignment of Mps1 sequences from Map K-10 and S397. The amino acid sequences of Mps1 of K-10 (SEQ ID No: 16) was aligned with its homologue in S397 (SEQ ID No:17) by using the NCBI BLAST program with the BLOSUM64 matrix allowing gaps, Gap Costs: Existence: 11 Extension: 1, Compositional adjustments: Conditional compositional score matrix adjustment. The sequence corresponding to the LSP not present in S397, amino acids 179 to 5289 (underlined), was excluded.

The alignment statistics give 98% of identities (4175/4275), 98% of positives (4218/4275) and 0.7% of gaps (3/4275).

FIG. 7A-C: $^1$H-NMR spectra of purified native and synthetic L3P show similar profiles. Synthetic L3P (A) and native L3P purified by preparative 2-D TLC (B) were analyzed by ¹H-NMR and compared to a contaminant compound (C) which partially co-eluted with the native L3P (typical extra peaks indicated with an asterix).

FIG. 8A-D: The native S397 L3P and the native K-10 L5P are cell surface-exposed. MALDI-TOF spectra of cell bound (A and C) and cell surface-exposed (B and D) lipids from C-type Map K-10 (A and B), and S-type Map S397 (C and D). The peak at 940 amu corresponds to L5P in the lipid extracts of the C-type strain K-10 and the peak at 680 amu to the L3P in S-type strain S397.

FIG. 9: Structures of the lipopeptides L5P and L3P identified in *M. avium* ssp. *paratuberculosis* (Map) and of their respective L5P hydrosoluble analogues L5P$^{H2O}$, and L3P$^{H2O}$ (R=(CH$_2$)$_3$—O(CH$_2$CH$_2$O)$_2$—(CH$_2$)$_3$NHCOCH$_2$OCH$_2$COOH).

Figure 10:
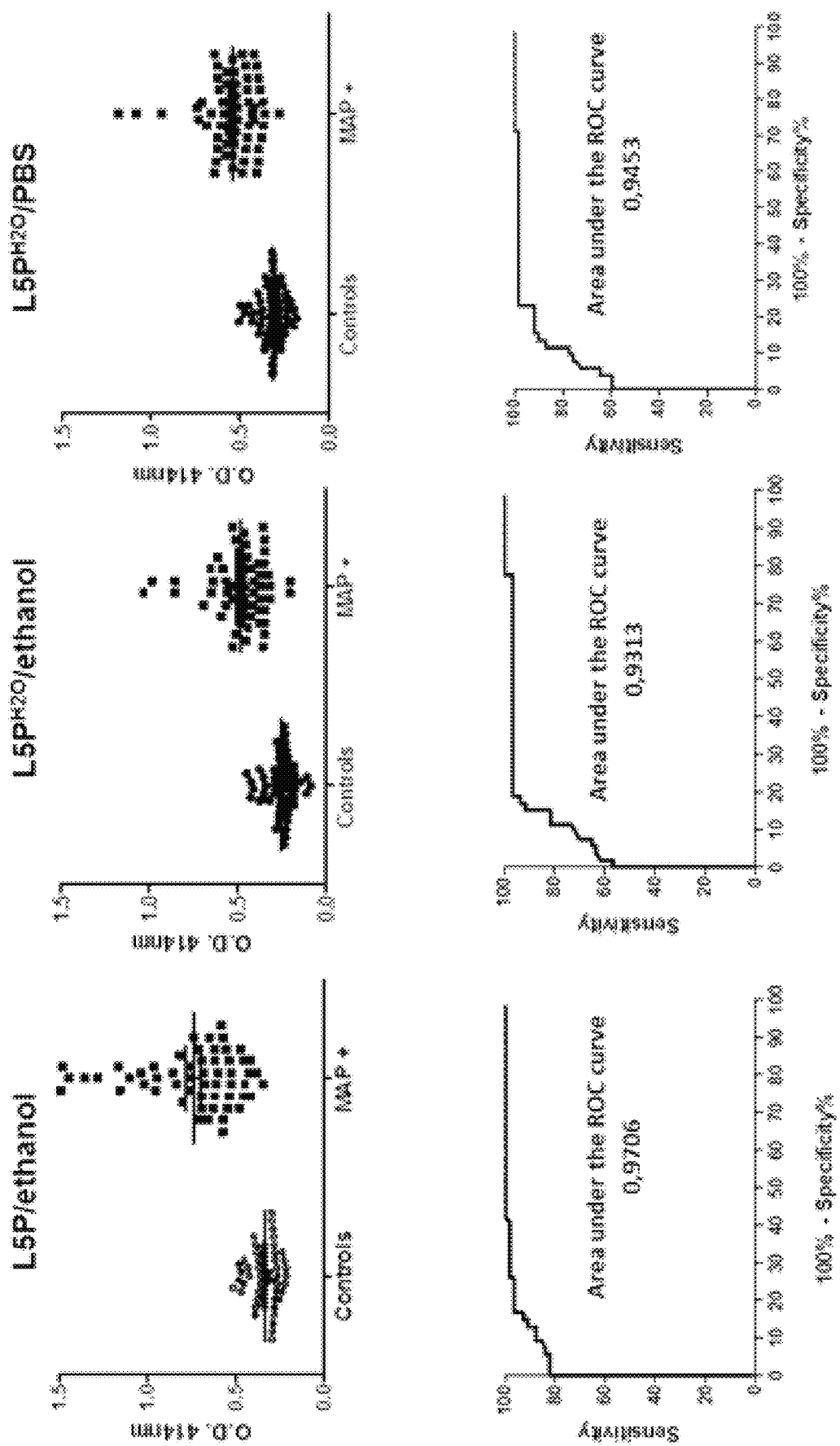

FIG. 10: Receiver operating characteristic (ROC) analysis of detection by ELISA of the antibody response against the L5P and L5P$^{H2O}$ using bovine sera. L5P is hydrophobic and solubilized in ethanol, and L5P$^{H2O}$ was used in ethanol or in PBS.

MAP+: Sera from bovine infected by Map and 53; Controls: sera from healthy bovine FIG. 11: ROC analysis of detection by ELISA of the antibody response against the lipid moiety of L5P using bovine sera. The lipid (eicosanoic acid) is hydrophobic and solubilized in ethanol.

Figure 12:
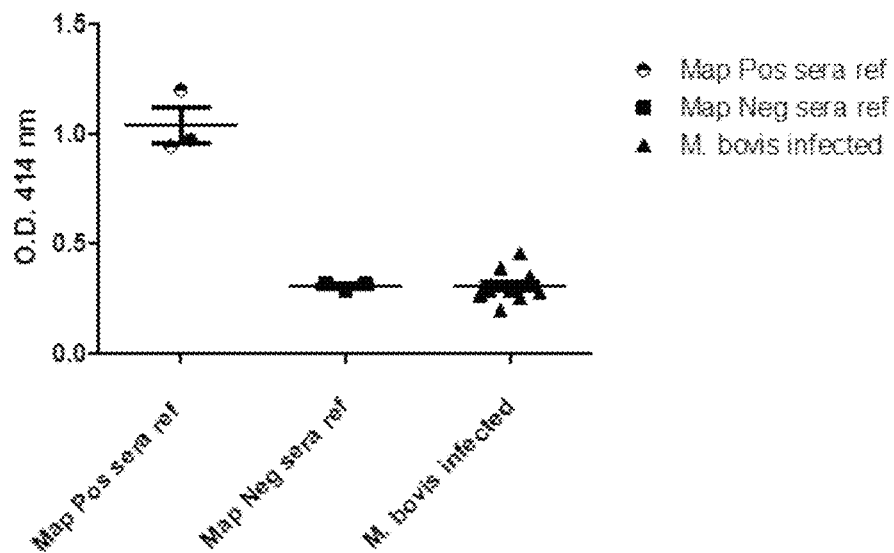

FIG. 12: Recognition of the L5P by sera of Map-infected bovines compared to *M. bovis*-infected bovines and Map-negative controls. The ELISA was performed with serial twofold dilution of reactive sera and the results are expressed as the means of triplicates.

Figure 13:
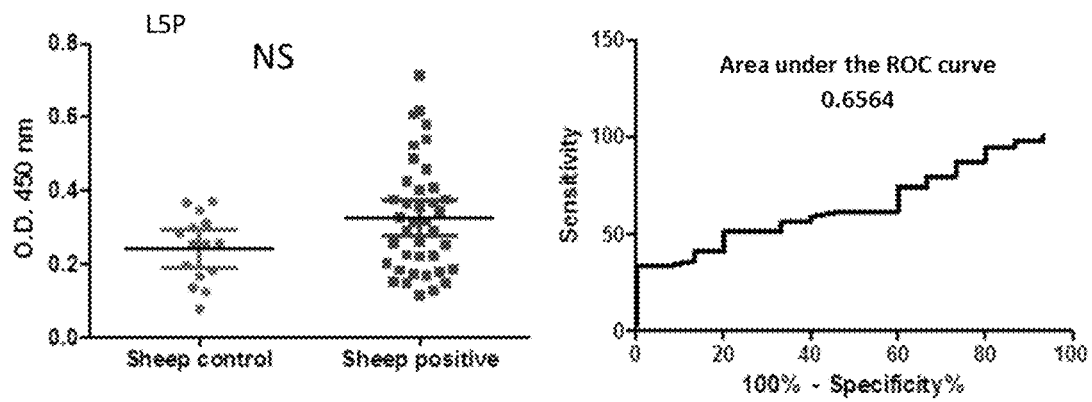

FIG. 13: Immunodetection of L5P by sheep sera naturally or experimentally infected with S-type strains of Map. (Control n=15, positive n=39)

Figure 14:
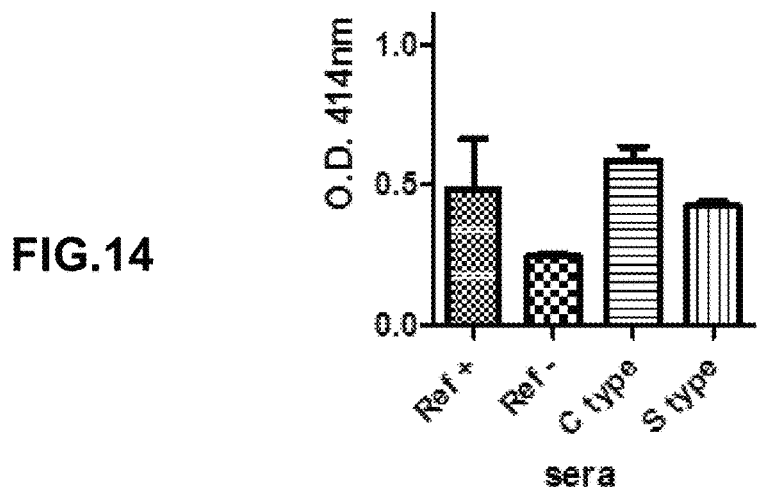

FIG. 14: ELISA recognition of L3P by bovine or sheep sera (n=3) naturally infected with C- or S-type strains of Map, respectively. Ref+; reference bovine positive serum to Map (n=3). Ref-; reference bovine negative serum to Map (n=3).

Figure 15A:
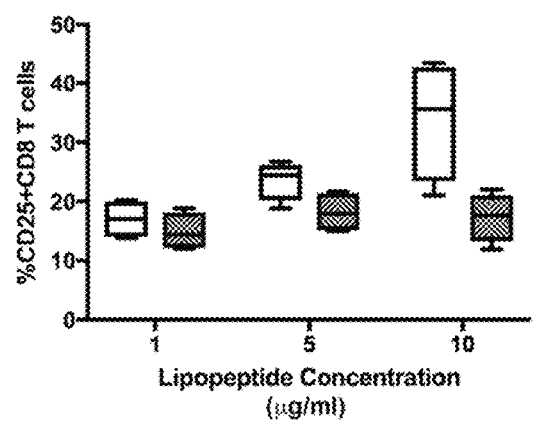
Figure 15B:
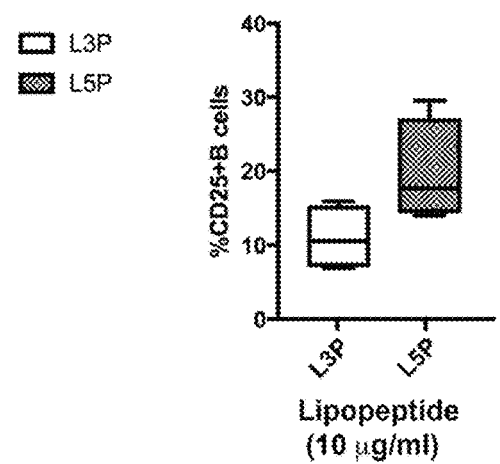

FIGS. 15A-B: T cell and B cell response to the Map lipopeptides. Proliferation of CD25+ T cells (FIG. 15A) and B cells (FIG. 15B) after culture of PBMCs isolated from cows naturally infected with Map and exposed to lipopeptides. Results are presented as percentage of CD25+ T or B cells (mean±SEM).

Figure 16:
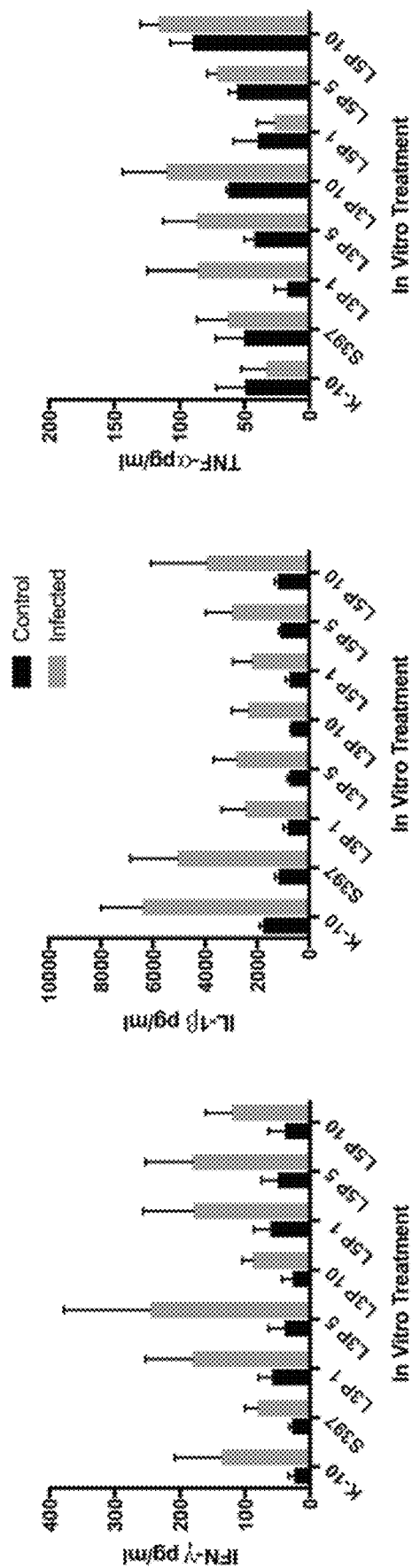

FIG. 16: Cytokine secretion by PBMCs after 24-hour stimulation with Map lipopeptides. Shown are cytokines measurements on PBMCs isolated from control cows and cows naturally infected with Map. Results are expressed as picograms/ml for IFN-γ (left), IL-1β (middle) and TNF-α (right) after stimulation with either bovine (K-10) or ovine (S397) strains of Map or lipopeptides L3P and L5P (1 µg/ml (1); 5 µg/ml (5); 10 µg/ml (10)). Histogram bars represent the mean with error bars indicating the SEM.

EXAMPLES

Example 1: Identification of Cell Wall Peptidolipid of *M. avium* Subsp. *paratuberculosis* (Map) Ovine Strain (S-Type)

Mycobacteria have a complex cell wall structure that includes many lipids; however, even within a single subspecies of *Mycobacterium avium* these lipids can differ. Total lipids from an *M. avium* subsp. *paratuberculosis* (Map) ovine strain (S-type) contained no identifiable glycopeptidolipids or lipopentapeptide, yet both lipids are present in other *M. avium* subspecies. The inventors determined the genetic and phenotypic basis for this difference using sequence analysis as well as biochemical and physicochemical approaches. This strategy showed that a nonribosomal peptide synthase, encoded by mps1, contains three amino acid specifying modules in all ovine strains analyzed, compared to five modules in bovine strains (C-type). Sequence analysis predicted these modules would produce the tripeptide Phe-N-Methyl-Val-Ala with a lipid moiety, termed lipotripeptide (L3P). Comprehensive physicochemical analysis of Map S397 extracts confirmed the structural formula of the native L3P as D-Phe-N-Methyl-L-Val-L-Ala-OMe attached in N-ter to a 20-carbon fatty acid chain. These data demonstrate that Map S-type strains, which are more adapted in sheep, produce a unique lipid. Implications for these lipid differences may include patho-evolution toward host specificity and disease presentation.

Introduction:

Map is considered as a genetically homogenous subspecies of *M. avium*, especially among bovine, human and wildlife isolates (Wu et al., 2006). However, two primary lineages have emerged following extensive phylogenetic analyses and comparative genomic studies (Biet et al., 2012). These lineages are classified as type I/III or S-type (ovine) and type II or C-type (bovine) strains. Map appears to have emerged from the common ancestor, *M. avium* subsp. *hominissuis*, to yield these two lineages. The Map C-type was first isolated from cattle and is the most commonly isolated type, while the Map S-type are typically isolated from sheep and are less prevalent. The S-type isolates are readily distinguishable from C-type isolates based on genome sequencing studies (Li et al., 2005, Bannantine et al., 2012). But these two lineages can also be readily discriminated by genotyping methods due to single nucleotide polymorphisms (Marsh et al., 1999) as well as deletions/insertions of large DNA segments (termed large sequence polymorphisms or LSP) using phylogenetic techniques such as variable number tandem repeats (Lefrancois et al., 2013), single sequence repeats (Amonsin et al., 2004, Thibault et al., 2008), representational difference analysis (Dohmann et al., 2003) and hsp65 sequencing (Turenne et al., 2006). Furthermore, genomic hybridization of S-type strains on a C-type microarray revealed a large 23-gene deletion in S-type strains (Marsh et al., 2006). However, in no case has a genetic difference been linked to a phenotypic difference between C- and S-type strains, until this study.

In addition to the genotypic distinctions between S- and C-type strains, phenotypic differences involving growth characteristics have been noted since the middle of the last century. The S-type strains are more fastidious and have slower growth rates in laboratory media than C-type strains. In contrast to C-type, the S-type strains do not grow readily on Herold's egg yolk media or Middlebrook 7H9 media that is not supplemented with egg yolk (Whittington et al., 2011). Nutrient limitation will kill S-type strains but it is only bacteriostatic for C-type (Gumber et al., 2009). Motiwala and coworkers have shown transcriptional changes in human macrophages infected with C-type, human and bison isolates, which induce an anti-inflammatory gene expression pattern, while the Map S-type isolates showed expression of pro-inflammatory cytokines (Motiwala et al., 2006), (Stevenson et al., 2002, Biet et al., 2012). Furthermore, many of the S-type strains are pigmented while C-type strains are not. On the transcriptional level, C- and S-type strains exposed to low iron or heat stress conditions had different mRNA expression patterns (Gumber & Whittington, 2009). Furthermore, iron storage in low iron conditions was only observed in the C-type but not S-type strains (Janagama et al., 2009) and virulence adhesin differences were characterized (Lefrancois et al., 2013). In this study, differences in a lipopeptide that is a component of the mycobacterial cell envelope were identified between C- and S-type strains.

Non-ribosomally synthesized peptides include a diverse class of important metabolites such as antibiotics. Nonribosomal peptides (NRP) are usually 3-10 amino acids in length and are synthesized by large multi-modular enzymes called non-ribosomal-peptide synthetases (NRPSs). These peptides are not assembled by ribosome, but rather are RNA template and ribosomal independent to allow for maximum biological flexibility by incorporating many unique amino acids. Although 10% of bacterial NRPS genes are non-modular (Wang et al., 2014), most have a modular organization where each module specifies the sequential addition of an amino acid. Several kilobases of DNA are needed for each module that consists of three domains termed the adenylation domain, peptidyl carrier domain and condensation domain. The adenylation domain binds ATP, selects its cognate amino acid building block and performs substrate acyl adenylation. Amino acid translocation occurs with the peptidyl carrier domain. The largest NRPS yet discovered is from *Photorhabdus luminescens* (WP_011146892; 16,367 aa) and contains 15 modules (Wang et al., 2014). This may represent the upper limit of NRPSs. In Map the mps1 gene encodes a NRPS with five modules that have been previously shown to be involved in production of the pentapeptidic moiety of the lipopentapeptide (L5P) (Biet et al., 2008).

The objective of this study was to identify the composition of lipopeptides in the S-type strains of Map and determine if they are different from the C-type strains.

Genetic characterization allowed the inventors to predict the production of different lipopeptide components, depending on the strain type. Synthesis of the predicted S-type lipopeptide together with thorough biochemical and physico-chemical analyses demonstrated that typical lipopeptides from Map are different in S-type (lipotripeptide) and C-type strains (lipopentapeptide). Overall, the inventors reveal key elements of Map cell wall change, involving genes and lipopeptides, occurring on the patho-evolution of the subspecies *paratuberculosis*.

Results:

The lipid composition differs between C- and S-type strains of Map. A panel of genetically diverse Map strains isolated from different animal species appears similar in their lipid profiles when analyzed by thin layer chromatography (TLC) in a single dimension (1-D) (Biet et al., 2008). However, the analysis of extracted lipids from both the S397 and K-10 Map (sequenced strains characteristic of S- and C-type, respectively) revealed a striking difference by Matrix-Assisted Laser Desorption Ionization-Time Of Flight Mass Spectrometry (MALDI-TOF MS). Only the C-type strain showed a major peak at a mass-to-charge ratio (m/z) of 940 atomic mass units (amu) (FIG. 1A), which corresponds to the [M+Na]$^+$ ion of the previously characterized L5P (Riviere et al., 1996). Additional minor peaks were also observed differing by 14 amu (including a peak at m/z 968 amu), all of which are present uniquely in the C-type strain, and assigned to variable lengths of the fatty acid moiety of the L5P (Biet et al., 2008, Eckstein et al., 2006). Instead of the ion peaks at m/z 940±14 amu, the extracted lipids from the S397 strain show three major peaks at 680, 694 and 708 amu (FIG. 1B). The rest of the MS spectra were nearly identical between the two strains. These data indicate that the lipid composition of the S397 sheep strain is different from that of the C-type strains and does not include the L5P molecule.

The mps1 gene is different between C- and S-type strains. A comparative genomic study was performed to determine the genetic basis for the absence of L5P in S397. While approximately 28 genes are necessary for GPL biosynthesis (Ripoll et al., 2007), the peptide core of L5P in Map is assembled by the product of a single nrps gene, termed mps1 (Biet et al., 2008). The mps1 gene of Map K-10 is also known by the locus tag MAP_1420 and has a size of 19.15 kb encoding 6,384 amino acids (Li et al., 2005). This gene is under the control of the LuxR regulator and has shown increased transcription when exposed to cow's milk (Alonso-Hearn et al., 2010). It has been suggested that the pentapeptide moiety is non-ribosomally assembled by the modules encoded in this gene (Eckstein et al., 2006), therefore, it was of interest to examine the homolog in the S-type strain. However, previous de novo whole genome assemblies of the Map S397 genome using the available Roche GS20, Roche FLX (i.e. 454), and Sanger sequence data (Bannantine et al., 2012) were unsuccessful at producing a complete assembly of the mps1 gene due to the large size and the presence of long, highly syntenic repeats in the amino-acid-specifying modules. Therefore two large sequence gaps were present in mps1 in the S-type genome.

While genome sequencing revealed that the mps1 gene is present in the S-type strain, the question of why that strain does not produce L5P remained unanswered. To address this, additional sequence data were obtained to completely assemble the region containing mps1 in the S397 genome. Surprisingly, the mps1 gene was only 12,822 bp in size compared to 19,148 bp in the K-10 genome, representing a difference of 6,326 bp. Southern blot analysis was used to confirm the 6.3 kb deletion (FIGS. 2A and 2B). By taking advantage of two SacI restriction sites that border the deletion (FIG. 2A), it was observed that the S397 SacI fragment was approximately 6 kb smaller than the corresponding fragment in K-10 (FIG. 2B).

The deletion was further characterized by PCR analysis and tested across multiple strains (Table 1). To verify that the difference in size of the mps1 gene is characteristic of all sheep strains, a PCR to detect this large sequence polymorphism (LSP$^{mps1}$) was developed based on the model described by Semret et al. (Semret et al., 2006). From the mps1 locus in K-10, three primers (P1, P2, and P3, forward primer P1 GTGCAGTACGCCGACTACAC (SEQ ID NO:10); reverse primer P2: AGAAACC-GATCAGCTCGTCG (SEQ ID NO:11) and reverse primer P3 ACCGGGAAAACAGCAGTG (SEQ ID NO:12) were designed and used in a single reaction to amplify DNA depending on the presence or absence of the 6.3 kb region (FIG. 2A). The primers were designed so that the size of the PCR product is different when using this 3-primer combination. The P1-P3 pair results in no amplification from C-type DNA due to the large distance between primers. However, P1-P2 results in successful amplification since they are only separated by 376 bp (FIG. 2C). Conversely, the P1-P2 primer combination does not work in S-type strains since P2 is located within the LSP$^{mps1}$ (FIG. 2A). However, P1-P3 does amplify S-type DNA because they are only separated by 1,112 bp due to the LSP$^{mps1}$ (FIG. 2C). Collectively, these results confirmed the boundaries of the deletion and showed it is consistent in all ten S-type strains tested including characteristic subtypes I and III.

TABLE 1

Source of strains or DNA used
and their genotyping characterization

| Strain ID | Host origin | Type Subtype | Country |
|---|---|---|---|
| K10 | Bovine | C II | USA |
| S397 | Ovine | S III | USA |
| 235G | Ovine | S I | UK, Shetland |
| M189 | Ovine | S I | UK, Scotland |
| 22G | Ovine | S III | ES, Basque |
| 269OV | Ovine | S III | ES, Basque |
| FO21 | Ovine | S III | ES, Aragon |
| OVICAP16 | Caprine | S III | ES, Andalucia |
| OVICAP34 | Ovine | S III | ES, Basque |
| OVICAP49 | Ovine | S III | ES, Navarra |
| PCR311 | Caprine | S III | ES, Balearic |
| 13 | Bovine | C II | France |
| 20 | Bovine | C II | France |
| 47 | Bovine | C II | France |
| 54 | Bovine | C II | France |
| 64 | Bovine | C II | France |
| 85 | Bovine | C II | France |
| 104 | Bovine | C II | France |

NRPS encoded by mps1 is missing modular domains in the S-type strains. The NRPS of mps1 is modular in its organization such that each module specifies the incorporation of one amino acid in the peptidic moiety of the lipopeptide. It became of interest to examine how the LSP$^{mps1}$ deletion might have affected lipopeptide production in the S-type strains. Using bioinformatics (Rottig et al., 2011), the functional modules and domains within each module of the NRPS were identified and this analysis established that the S-type NRPS is composed of 3 modules while the C-type has 5 modules. Furthermore, these analyses have established the nature and the position of the NRPS domains in S-type along with the domains present in C-type but missing in the S-type strain (FIG. 3). Comparison of the protein sequences corresponding to the three domains of Mps1 present in both strains shows a perfect homology suggesting a same functionality in terms of amino acid assembly (see FIG. 6).

Altogether, the sequence analysis and bioinformatic predictions of NRPS module composition identified the tripeptide Phe-Val-Ala as the antigen backbone. By analogy with the known L5P, the inventors therefore predicted that the S397 strain produces a lipotripeptide, named L3P, bearing the same structural formula as L5P but missing the two amino-acids L-Ile and L-Phe (FIG. 3).

S-Type Strains Produce a Lipid Antigen Identical to the Synthetic Lipotripeptide L3P.

To determine if S-type Map effectively produces this novel L3P antigen, the L3P molecule was chemically synthesized and compared with the native source of lipid (either the crude or the purified lipid extract from S397).

The synthetic L3P was obtained by solid-phase peptide synthesis using Fmoc chemistry and purified by chromatography on silica gel. It was then used as a control in a series of physico-chemical comparative analyses to formally identify the S-type lipid antigen.

Analysis and Purification by TLC

The analytical 2-dimensional (2-D) TLC of S397 lipid extracts shows a spot, not as prominent as L5P in C-type strains, co-migrating with the synthetic L3P (FIG. 4A). After loading a preparative 2-D TLC with 7 mg of crude extract obtained from 317 mg of cells (dry weight), the spot of interest was purified by scraping the silica gel and subsequent elution in $CH_2Cl_2$/methanol 95:5 (vol/vol). The resulting purified native antigen (approximately 50 µg) is clearly different from the C-type Map L5P, and it co-migrates with the synthetic L3P, as shown by the 1-D TLC (FIG. 4B).

Analysis by MALDI-TOF MS and MS/MS

The peak of the synthetic L3P at m/z 680 amu ([M+Na]$^+$ ion) matches that of the native antigen from the S397 strain, whether in the crude extract or in the purified lipids (FIGS. 1B, 1C and 1D). The extra peaks differing by 14 amu (i.e. one methylene unit) observed for the native antigen (FIGS. 1B and 1C) suggest the presence of different fatty acid chain lengths. In particular, the compound at m/z 708, which co-elutes with the L3P in 2-D TLC, may correspond to the L3P with a C22 acyl chain. The presumed L3P antigen is O-methylated at the C-terminus, as are the synthetic L3P and the L5P from C-type Map (Biet et al., 2008). Indeed MALDI-TOF MS of both the synthetic and native L3P compounds showed, after saponification, a down-shift of 14 amu of the molecular ion, due to the hydrolysis of the O-methyl ester group from the C-terminus (data not shown).

Additional MS/MS analysis was conducted to confirm the structure of the putative L3P compound. Importantly, the purified S397 lipid and the synthetic compound displayed identical MS/MS spectra. Probably because of the unusual structure of the lipopeptide, specifically the acylation at the N-terminus and the presence of an N-Methyl-Val residue, fragmentation of the peptide moiety of the synthetic L3P did not yield all the expected canonical couples of fragment ions, namely, the [a, b, c] ions from the N-terminus and the [x, y, z] ions from the C-terminus (FIG. 5). Nevertheless, from the parental ion m/z 680 amu, the major observed fragmentation peaks were shared between synthetic and native L3P and were totally in agreement with the structural formula of the L3P. Representative fragment ions detected and corresponding to all the possible cleavages of the peptidic bond between the Phe and the N-Methyl-Val residues are shown in Table 2. This bond has been chosen because i) it gives the most complete sampling of the various fragment ions expected after cleavage of a peptide bond (FIG. 5) and it is conserved in both the L3P and L5P lipopeptides and ideally located to discriminate between these two compounds. Indeed, L3P and L5P share a common structure at the N-terminus, from the C20 fatty acid to N-Methyl-Val (FIG. 3). MS/MS analysis of the parental ions at m/z 694 and 708 amu of the native L3P variants confirmed the identity of the [a, b, c] fragment ions (N-terminal moiety of the lipopeptide with variation of 14 or 28 amu for the fragment ions, according to the variation of the length of the fatty acyl chain) and of the [x, y, z] fragment ions (invariant C-terminal moiety regardless of the length of the fatty acyl chain) (Table 2). Fewer expected fragment ions were detected with the 694 species of the L3P, probably due to the lower intensity observed with the corresponding parental ion.

Finally, MS/MS analysis of the L5P parental ion at 940 amu confirmed the assignment of these fragment ions: the [a, b, c] ions were identical between L3P and LSP, and the [x, y, z] ions increased in agreement with the presence of two additional amino acids (Table 2). Collectively, these data are consistent with an identity of structure between the purified native S397 lipid and the synthetic L3P, i.e. a tripeptide sequence Phe-N-Methyl-Val-Ala with a N-ter C20 fatty acid and a C-ter methyl ester.

TABLE 2

Ions originating from the fragmentation at the Phe-N-Methyl-Val bond.

| Antigen | L3P | L3P | L3P | L3P | L5P |
|---|---|---|---|---|---|
| Source | native | synthetic | native | native | synthetic |
| Parental ion (m/z) | 680.7 | 680.7 | 694.5 | 708.6 | 940.7 |
| Fatty acyl chain | C20 | C20 | C21 | C22 | C20 |
| a2 | 436.7 | 436.7 | | (464.5)* | 436.5 |
| x2 | (267.3) | (267.3) | | | 527.4 |
| b2 | 464.6 | 464.6 | (478.4) | 492.5 | (464.5) |
| y2 | 239.3 | 239.3 | 239.3 | 239.2 | 499.4 |
| c2 | 495.7 | 495.7 | | 523.4 | 495.5 |
| z2 | 208.3 | 208.3 | 208.2 | 208.2 | 468.4 |

*in brackets: peak of low intensity

Analysis by Nuclear Magnetic Resonance (NMR) Spectroscopy.

To confirm the structure of the native antigen, $^1$H-NMR spectroscopy was performed on the presumed L3P purified from the lipid extract of S397 cells.

Results of the NMR analysis were in agreement with the structure proposed for the native L3P. $^1$H-NMR spectra of the purified S397 lipid and the synthetic L3P are overlapping (FIGS. 7A and 7B), showing all the characteristic peaks for Phe, N-Methyl-Val and Ala, including peak multiplicities, coupling constants and chemical shifts (Table 3). The spectra revealed three resonances characteristic of the alpha protons of Phe, Val and Ala at 5.20, 4.47 and 4.50 ppm respectively. Two resonances typical of the amide region instead of three, between 6.0 and 7.0 ppm, confirm that one of the amino acids has no amide proton. The presence of a singlet at 2.92 ppm is consistent with the presence of a N-Methyl group on this amino acid.

TABLE 3

Characteristic 1H NMR data for the native purified L3P
The synthetic L3P gives similar data

| Chemical shift (ppm) | Peak multiplicity, Coupling constant | Assignment* |
|---|---|---|
| 0.61 | Doublet, J = 6.8 Hz | γ-CH$_3$ Val |
| 0.97 | Doublet, J = 6.4 Hz | γ-CH$_3$ Val |
| 1.35 | Doublet, J = 7.4 Hz | β-CH$_3$ Ala |
| 2.22 | Multiplet | β-CH Val |
| 2.92 | Singlet | N—CH$_3$ Val |
| 2.95/3.06 | 2 Doublets of doublet, J = 13.4 Hz | β-CH$_2$ Phe |
| 3.52 | Singlet | O—CH$_3$ |
| 4.47 | Doublet, J = 10.9 Hz | α-CH Val |
| 4.50 | Pentet | α-CH Ala |
| 5.20 | Multiplet | α-CH Phe |
| 6.08 | Doublet, J = 7.9 Hz | NH Phe |
| 6.52 | Doublet, J = 7.6 Hz | NH Ala |

*The assigned protons are underlined

The assignments (Table 3) were determined by the $^1$H-$^1$H-COSY NMR experiment where typical spin systems were observed for the three amino-acids.

$^1$H-NMR spectrum of the purified S397 shows additional peaks in comparison to the synthetic L3P (FIGS. 7A and 7B). These peaks may originate from distinct contaminant compound(s) which partially co-elute with the L3P during the preparative 2-D TLC. Indeed, the $^1$H-$^1$H-COSY NMR spectra show that spin systems of the extra peaks are not linked to any of the L3P peaks. Moreover, when the preparative TLC silica gel was scraped in the zone adjacent to that of L3P, the resulting eluted compound unambiguously gave a 1H-NMR spectrum displaying all the peaks that could not be attributed to L3P in the characteristic range from 2 to 5 ppm (FIG. 7C). Due to the resolution limit of the 2-D TLC and to the very low amount of native antigen, the complete purification of the antigen could not be achieved.

Nevertheless these results, together with the MS data highlighting the presence of L3P, demonstrate that the S397 strain produces a lipid content with, at least, the L3P compound.

Analysis of the Optical Purity

Finally, the optical purity of the individual amino acids within the native L3P was determined by gas chromatography coupled to MS after hydrolysis of the lipopeptide in 6N DCl in D$_2$O.

The results demonstrated the presence of the enantiomeric forms of D-Phe (91.4%), N-Methyl-L-Val (99.0%) and L-Ala (98.3%) (data not shown). Notably, in the course of this analysis, the identity of the three predicted amino acids was also confirmed based on their retention time and their mass spectra. Overall, the structure proposed for the L3P (FIG. 5) produced by S-type Map from the sequence of the mps1 gene has been confirmed: a peptidic core as D-Phe-N-Methyl-L-Val-L-Ala attached mostly to a 20-carbon fatty acid chain.

Lipopeptides are Cell Surface-Exposed

It has been assumed for a long time that L5P is localized in the cell wall of Map, but to the best of inventors' knowledge this has never been experimentally demonstrated. Analysis by MALDI-TOF MS of the lipids extracted from surface-exposed materials of Map K-10 shown that L5P is localized in the outer-most layers of the cell envelope (FIGS. 8A and 8B). Control TLC established that cord factor, a lipid which is never exposed at the mycobacterial cell surface (Ortalo-Magne et al., 1996) is indeed absent from the surface-exposed material analyzed here (data not shown), thus strengthening the inventors' conclusions.

Similarly, L3P was detected in surface-exposed materials prepared from Map S397 (FIG. 8D). MS/MS analysis of the compound at m/z 680 confirmed its identity as L3P, since all the representative fragment ions are present (data not shown). Minor amounts of cord factor were also detected in the surface extract of S397 (data not shown), suggesting a certain degree of cellular lysis for that strain. Nevertheless, the fact that the cell-bound and surface-exposed fractions displayed different lipid compositions (FIGS. 8C and 8D) suggests that L3P should be present at the cell surface of the S-type strain. But additional experiments are needed to confirm this localization. In both cases, detection of lipopeptides in the cell-bound lipidic fraction (FIGS. 8A and 8C) implies that they are also present within deeper layers of the cell-envelope.

Discussion:

In the process of characterizing the differences in lipids among C-type and S-type strains of Map, the inventors uncovered a new LSP not previously described. LSPs have been shown to distinguish Map from other *M. avium* subspecies, including *hominissuis* and *silvaticum*. In addition, three S-type-specific LSPs were characterized by genomic hybridization to DNA microarrays (Marsh et al., 2006). While these LSPs usually span several genes and range in size from 4.5 kb to over 65 kb, the LSP reported here is located exclusively within the mps1 gene and spans 6.3 kb of DNA present in C-type strains, but not in any of the S-type strains examined. It is likely that this LSP remained hidden, despite extensive genomic comparison studies, because it is entirely contained within a single gene. This newly discovered LSP now provides an additional target to distinguish S-type from C-type strains of Map.

Over 10% of the mycobacterial genome is coded for proteins involved in lipid metabolism. Large genes, including mmpL/S, pks and nrp are involved in lipid biosynthesis or transport (Ripoll et al., 2007), but the role of each of these needs to be determined by investigating genetic differences and correlating those to phenotypic differences as has been accomplished for lipooligosaccharides in *M. smegmatis*. Although numerous genetic differences between C- and S-type Map strains have been reported, the inventors' results represent the first example of a genetic difference that has been phenotypically defined. It had been previously thought that all Map strains produce L5P since only one bovine strain had been evaluated by 2-D TLC (Eckstein et al., 2006) and several other Map strains examined by 1-D TLC (Biet et al., 2008); however, 1-D TLC did not resolve differences due to limits of the technique. The difference in lipid composition was discovered only through extensive biochemical and physicochemical analysis of lipid extracts combined with detailed sequence and assembly of the large and highly repeated mps1 gene in the S-type strain.

Based on TLC analysis, Map does not produce GPLs but instead contains a lipopeptide molecule (Biet et al., 2008) initially termed Lipopeptide-I (Riviere et al., 1996) and later Para-LP-01 (Eckstein et al., 2006). This nonpolar lipid, most recently termed L5P for lipopentapeptide, is an abundant molecule in Map and is not detected in *M. avium* subsp. *avium* (Eckstein et al., 2006). It has been demonstrated that L5P is antigenic in antibody-based tests (Biet et al., 2008, Verdier et al., 2013) with minor cell-mediated immune responses, and can stimulate IFN-γ (Holbert et al., 2015). The inventors further show for the first time that L5P is clearly surface-exposed, i. e. localized in the outer-most layers of the cell envelope. The antigenicity of L3P in the S-type strains has yet to be tested, but as the L3P amino acids are conserved with that of L5P, it is unlikely that L3P will enable the specific detection of S-type Map strains.

The unique mycobacterial cell wall is important in the physiology of these bacteria and has been studied for its properties on immune stimulation and increased virulence (Howard et al., 2006, Bernut et al., 2014). Considering that L3P shares with L5P and GPLs a cell-envelope surface localization, and depending on the presence/absence of GPLs and lipopeptides described herein for a small subset of closely related mycobacteria, their physiological properties may change greatly depending on the mycobacterial strain and their evolutionary history.

NRPSs create substantial biological flexibility because no ribosomes or RNA template are needed for peptide assembly. The ribosome recognizes only 20 naturally occurring amino acids for peptide assembly; however, NRPS can specify over 500 amino acids, creating unlimited peptides for highly specialized biological functions (Walsh et al., 2013). In this study the inventors showed that the tripeptide produced in S-type strains consists of only one naturally occurring amino acid, L-Ala, and two that are "non-coded" amino acids. The C-type mps1 has five modules encoding a lipopentapeptide, but there are examples of two NRP genes, arranged in tandem, that together encode a five module NRPS to construct the antibiotic nocardicin A (Gaudelli et al., 2015). Perhaps to further increase diversity in these nonribosomal peptides, known NRPSs can be classified into three groups, linear, iterative and nonlinear. In linear NRPSs, the sequence of the resulting peptide chain is entirely determined by the number and order of the modules. Iterative NRPSs use their modules or domains more than once in the assembly of one single product. Nonlinear NRPSs involve complex scenarios with parallel nonlinear organization of domains and unusual arrangements such as internal cyclisation or incorporation of small soluble molecules. Data from this study show that mps1 for both L3P and L5P NRPSs are linear in organization.

Could the defined change in peptide length described in this study be enough to account for host preferences in C- and S-type strains of Map? S-type has a substantial host preference for sheep, but not exclusively, since S-type has also recently been isolated from several Arabian camels (Ghosh et al., 2012). However, C-type has a broader host range since it has been isolated from many ruminant species, including goat, deer and bison (Biet et al., 2012, Sibley et al., 2007). Nonetheless, there is a clear host preference or adaptation among these strains. It may be possible that this subtle change in peptide composition could define the growth rates or other phenotypic differences between these types. However, it can be excluded the fact that this NRP is responsible for pigment production reported in the S-type strains (Biet et al., 2012), since the inventors observed that L3P is colorless (data not shown). Regardless, it is clear that both lipopeptides share common epitopes since D-Phe, N-Methyl-L-Val and L-Ala are conserved in both Map types. The two amino acids missing from the S-type strain L3P are L-Ile and L-Phe. Mutational studies will confirm this point.

Rough and smooth colony appearance among *Mycobacterium* species is not only attributed to changes in their lipid composition (Wright et al., 1996) but also to virulence and drug resistance (Kansal et al., 1998, Howard et al., 2006). In fact L5P disappears when Map are cultured in cow's milk but is present in high abundance when cultured in Middlebrook 7H9 media (Alonso-Hearn et al., 2010), suggesting that the lipid profile of Map changes significantly when exposed to different environments. But there may be much more going on biologically that accounts for these lipid differences. Only recently were lipopeptides shown to interact with TLR2 receptors on key immune cells (Jimenez-Dalmaroni et al., 2015). Much research is still needed in this area to understand the biological significance of subtle lipid changes among mycobacterial species and isolates.

Materials and Methods:

Culture of S-type Map. S397 is an S-type strain of Map that has been previously characterized by whole genome sequencing (Bannantine et al., 2012). It was initially isolated from a Suffolk breed of sheep in Iowa in 2004. Both strains S397 and K-10 were cultured in Middlebrook 7H9 media (BD Biosciences, San Jose, CA) supplemented with 10% OADC, 0.05% TWEEN 80 (Polyoxyethylenesorbitan monooleate) and 2 µg/mL Mycobactin J. The culture conditions were 37° C. with no shaking in 2-liter Erlenmeyer flasks each containing 500-mL volumes of media. Milligram quantities were obtained from multiple cultures for downstream analyses.

Sequencing and assembly of mps1. A combination of sequencing and assembly strategies were required to fully assemble the mps1 gene from Map S397. The large size of this gene and the presence of long repeats resulted in incomplete mps1 assembly regardless of the assembler employed (MIRA v. 3.9.9, Roche gsAssembler v. 2.6, and Velvet v. 0.7.09). Targeted de novo subassemblies of the mps1 region were created by first extracting reads that mapped to the region via MIRA's mirabait functionality using the partial contigs that aligned with MAP_1420 from K-10 and the MAP4_2425 homolog (Bannantine et al., 2014) as targets, and then de novo assembling those reads with MIRA. This was done in an iterative fashion and was supplemented as needed with additional targeted subcloning, PCR, and Sanger sequencing of the mps1 gene region until full unambiguous assembly was obtained. The GenBank accession number for mps1 in Map S397 is KP720596.

Southern hybridization analysis. Mycobacteria were grown to late log phase in Middlebrook 7H9 medium (10 mL) and harvested by centrifugation at 6,000×g for 10 min. The bacteria were heat killed for 10 min at 95° C. The pellet was resuspended in 10 mL of TE buffer (10 mM Tris-HCl [pH 7.6], 1 mM EDTA) and centrifuged again at 6,000×g for 10 min. The semidried mycobacterial pellet was resuspended into 1 mL TE buffer (10 mM Tris-HCl [pH 7.6], 1 mM EDTA). After the addition of 200 μL of lysozyme (200 mg/mL) and incubation overnight at 37° C., 100 μL of SDS 10% and 50 μL Proteinase K (Macherey-Nagel) were added and incubated 4 hours at 56° C. 100 μL of 10% CTAB were mixed and incubated for 1 h at 65° C. 1 volume of phenol-chloroform-isoamyl alcohol (25:24:1 (vol/vol)) was added and the solution was vigorously mixed and then centrifuged at 14,000×g for 5 min in phase lock gel (Qiagen). The supernatant was mixed with 1 volume of chloroform-isoamyl alcohol (24:1 (vol/vol)) and centrifuged again. The DNA was precipitated by the addition of 0.8 volume of isopropanol and 0.3 M sodium acetate (final concentration). After centrifugation for 30 min at 14,000×g, the DNA was air dried, dissolved in 50 μL of TE buffer (10 mM Tris-HCl [pH 7.6], 1 mM EDTA), and stored at −20° C. until further use.

Southern blot of Map DNA was performed as previously described (Southern, 1975, van Soolingen et al., 1994) with some modifications. The mps1 DNA probe was prepared by PCR amplification of a 491-bp fragment sequence specific for Map using the primers described in this study (table 4). PCRs were performed starting from 10 ng of chromosomal DNA of Map strain K-10 by using a TC-512 thermal cycler (Techne). The PCR product was purified on Macherey-Nagel spin columns according to the manufacturer's instructions. The probe was biotin labeled with the NEBlot Phototope kit (New England Biolabs) by following the instructions of the manufacturer. Digestion was performed with 3 μg of DNA prepared as described above and 7 U of SacI (Promega) at 37° C. for at least 6 h. Fragments were resolved by agarose gel electrophoresis and transferred onto Immobilon-S nylon membranes (Millipore) by vacuum transfer with the Vacu-Gene system (Pharmacia LKB Biotechnology). Detection of DNA fragments hybridizing with the biotinylated probe was performed with the Phototope-Star detection kit for nucleic acids (New England Biolabs), according to the manufacturer's instructions. The 2-Log DNA Ladder (New England Biolabs) was used as a molecular size marker.

TABLE 4

```
primer sequences:
Primer 1: forward primer; primers 2 and 3: reverse primers:
Target: MIRU 292
Primer 1: CTTGAGCAGCTCGTAAAGCGT (SEQ ID NO: 18)-

Primer 2: GCTGTATGAGGAAGTCTATTCATGG (SEQ ID NO: 19)

Target MIRU X3
Primer 1: AACGAGAGGAAGAACTAAGCCG (SEQ ID NO: 20)-

Primer 2: TTACGGAGCAGGAAGGCCAGCGGG (SEQ ID NO: 21)

target: VNTR 25
Primer 1: GTCAAGGGATCGGCGAGG (SEQ ID NO: 22)-

Primer 2: TGGACTTGAGCACGGTCAT (SEQ ID NO: 23)

target: VNTR 47
Primer 1: CGTTGCGATTTCTGCGTAGC (SEQ ID NO: 24)-

Primer 2: GGTGATGGTCGTGGTCATCC (SEQ ID NO: 25)

target: VNTR 3
Primer 1: CATATCTGGCATGGCTCCAG (SEQ ID NO: 26)-

Primer 2: ATCGTGTTGACCCCAAAGAAAT (SEQ ID NO: 27)

target: VNTR 7
Primer 1: ACAACGAAACCTACCTCGTC (SEQ ID NO: 28)-

Primer 2: GTGAGCTGGCGGCCTAAC (SEQ ID NO: 29)

target: VNTR 10
Primer 1: GACGAGCAGCTGTCCGAG (SEQ ID NO: 30)-

Primer 2: GAGAGCGTGGCCATCGAG (SEQ ID NO: 31)

target: VNTR 32
Primer 1: CCACAGGGTTTTTGGTGAAG (SEQ ID NO: 32)-

Primer 2: GGAAATCCAACAGCAAGGAC (SEQ ID NO: 33)

target: msp1 probe
Primer 1: CGCGGCGAGCGGGAGCTGGTGC (SEQ ID NO: 34)-

Primer 2: CGCAGCGGGGAGCGCCGGTCGG (SEQ ID NO: 35)
```

TABLE 4-continued

```
target: LSP mps1
Primer 1: GCAGTACGCCGACTACAC (nt 3-20 of SEQ ID NO: 10)-

Primer 2: AGAAACCGATCAGCTCGTCG (SEQ ID NO: 11)

Primer 3: ACCGGGAAAACAGCAGTG (SEQ ID NO: 12)

target: LSP A 20
Primer 1: GGCGTTACAGAATTGCCTTG (SEQ ID NO: 36)-

Primer 2: GCTCGAAGTTGGAGATCAGG (SEQ ID NO: 37)

Primer 3: GTACGTGGTGACCAATGTCG (SEQ ID NO: 38)

target: LSP A 4-II
Primer 1: TAGAAGGTGCGGGAAAGTTG (SEQ ID NO: 39)-

Primer 2: GTCTATCTGGCGGTGCTCTC (SEQ ID NO: 40)

Primer 3: GTCGAAGCAGCGTTGATTG (SEQ ID NO: 41)

target: GyrA locus 34
Primer 1: TGTTCTTCACCACCCAGGGCCGGG (SEQ ID NO: 42)-

Primer 2: TTGAGCGACAGCAGGTAGTCGTCGGCG (SEQ ID NO: 43)

target: GyrB locus 45
Primer 1: TTGGTGCGCCGCAAGAGCGCAACCG (SEQ ID NO: 44)-

Primer 2: ATTTCAGCTTGTACAGCGGTGGC (SEQ ID NO: 45)

Reference : Thibault, et al (2007) Semret et al. (2006) and Castellanos
et al. (2007)
```

Reaction conditions for LSP$^{mps1}$ amplification. A panel of Map isolates described in Table 1 was tested for the presence or absence of the large sequences identified within the genes mps1 of K-10 compared to S397. This was done with a multiplex PCR approach (Semret et al., 2006) using a set of three primers: two primers (forward and reverse) designed towards the flanking regions (bridging primers) of the LSP and a third primer designed to recognize a sequence internal to the LSP (internal primer). The primers were designed such that the resulting PCR products would be of different sizes depending on the presence or absence of the LSP under study. Primer sequences are provided in Table 4. The PCR mixture comprised 2 µL of DNA solution added to a final volume of 25 µL containing 0.1 µL of GoTaq Flexi DNA polymerase (5 U/µL Promega), 2 mM (each) dATP, dCTP, dGTP, and dTTP (Promega); 5 µL of 5×PCR buffer supplied by the manufacturer; 1 µM of each primers; 1 µL of dimethyl sulfoxide (Sigma); 1.5 mM of MgCl$_2$ and 5 µL of 5M betaine solution (Sigma). The reactions were carried out using a TC-512 thermal cycler (Techne). PCR conditions were as follows: 1 cycle of 5 min at 94° C.; 30 cycles of 30 s at 94° C., 30 s at 62° C., and 30 s at 72° C.; and 1 cycle of 7 min at 72° C. To detect presence or absence of each LSP, PCR products were analyzed by electrophoresis using 1.5% agarose gels.

Bioinformatic prediction of peptide composition from NRPS sequence. The peptide composition of the lipopeptides analyzed in this study were deduced from DNA sequence comparisons between K-10 and S397 strains as well as a bioinformatics approach using domain prediction software including the NCBI web tools ncbi.nlm.nih.gov/Structure/cdd/wrpsb.cgi and the web site of PKS/NRPS Analysis at nrps.igs.umaryland.edu/nrps. Peptide composition was determined using the web-based server NRPSpredictor2 (Rottig et al., 2011).

Chemical synthesis of the lipopeptides. The control lipopeptides (L3P and L5P) were synthesized on solid phase using the standard Fmoc chemistry protocol, as previously described (Biet et al., 2008). After cleavage from the resin, the crude L3P product was purified on a silica gel column using CH$_2$Cl$_2$/methanol as eluent (from 98:2 to 97:3 (vol/vol)), and 80 mg of the lipopeptide were obtained (yield 80% based on the net peptide content). The synthetic L3P was characterized by electrospray ionization MS (Q-Tof Micro Waters), quantitative amino acid analysis (AAA) (after hydrolysis with 6N HCl at 110° C. for 48 h and using a Beckman 6300 analyzer) and NMR (Bruker 400 MHz instrument).

MS: C$_{39}$H$_{67}$N$_3$O$_5$ (calcd 657.5081) m/z 658.5155 [M+H]$^+$, 680.4994 [M+Na]$^+$.

AAA: Ala 1 (1), Phe 0.96 (1), and an extra peak typical of N-Methyl-Val.

$^1$H NMR (CDCl$_3$): δ 0.60 (d, 3H, CH$_3$γ Val, J=6.68 Hz), 0.90 (t, 3H, CH$_3$ lipid, J=7.05 Hz), 0.96 (d, 3H, CH$_3$γ Val, J=6.41 Hz), 1.25-1.29 (m, 32H, 16 CH$_2$ lipid), 1.35 (d, 3H, CH$_3$β Ala, J=7.21 Hz), 1.53-1.59 (m, 2H, CH$_2$CH$_2$CO lipid), 2.15 (t, 3H, CH$_2$CO lipid, J=7.60 Hz), 2.18-2.27 (m, 1H, CH$_2$β Val), 2.93 (s, 3H, NCH$_3$), 2.97 (dd, 1H, 1CH$_2$β Phe, J$_{1CH2β,CHα}$=8.16 Hz), 3.08 (dd, 1H, 1CH$_2$β Phe, J$_{1CH2β,CHα}$=8.04 Hz J$_{1CH2β,1CH2β}$=13.36 Hz), 3.74 (s, 3H, OCH$_3$), 4.45 (d, 1H, CHα Val, J=11.04 Hz), 4.5 (p, 1H, CHα Ala, J$_{CHα,NH}$=7.2 Hz), 5.17-5.24 (dt, 1H, CHα Phe, J$_{CHα,NH}$=6.09 Hz), 6.13 (bd, 1H, NH Phe), 6.59 (bd, 1H, NH Ala), 7.18-7.30 (5H, Ph).

$^{13}$C NMR (CDCl$_3$): δ 14.08 (CH$_3$ lipid), 17.86 (CH$_3$β Ala), 18.64, 19.65 (CH$_3$γ Val), 22.67 (CH$_2$ lipid), 25.53 (CH$_2$CH$_2$CO lipid), 25.84 (CHβ Val), 29.21, 29.34, 29.45, 29.64, 29.68 (CH$_2$ lipid), 30.96 (NCH$_3$), 31.91 (CH$_2$ lipid), 36.44 (CH$_2$CO lipid), 38.97 (CH$_2$β Phe), 47.89 (CHα Ala), 50.38 (CHα Phe), 52.28 (OCH$_3$), 63.12 (CHα Val), 127.11, 128.57, 129.33, 135.80 (Ph), 169.05 (CO Val), 172.55 (CO lipid), 172.94 (CO Ala), 173.41 (CO Phe).

Lipid extraction, 2-D TLC and 1-D TLC. The culture of the S-type strain of Map afforded 317 mg of cells (dry weight). Lipids were extracted with chloroform/methanol (1:2 then 2:1 (vol/vol)) resulting in 7.6 mg of product. For analytical purposes, 500 µg of this crude extract were loaded on 2-D TLC plates and eluted using chloroform/methanol (96:4 (vol/vol)) in the first dimension followed by toluene/acetone (80:20 (vol/vol)) in the second dimension. Control synthetic L3P was deposited at 15 µg in chloroform and served as a marker for each dimension. TLC plates were revealed by spraying 10% copper sulfate in 8% phosphoric acid, followed by charring.

For the L3P purification, 7 mg of the crude extract in 100 µL of CH$_2$Cl$_2$ were loaded on preparative silica gel 60 F$_{254}$ 2-D TLC (20×20 cm, thickness 0.5 mm) (Merck) and eluted using the same solvent systems as above. After scraping the spot of interest (~7 mm diameter) off the silica plate, the L3P was eluted in batch with 4 times 500 µL of CH$_2$Cl$_2$/methanol 95:5 (vol/vol). The evaporation under argon afforded approximately 50 µg of purified native antigen. The adjacent silica gel zone below (~6 mm diameter spot) was treated using the same procedure for the NMR control.

This purified native L3P was analyzed by silica gel 60 F$_{254}$ 1-D TLC in comparison to both synthetic controls L3P and L5P (approximately 2 µg of each). The TLC was eluted with CH$_2$Cl$_2$/methanol 95:5 (vol/vol) and revealed as described above.

Surface-exposed material preparation. The surface-exposed material was recovered from mycobacteria treated with 10 g of glass beads as previously described (Ortalo-Magne et al., 1996). Chloroform and methanol were added to the filtrates derived from this treatment obtain a partition mixture composed of chloroform/methanol/water (3:4:3 (vol/vol/vol)), then the organic phases were washed with water and evaporated to dryness to yield the cell surface-exposed lipids. The treated bacteria were extracted as described above to yield the cell bound lipids. Presence of cord factor was monitored by TLC developed in chloroform/methanol (90:10 (vol/vol)) and revelation by spraying 0.2% anthrone in sulfuric acid, followed by charring.

Analytical Procedures.

MALDI-TOF/TOF-MS and MS/MS analyses were conducted in the positive ionization and reflectron mode by accumulating 10 spectra of 250 laser shots, using the 5800 MALDI TOF/TOF Analyser (Applied Biosystems/Absciex) equipped with a Nd:Yag laser (349 nm wavelength). For MS and MS/MS data acquisitions, uniform, continuous, and random stage motion was selected at a fixed laser intensity of 4000 (instrument-specific units) and 400 Hz pulse rate and 6000 (instrument-specific units) and 1000 Hz, respectively. For MS/MS data acquisition, the fragmentation of selected precursors ions was performed at a collision energy of 1 kV using air as collision gas. Lipid samples were dissolved in chloroform and were directly spotted onto the target plate as 0.5 µl droplets, followed by the addition of 0.5 µL of matrix solution (10 mg of 2,5-dihydroxybenzoic acid (Sigma-Aldrich). mL$^{-1}$ in CHCl$_3$/CH$_3$OH, 1:1 (vol/vol)). Samples were allowed to crystallize at room temperature. Spectra were externally calibrated using lipid standards.

For comparative NMR analyses, 1-D $^1$H and $^1$H-COSY $^1$H/$^1$H (COrrelation SpectroscopY), compounds were dissolved in CDCl$_3$/CD$_3$OD (1:1 (vol/vol), 99.8% purity, Euriso-top, CEA Saclay, France). Experiments were conducted using a 600 MHz Bruker NMR spectrometer equipped with cryosonde. $^1$H chemical shifts are given in parts/million (ppm) downfield from internal tetramethylsilane at 0 ppm. All experiments were recorded at 295° K without sample spinning. The Bruker pulse programs were used and optimized (pulse lengths and delays) for each 1-D or 2-D experiments. Data were analyzed using the TopSpin (Bruker BioSpin) software.

Example 2: Serological Results Using L5P Hydrosoluble Analogue and L3P to Detect Map Materials and Methods:
1. Material and Methods
a. Chemical Synthesis of the Antigens.

The antigens were synthesized manually on solid phase using Fmoc chemistry.

The L3P lipopeptide was prepared using a 4-hydroxymethylbenzoyl resin (HMBA-AM resin, Novabiochem) as previously described (Biet et al., 2008). After cleavage from the resin, the crude L3P was purified on a silica gel column using CH$_2$Cl$_2$/methanol as eluent (from 98/2 to 97/3 v/v), and 80 mg of the lipopeptide were obtained (yield 80%).

The L5P$^{H2O}$ antigen was prepared by attaching N-(Fmoc-13-amino-4,7,10-trioxa-tridecayl)-diglycolic acid (Novabiochem) to a Wang resin using 1-(mesitylene-2-sulfonyl)-3-nitro-1,2,4-triazole and N-methylimidazole (B. Blankemeyer-Menge et al., 1990). The capping, coupling and deprotection steps were performed as previously described (Biet et al., 2008).

The product was cleaved from the resin with aqueous trifluoroacetic acid (TFA)/triisopropylsilane/H$_2$O 95/2.5/2.5 v/v/v for 2 hours at room temperature. After filtration of the resin, the filtrate was concentrated, and diluted with CH$_2$Cl$_2$/H$_2$O 50/50. The organic phase was extracted twice with H$_2$O. The aqueous phases were pooled and lyophilized. The crude L5P$^{H2O}$ was purified by reverse-phase flash chromatography using a gradient of H$_2$O+0.1% TFA/CH$_3$CN+0.1% TFA from 70/30 to 50/50 and 126 mg of the peptide derivative were obtained (yield 88%).

The purified compounds L3P and L5P$^{H2O}$ were characterized by electrospray ionization MS (Q-Tof Micro Waters), quantitative amino acid analysis (AAA) (after hydrolysis with 6N HCl at 110° C. for 48 h and using a Beckman 6300 analyzer) and NMR (Bruker 400 MHz instrument).

L3P:

MS: C$_{39}$H$_{67}$N$_3$O$_5$ (calcd 657.5081) m/z 658.5155 [M+H]$^+$, 680.4994 [M+Na]$^+$.

AAA: Ala 1 (1), Phe 0.96 (1), and an extra peak typical of N-Methyl-Val.

$^1$H NMR (CDCl$_3$): δ 0.60 (d, 3H, CH$_3$γ Val, J=6.68 Hz), 0.90 (t, 3H, CH$_3$ lipid, J=7.05 Hz), 0.96 (d, 3H, CH$_3$ γ Val, J=6.41 Hz), 1.25-1.29 (m, 32H, 16 CH$_2$ lipid), 1.35 (d, 3H, CH$_3$β Ala, J=7.21 Hz), 1.53-1.59 (m, 2H, CH$_2$CH$_2$CO lipid), 2.15 (t, 3H, CH$_2$CO lipid, J=7.60 Hz), 2.18-2.27 (m, 1H, CHβ Val), 2.93 (s, 3H, NCH$_3$), 2.97 (dd, 1H, 1CH$_2$β Phe, J$_{1CH2β,CHα}$=8.16 Hz), 3.08 (dd, 1H, 1CH$_2$β Phe, J$_{1CH2β,CHα}$=8.04 Hz J$_{1CH2β,CHβ}$=13.36 Hz), 3.74 (s, 3H, OCH$_3$), 4.45 (d, 1H, CHα Val, J=11.04 Hz), 4.5 (p, 1H, CHα Ala, J$_{CHα,NH}$=7.2 Hz), 5.17-5.24 (dt, 1H, CHα Phe, J$_{CHα,NH}$=6.09 Hz), 6.13 (bd, 1H, NH Phe), 6.59 (bd, 1H, NH Ala), 7.18-7.30 (5H, Ph).

$^{13}$C NMR (CDCl$_3$): 14.08 (CH$_3$ lipid), 17.86 (CH$_3$β Ala), 18.64, 19.65 (CH$_3$ γ Val), 558 22.67 (CH$_2$ lipid), 25.53 (CH$_2$CO lipid), 25.84 (CHβ Val), 29.21, 29.34, 29.45, 29.64, 29.68 (CH$_2$ lipid), 30.96 (NCH$_3$), 31.91 (CH$_2$ lipid), 36.44 (CH$_2$CO lipid), 38.97 (CH$_2$β Phe), 47.89 (CHα Ala), 50.38 (CHα Phe), 52.28 (OCH$_3$), 63.12 (CHα Val), 127.11, 128.57, 129.33, 135.80 (Ph), 169.05 (CO Val), 172.55 (CO lipid), 172.94 (CO Ala), 173.41 (CO Phe).

L5P$^{H2O}$:

MS: $C_{47}H_{73}N_7O_{12}$ (calcd 927.5317) m/z 928.5383 [M+H]$^+$, 950.5099 [M+Na]$^+$.

AAA: Ala 1 (1), Phe 1.79 (2), Ile 0.90 (1), and an extra peak typical of N-Methyl-Val.

$^1$H NMR (MeOD): δ 0.68 (d, 3H, CH$_3$γ Val, J=6.56 Hz), 0.79 (d, 3H, CH$_3$γ Val, J=6.64 Hz), 0.81 (d, 3H, CH$_3$γ Ile, J=6.89 Hz), 0.85 (t, 3H, CH$_3$δ Ile, J=7.38 Hz), 1.01-1.09 (m, 1H, 1CH$_{2γ}$ Ile), 1.30 (d, 3H, CH$_3$β Ala, J=7.12 Hz), 1.45-1.51 (m, 1H, 1CH$_{2γ}$ Ile), 1.70-1.81 (m, 5H, CHβ Ile, CH$_2$ D and K), 2.08-2.14 (m, 1H, CH$_2$β Val), 2.92 (dd, 1H, 1CH$_2$β Phe), 3.01 (dd, 1H, 1CH$_2$β Phe), 3.05 (s, 3H, NCH$_3$), 3.13 (dd, 1H, 1CH$_2$β Phe), 3.20 (dd, 1H, 1CH$_2$β Phe), 3.23 (t, 2H, CH$_2$ C or L, J=6.86 Hz), 3.33 (t, 2H, CH$_2$ C or L, J=6.84 Hz), 3.48-3.54 (m, 4H, CH$_2$ E and J), 3.56-3.64 (m, 8H, CH$_2$ F, G, H and I), 4.04 (s, 2H, CH$_2$ B), 4.06-4.10 (m, 1H, CHα Ile), 4.18 (s, 2H, CH$_2$ A), 4.23-4.28 (q, 1H, CHα Ala), 4.47 (d, 1H, CHα Val, J=10.96 Hz), 4.61 (dt, 1H, CHα Phe), 4.68 (dt, 1H, CHα Phe), 7.16-7.19 (m, 2H, NH PEG), 7.21-7.38 (m, 10H, 2Ph), 7.97 (d, NH Ile), 8.13 (d, NH Phe).

$^{13}$C NMR (MeOD): δ 11.34 (CH$_3$γ Ile), 15.75 (CH$_3$γ Ile), 18.34 (CH$_3$β Ala), 19.87, 20.00 (2CH$_3$γ Val), 26.10 (CH$_{2γ}$ Ile), 28.50 (CHβ Val), 30.35, 30.38 (CH$_2$ D and K), 32.05 (NCH$_3$), 37.69, 37.90 (CH$_2$ C and L), 38.14, 38.61 (2CH$_2$β Phe), 50.56 (CHα Ala), 53.35, 55.93 (CHα Phe), 59.50 (CHα Ile), 64.94 (CHα Val), 69.22 (CH$_2$ A), 69.82, 70.11 (CH$_2$ E and J), 71.28, 71.31, 71.52, 71.58 (CH$_2$ B, F, G, H, and I), 127.87, 129.08, 129.56, 130.27, 130.35, 130.59, 135.26, 138.28 (Ph), 171.06, 171.92, 172.20, 172.85, 173.25, 173.63, 174.43 (CO).

well of the microplate Nunc Maxisorp and incubated for 18 hours at 4° C. with PPD or water-soluble variant. For the L5P coating plate were incubated 18 hours at 37° C. until total methanol evaporation (do not cover the plate). Plates were then washed three times with 200 μL of PBS containing 0.05% TWEEN 20 (Polyoxyethylenesorbitan monooleate) (PBS-T), and 50 μL Blocking Buffer PBS-TG (PBS-0.05% TWEEN 20 (Polyoxyethylenesorbitan monooleate), 0.5% Gelatin ref BIO-RAD 170-6537) were added to each well and incubated for 1 hour 30 min at 37° C.

After removing the blocking buffer 50 μL of primary antibody or serum diluted (1/100) in PBS-TG to each well were added and plates were incubated for 1 hour 30 at 37° C.

Plates were washed five times with 200 μL of PBS-T, and 50 μL of a solution of Recombinant Protein G Peroxidase Conjugated (reference 31499, Thermo Scientific) diluted at 0.5 μg/mL in PBS 0.05% TWEEN 20 (Polyoxyethylenesorbitan monooleate) were added to each well and plates were incubated for 1 hour at room temperature.

Plates were then washed five times with 200 μL of PBS-T, and HRP substrate were added. The plates were read photometrically at 414 nm.

d. Storage

Before solubilization, L5P can be conserved at 4° C. or –20° C., and after solubilization at room temperature less than 2 days.

Results:

L5P$^{H2O}$ is a Suitable Hydrosoluble Derivative of LSP:

The L5P is very hydrophobic and does behave very differently as compared to conventional proteic antigens

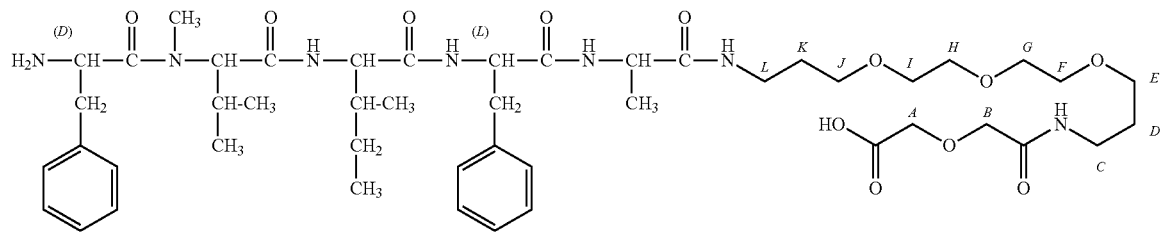

b. Sera

The potential of L5P and L3P as Map diagnostic antigen was assessed by ELISA. To validate thoroughly the diagnostic value of these molecules with appropriate sample sizes, the inventors used collection of sera already extensively described (Leroy et al, Proteomics 2007) (Mercier et al., Veterinary Record (2010) (Schinköthe J et al. J Comp Pathol. 2016 August-October; 155(2-3):218-30) (Dukkipati V S Vet Microbiol. 2016 Nov. 15; 195:136-143). They also used sera from animals infected by M. bovis form (JL Moyen Laboratoire Départemental d'Analyse & de Recherche de Dordogne).

c. Antibody ELISA Procedure

Preparation of antigen solution: The synthetic L5P lyophilized was carefully dissolved with ethanol or methanol. The required volume of ethanol to give a stock concentration of 1 mg/ml was added in the tube. The lyophilisate was then allowed to resuspend for at least 2 hours (gentle stirring). It is recommended to keep the working solution at room temperature taking care to avoid evaporation. L5P was used at a working concentration of 25 μg/mL in ethanol or methanol. 50 μL of antigen preparation were added in each which are hydrosoluble. It is soluble in DMSO, CHCl$_3$, CH$_2$Cl$_2$, MeOH and EtOH (<1 mg/ml), but insoluble in water or aqueous buffers. Glass containers are thus to be used, and contacts with polypropylene/ependorf surface are to be minimized. Material handling like dilution and transfer steps is also to be minimized.

These properties of L5P are thus likely to cause difficulties in using a diagnostic test based on the L5P as antigen.

The inventors have thus developed a hydrosoluble derivative of LSP, named L5P$^{H2O}$, in order to circumvent these potential difficulties. The structure of L5P and L5P$^{H2O}$ are illustrated in FIG. 9. FIG. 10 shows the performance of L5P and the hydrosoluble derivative L5P$^{H2O}$ on a panel of previously well-defined sera (Leroy et al, Proteomics 2007) including 60 positive sera from bovine infected by Map (MAP+) and 53 sera from healthy bovine (Controls). In ROC analysis of LSP, the area under the curve and its standard error were found equal to 0.97 (95% confidence interval, 0.94557 to 0.9955) and 0.01269, respectively. The L5P$^{H2O}$ was successfully evaluated whether in ethanol or in PBS. In ROC analysis, the area under the curve and its standard error were found equal to 0.9313 (95% confidence interval, 0.8843 to 0.9783) and 0.02398, and 0.9453 (95% confidence interval, 0.9064 to 0.9841) and 0.01981, respectively.

These results confirm that both L5P and L5P$^{H2O}$ have satisfying performance in the diagnosis of Map infection in bovine.

Figure 11:
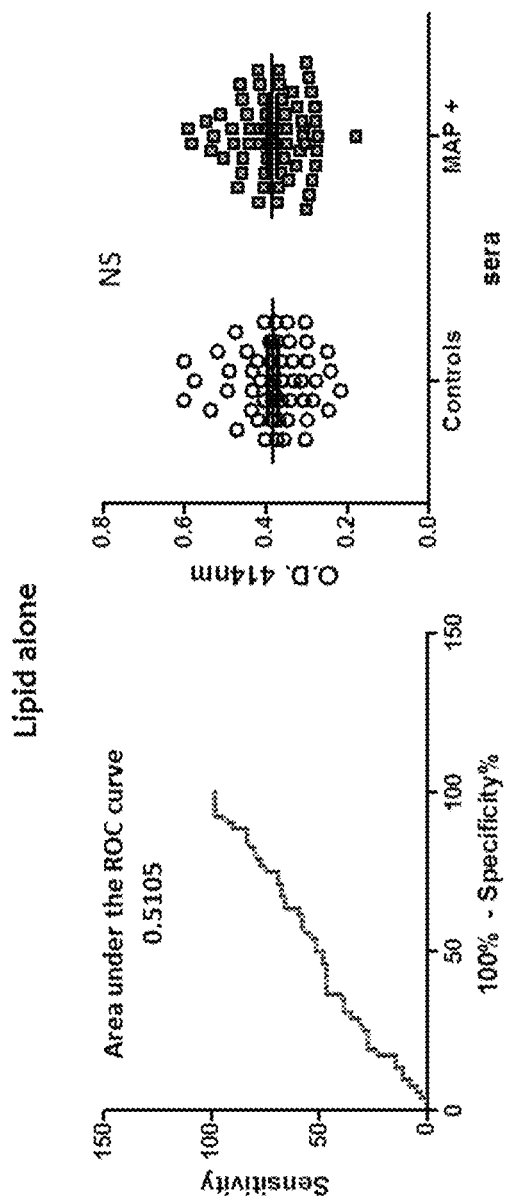

The inventors have moreover confirmed that the antibody response detected with sera of infected animals is not directed against the lipid moiety of LSP, as can be deduced from the results illustrated in FIG. 11.

It can thus be concluded that:
L5P is a valuable biomarker to detect animal infected by Map. It was validated in ELISA using collections of sera from cattle.
The ELISA detection relies on the L5P peptide since the lipid moiety does not discriminate control from infected animals
A high quality hydrosoluble L5P derivative was synthesized.
The hydrosoluble antigen L5P$^{H2O}$ is a satisfying synthetic mimic of L5P and can be advantageously used in a standard ELISA diagnostic test for detecting Map-infected animals.

L5P is Suitable to Discriminate Animals Infected by Map Versus *M. bovis*:

The inventors have then confirmed that L5P is an antigen specific for Map, absent from *M. bovis* and which does not cross-react with sera of animals infected by *M. bovis*. The corresponding results are illustrated in FIG. 12.

This antigen can therefore be used to discriminate animals infected with *M. bovis* from animals infected with Map. The same property is to be expected for the hydrosoluble analogue of L5P.

L5P is not Optimal as a Diagnostic Antigen in the Context of Ovine Paratuberculosis Induced by Map of S-Type:

The results illustrated in FIG. 13 show that less than half of the sheep sera do not appear to contain anti-L5P antibodies. In sheep the majority of strains of Map isolated are of type S and the inventors demonstrated (see example 1) that these strains do not produce the L5P, but rather the closely-related antigen called L3P (see FIG. 9 and example 1). This different antigenic composition of 5-type strains is in agreement with the ELISA results presented in FIG. 13.

In view of the high number of undetermined diagnoses as illustrated in FIG. 13, it can be deduced that L5P does not seem suitable as a diagnostic antigen in the context of ovine paratuberculosis induced by Map of S-strain.

Use of L3P in the Map Serodiagnosis:

The inventors have then used L3P in Elisa serodiagnosis test, using the same protocol as detailed above for L5P. The results are presented in FIG. 14. These results show that L3P is recognized by the antibodies of animals infected by Map of S-type.

Anti-Map antibodies present in the serum of animals infected with C-type strains cross react with the L3P. These results are not surprising given the structures of the antigens that share epitopes. These results suggest that L3P, together with L5P, could be used for specific diagnosis of sheep (or other animal) infected with strains of type S.

The L3P will thus improve the serological diagnosis of Map in a context of infection with type S strains. Technical optimization of the ELISA protocol, especially steps of coating and saturation is in progress. The comprehensive evaluation of infected animals with accurately characterized strains is also in progress using a large collection of sera.

It is to be noted that these results were performed with a limited number of reference sera from bovines infected by C-type strains and sera from ovines infected by S-type strains. They nevertheless show that S-type is detected with L3P as antigen in the ELISA.

Example 3: L3P Promotes a Cell-Mediated Immune Response Whereas L5P Promotes B Cell Responses The present inventors have also confirmed that L3P elicits a cell mediated immune response as well as humoral response. By comparison with the immunoreactivity of L5P, they have moreover highlighted differences between L3P and L5P, namely they have demonstrated that there is a dose-dependent effect observed for L3P on upregulation of CD25+ CD8 T cells from infected cows, while L5P effects were static. In contrast, L5P demonstrated a significantly stronger induction of CD25+ B cells from infected animals compared to L3P.

Methods:

PBMC Isolation and Stimulation for Flow Cytometry and Cytokine Measurements.

Peripheral blood mononuclear cells (PBMCs) were isolated from control non-infected (n=4) and cattle naturally infected with C-type Map (n=4) to determine if lipoproteins, L3P and L5P (structures disclosed in FIG. 9), can elicit immunological responses. Sixty ml of blood was collected via jugular venipuncture into a syringe containing 2× acid-citrate-dextrose to obtain PBMCs.

PBMCs were resuspended at a final concentration of 8×10$^6$/ml in complete medium consisting of RPMI-1640 with 2 mM 1-glutamine and 25 mM HEPES (Gibco, Grand Island, NY) and supplemented with 10% fetal calf serum (Gibco), 100λ penicillin-streptomycin (Gibco). Cells were plated in 24-well culture plates and incubated for 24 hr at 39° C. in 5% CO$_2$ in a humidified atmosphere with the following treatment groups, nonstimulated (NS; negative control), pokeweed mitogen (PWM, 10 μg/ml, positive control; Sigma, St. Louis, MO), and four antigens that included whole cell sonicated extracts of Map strains K-10 and S397 (10 μg/ml); lipoproteins L3P and L5P (1, 5, 10 μg/ml concentrations). The lipoproteins had to be solubilized in 100% methanol to 1 mg/ml concentrations and then diluted in the complete medium to final concentrations indicated above. This diluted solvent-lipopeptide mixture did not affect cell viability or response capabilities. After a 24-hr stimulation, the supernatants were harvested by centrifugation at 400×g for 5 min. Supernatants were removed without disturbing the cells in culture and stored at −20° C. until cytokine measurement. Cytokines IFN-γ, IL-1, IL-2, IL-4, IL-6 and TNF-α were all measured using Ciraplex bovine multiplex cytokine arrays (Aushon Biosystems, Billerica, MA).

For flow cytometry, PBMCs were cultured in replicate 48-well flat-bottom plates (Nunc Technologies, Rochester, NY) as described above with the same culture conditions and in vitro treatments. After incubating for either 3 days (NS, PWM) or 6 days (NS, antigens), cell populations were defined by labeling with 50 μl of a cocktail of primary antibodies to CD4, CD8, gamma delta T cell receptor (γδ TCR), and B cells, along with a CD25 activation marker (Washington State University Monoclonal Antibody Center, Pullman, WA). After a 15-min incubation at room temperature (RT), plates were centrifuged for 2 min at 400×g, the supernatant was decanted, and 50 μl of a secondary antibody cocktail was added, which included APC/Cy7 anti-mouse IgG2a (Southern Biotech, Birmingham, AL), AF350 anti-mouse IgG2b (Invitrogen, Waltham, MA), and BUV395 anti-mouse IgG3 (BDBiosciences, San Diego, CA). Live/

Dead populations were separated using Zombie Yellow™ Fixable Viability Dye (Biolegend, San Diego, CA). Cells were analyzed on a BDBiosciences LSRII Cytometer using FACSDiva V8.0.1 software. Further analysis was done using FlowJo® v10.2 (FLOWJO, LLC) software.

Results:

After 24 hr culture, there was a dose-dependent proliferation of CD25+ CD8 T cells from infected cows stimulated with L3P. By contrast, L5P stimulated cells remained static over the range of lipopeptide concentrations (FIG. 15A). S397, S-type Map strain, which contains L3P, produced a slightly stronger response than K-10 strain, which has LSP, although this difference was not significant (data not shown). In contrast, effects of lipopeptides on CD25+ B cells were reversed as L5P promoted a significantly ($P<0.0002$) stronger response compared to L3P (FIG. 15B). No significant differences were observed between L3P and L5P in CD25+ CD4 or CD25+γδ T cell populations (data not shown). Both L3P and L5P elicited cytokine responses to IFN-γ, IL-1β and TNF-α with no significant differences between the L3P or L5P treatments (FIG. 16). However, significant differences were observed between infected and control cells ($P<0.0001$ for IFN-γ and IL-1β, $P<0.03$ for TNF-α; FIG. 16). Interestingly, a dose-dependent effect ($P<0.0006$) of L5P concentration was observed on TNF-α secretion by PBMCs. IL-4 and IL-6 were not detected following stimulation with either lipopeptide (data not shown).

In the present study, L5P preferentially resulted in the upregulation of activated B cells (CD25+B cells), a finding that correlates with previous studies demonstrating this lipopentapeptide produces strong humoral responses in cattle and sheep (Biet et al., 2008). In contrast, L3P more distinctly upregulated T cell proliferation (CD25+CD8 T cells) in a dose-dependent manner, suggesting more of a Th1 immune response to this cell wall component. These results suggest that genomic differences between L3P and L5P may translate to antigenic differences that present immunological diversity within the infected host.

BIBLIOGRAPHIC REFERENCES

Alonso-Hearn, M., T. M. et al, (2010). *Innate Immun* 16: 235-247.
Amonsin, A., L. L. et al, (2004). *J. Clin. Microbiol.* 42: 1694-1702.
Bannantine, J. P., et al, (2014). Genome announcements 2.
Bannantine, J. P. et al, (2012). *BMC Genomics* 13: 89.
Bernut, A., J. L. et al, (2014). *Proc. Natl. Acad. Sci. U.S.A.* 111: E943-952.
Biet, F. et al, (2008). *Vaccine* 26: 257-268.
Biet, F. et al, (2012). *BMC Microbiol* 12: 264.
Blankemeyer-Menge B. et al. Tetrahedron Letters (1990) 31, 1701]
Dohmann, K., B. et al, (2003). *J. Clin. Microbiol.* 41: 5215-5223.
Eckstein, T. M., S. et al, (2006). *J. Biol. Chem.* 281: 5209-5215.
Gaudelli, N. M., D. H. Long & C. A. Townsend, (2015). *Nature* 520: 383-387.
Ghosh, P., C. et al, (2012). *PLoS One* 7: e31947.
Gumber, S., D. L. et al, (2009). *Vet. Microbiol.* 133: 344-357.
Gumber, S. & R. J. Whittington, (2009). *Vet. Microbiol.* 136: 82-90.
Holbert, S., M. et al, (2015). *Res. Vet. Sci.* 102: 118-121.
Howard, S. T., E. et al, (2006). *Microbiology* 152: 1581-1590.
Janagama, H. K. et al, (2009). *Microbiology* 155: 3683-3690.
Jimenez-Dalmaroni, M. J. et al, (2015). *Innate Immun* 21: 175-193.
Kansal, R. G., R. Gomez-Flores & R. T. Mehta, (1998). *Microb. Pathog.* 25: 203-214.
Lefrancois, L. H. et al, (2013). *J. Bacteriol.* 195: 4844-4853.
Li, L., et al (2005). *Proc. Natl. Acad. Sci. U.S.A.* 102: 12344-12349.
Marsh, I., et al (1999). *Mol. Cell. Probes* 13: 115-126.
Marsh, I. B., et al (2006). *J. Bacteriol.* 188: 2290-2293.
Motiwala, A. S., et al (2006). *Infect. Immun.* 74: 6046-6056.
NAHMS, (2008) Johne's disease on U.S. dairies, 1991-2007. *USDA-APHIS-VS-CEAH* Fort Collins, CO. Center for Epidemiology and Animal Health: 1-4.
Ortalo-Magne, A. et al, (1996). *J. Bacteriol.* 178: 456-461.
Ripoll, F. et al, (2007). *BMC Genomics* 8: 114.
Riviere, M. et al, (1996). *Eur. J. Biochem.* 241: 682-690.
Rottig, M., et al, (2011). *Nucleic Acids Res.* 39: W362-367.
Semret, M. et al, (2006). *J. Clin. Microbiol.* 44: 881-887.
Sibley, J. A. et al, (2007). *J. Wildl. Dis.* 43: 775-779.
Southern, E. M., (1975). *J. Mol. Biol.* 98: 503-517.
Stevenson, K. et al, (2002). *J. Clin. Microbiol.* 40: 1798-1804.
Thibault, V. C. et al, (2008). *J. Clin. Microbiol.* 46: 4091-4094.
Turenne, C. Y. et al, (2006). *J. Clin. Microbiol.* 44: 433-440.
van Soolingen, D. et al, (1994). *Methods EnzymoL* 235: 196-205.
Verdier, J. et al (2013). *PLoS One* 8: e62780.
Walsh, C. T. et al, (2013). *Angewandte Chemie. International Ed.* In English 52: 7098-7124.
Wang, H. et al, (2014). *Proc. Natl. Acad. Sci. U.S.A.* 111: 9259-9264.
Whittington, R. J. et al, (2011). *J. Clin. Microbiol.* 49: 1822-1830.
Wright, E. L. et al, (1996). *J. Clin. Microbiol.* 34: 2475-2478.
Wu, C. W. et al, (2006). *J. Bacteriol.* 188: 711-723.

We claim:

1. A method for genetically discriminating between a *Mycobacterium avium* subsp. *paratuberculosis* (Map) C-type and S-type in a sample, comprising detecting a 6.3 kb deletion in the msp1 gene of Map S-type with respect to the msp1 gene of Map C-type.

2. The method according to claim 1, wherein the sample is a sample of blood, serum, faeces, milk, lymph nodes, gut biopsies or urine.

3. A method for genetically characterizing a tested bacterium as a *Mycobacterium avium* subsp. *paratuberculosis* (Map) S-type or for detecting the presence of Map S-strain in a sample, comprising:
a) amplifying the genomic DNA of the tested mycobacterium with the following primers:

```
forward primer P1
                                      (SEQ ID NO: 10)
GTGCAGTACGCCGACTACAC
and reverse primer P3
                                      (SEQ ID NO: 12)
ACCGGGAAAACAGCAGTG;
``` and
b) detecting an amplified product having a length comprised between 1000 and 1224 bases.

4. The method according to claim 3, wherein the amplified product has a length of about 1112 bases.

5. The method according to claim 3, wherein the amplification step is carried out by PCR.

6. The method according to claim 3, wherein the sample is a sample of blood, serum, faeces, milk, lymph nodes, gut biopsies or urine.

7. The method according to claim 4, wherein the sample is a sample of blood, serum, faeces, milk, lymph nodes, gut biopsies or urine.

8. The method according to claim 5, wherein the sample is a sample of blood, serum, faeces, milk, lymph nodes, gut biopsies or urine.

9. A method for genetically discriminating between a *Mycobacterium avium* subsp. *paratuberculosis* (Map) C-type and S-type, comprising:
a) amplifying the genomic DNA of a mycobacterium with the following primers:

```
forward primer P1
                                      (SEQ ID NO: 10)
GTGCAGTACGCCGACTACAC, reverse primer P2:
                                      (SEQ ID NO: 11)
AGAAACCGATCAGCTCGTCG,
and reverse primer P3
                                      (SEQ ID NO : 12)
ACCGGGAAAACAGCAGTG;
``` and
b) detecting an amplified product;
wherein an amplified product of a length comprised between 320 and 392 is indicative of C-type and an amplified product of a length comprised between 1000 and 1224 bases is indicative of S-type.

10. The method according to claim 6, wherein the amplified product indicative of S-type has a length of about 1112 bases.

11. The method according to claim 6, wherein the amplified product indicative of C-type has a length of about 356 bases.

12. The method according to claim 9, wherein the amplification step is carried out by PCR.

13. The method according to claim 10, wherein the amplification step is carried out by PCR.

14. The method according to claim 11, wherein the amplification step is carried out by PCR.

* * * * *

SEQUENCE LISTING

```
Sequence total quantity: 46
SEQ ID NO: 1          moltype =    length =
SEQUENCE: 1
000

SEQ ID NO: 2          moltype =    length =
SEQUENCE: 2
000

SEQ ID NO: 3          moltype =    length =
```

```
SEQUENCE: 3
000

SEQ ID NO: 4            moltype =    length =
SEQUENCE: 4
000

SEQ ID NO: 5            moltype =    length =
SEQUENCE: 5
000

SEQ ID NO: 6            moltype =    length =
SEQUENCE: 6
000

SEQ ID NO: 7            moltype =    length =
SEQUENCE: 7
000

SEQ ID NO: 8            moltype =    length =
SEQUENCE: 8
000

SEQ ID NO: 9            moltype =    length =
SEQUENCE: 9
000

SEQ ID NO: 10           moltype = DNA  length = 20
FEATURE                 Location/Qualifiers
misc_feature            1..20
                        note = Primer
source                  1..20
                        mol_type = other DNA
                        organism = synthetic construct
SEQUENCE: 10
gtgcagtacg ccgactacac                                              20

SEQ ID NO: 11           moltype = DNA  length = 20
FEATURE                 Location/Qualifiers
misc_feature            1..20
                        note = primer
source                  1..20
                        mol_type = other DNA
                        organism = synthetic construct
SEQUENCE: 11
agaaaccgat cagctcgtcg                                              20

SEQ ID NO: 12           moltype = DNA  length = 18
FEATURE                 Location/Qualifiers
misc_feature            1..18
                        note = primer
source                  1..18
                        mol_type = other DNA
                        organism = synthetic construct
SEQUENCE: 12
accgggaaaa cagcagtg                                                18

SEQ ID NO: 13           moltype = AA  length = 5
FEATURE                 Location/Qualifiers
REGION                  1..5
                        note = synthetic peptide
source                  1..5
                        mol_type = protein
                        organism = synthetic construct
SEQUENCE: 13
FVIFA                                                              5

SEQ ID NO: 14           moltype = AA  length = 5
FEATURE                 Location/Qualifiers
REGION                  1..5
                        note = synthetic peptide
SITE                    1
                        note = MISC_FEATURE - D-phenylalanine
SITE                    2
                        note = MISC_FEATURE - N-methylation
SITE                    5
                        note = MISC_FEATURE - O-methylation
source                  1..5
                        mol_type = protein
```

```
                        organism = synthetic construct
SEQUENCE: 14
FVIFA                                                                    5

SEQ ID NO: 15           moltype = AA  length = 5
FEATURE                 Location/Qualifiers
REGION                  1..5
                        note = Synthetic peptide
SITE                    1
                        note = MISC_FEATURE - D-phenylalanine
SITE                    2
                        note = MISC_FEATURE - N-methylation
SITE                    5
                        note = MISC_FEATURE - amidation of the C-terminus
source                  1..5
                        mol_type = protein
                        organism = synthetic construct
SEQUENCE: 15
FVIFA                                                                    5

SEQ ID NO: 16           moltype = AA  length = 4274
FEATURE                 Location/Qualifiers
source                  1..4274
                        mol_type = protein
                        organism = Mycobacterium avium
SEQUENCE: 16
MKRGDRAYPV TRGQLDIWLA EQTGHLDVAW QLGVLVRIDG AIDPALLHQT MRHVVGEAES          60
LRASFFEADG QVFQKAVEYS DVDLTFYDLS GSSDPEREVR EMTASIQRTP MPLTGPMIKF         120
ALFRTGSAEY YWFTTCHHIA IDGMGIALVG RRIAAVYTAL ASGKPIPPAF FGSLQDLVGG         180
ELEYEASAKF LEDKDYWLAH RPGDGTAGHP PRPADDGRDP YSPSPPVQLD ESVIGSVKEL         240
SKALGIRRSS VLTAACALLV RGWCADGSDE VVLDFPVSRR VDPKSKTHPG MLAGVVPLVL         300
HAPAAATFAD FCRHVDQRSR EALRHQQFPT RTLDGEGDFS GPRQAPNRVV VNFVPARLTL         360
SLADVPATAT YTSFGPVGHF GLFFLGFGDQ QFLSTVGTGQ PLANFDATDL AERLQRILAA         420
MAADPARLLS SLDVLRDPEH AQLEALGNTA VLTRTPGPAV SVPELFATQV ARAPQDVALV         480
CEGRSLTYRQ LDEASNRLAH LLAGLGAGPG QSVALLFSRS AEAVASILAV LKTGAAYLPI         540
DPAAPETRIG FMLADAKPVA ALSTAELAGR LEGHGMTVID VNDPRIQDRP ATALPVPAAD         600
GVAYIYTSG TTGVPKGVAV THRNVTQLLG SLDAGLPPAG VWSQCHSYAF DVSVWEIFGA          660
LLRGGRLVVV PEDVTRAPEE LHDVLVNEQV SVLTQTPSAV AMLSPQGLES VSLVVVGEAC         720
PAEVVDRWSP GRVMVNAYGP TETTMCVAIS APLAPGMGSP PIGVPDGAG LFVLDAWLRP          780
VPPGVVGELY VGGAGVACGY WRRGGLTASW FVACPFGAPG ARMYRTGDLV CWRSDGQLDY         840
RGRADEQVKV RGYRIELGEV QAALAALDDV DQAVVIARED RPGGKRLVGY ITGTADPAEV         900
RTALAQRLPV YMVPAAVVAL DAIPLTPNGK LDTRALPTEA YTGSRYRAPS NAVEETVAGI         960
YAHVLGVERV GVDDSFFDLG GDSISALQVV ARARAAGLTC RPRDVFVEQT VARLARVVGS        1020
GDRAAEVADE GVGPVPPTPI MRWLQAAERA GGATDQFNQT VLVQAPAGVT ETEVAIVLQA        1080
LVDRHAMLRL RVTDDGADGW SFEVPEAGSV QARDCLRSVD ALSDEALLAA RARLNPAAGT        1140
MLAALWVEAT GQLAVIIHHL AVDAVSWWIL LEDLNIAWAL HRAGQPVELA PAGTSFARWA        1200
RLLDEHARDP EVVGQLDRWK TVTSTPAALP APRPDVDTYA SAGRLSVELD AETTAMLLGE        1260
VPAAFHAGIH DILLIAFGLA WTEFLGEPGA PIGIDVEGHG RHEELGADID LSRTVGWFTA        1320
KYPVSLDVAG LRWPQVAAGD PALGPVLKRA KEQLRTLPEP LTYGLLRYLN TDVDLAGADP        1380
PIAFNYLGRQ GAASDSAADG WRISQDMSLL GAAAAVPMPL MHAVELNAGT IDTGAGPHLH        1440
AEWTWAPSVL GAEQITRVSR LWFEALAGVC AHVRSGGGGG LTPSDIAPAR LTQQQIDELQ        1500
SRHRIADILP LTPLQQGLLF HSSTAQGNDG MDDMYAVQLD FTLTGPLDAD RLREAVRTVV        1560
HRHPHLAALF CDQYDEPVQI IPADPAVEWR YVELDGTGAA DADDLIEQLC AAERAAVADL        1620
AGQPVFRTAL VRTGGDRHRF VLTSHHILLD GWSLPILLRE IFAGYYGQRL PAAGSYRAFL        1680
TWLAERDLDA ARRAWGEVLS GFDTPTLVAP EGRLGQGRRV FEKSCVPEQT TRALGELARS        1740
CHTTLSTVLQ AAWAVVLTSL TGRHDVVFGT PRSRVGQLEV DDAEQMVGLL INTVPVRAEI        1800
TATTTTAQLL AQLQNSHNDT LEHQHLALNE IHRVTGHDQL FDTLFVYENY PIDSGMTLGA        1860
DGLAIAEFTN REYNHYPLTV EALPGPELGL HIEFDTDVFD TASIESLVQR LQRVLVAMST        1920
DPDRRLSSLD LLDRGERELV LSTMSGAGVS APIGVAPQLL AAVAADPDA PAIVDGAREL         1980
SYRELDDWST RLARKLIQHG VGPEHAAGVA IERCAELVVA WWAVTKVGGV YAPVNLDHPV        2040
ERIASVLDTV NAVCVLTCGT DEVAGAGPRP ILRIDGLDLS GHSTEPITDA DRRSPLRADD        2100
TAYLIFTSGS TGVPKGVAVS HTGLLGWAAA QRELFGLGAD ARVLMVASPT FDASVGELLL        2160
AAGSGAALIV APPQVYAGEA LTALLHNQRV GTAILTPTVI STLDRGRLDG LHTLVAVGEA        2220
CLPELVDGWA PGRQMFNGYG PSETTIWVTC ARLTAGHPVR IGAPIPGVCA RVLDGWLKPV        2280
PVGVVGELYL SGPALGHGYL GRVDLTAERF VANPFGGPGE RMYRTGDLVR WTPEGTLDYL        2340
GRADNQIKLR GQRIELGEIE NTLLACPQVT QAAVTVQDSA AGSQLVAYVT LDHGPSDADV        2400
RHDTDDADDV AQWRHLYDDL YGADLAATFG EDFRGWNSSY TGEPIPLQEM AEWRSATVDR        2460
IMSLRPRRVL EIGAGSGLLL SQIAPRCDRY VATDFSAVAI DNLARSMEQL QLPWRDRVEL        2520
LTQPAHVTDG LPPGHFDTIV INSVVQYFPN AGYLADVIDN ALELLAPGGS LFIGDVRNHA        2580
LQGAFQTGIA LARGGGADAA EIRQRVRHAM LGETELLLAP EFFTNWADSR PAAAGLDIQL        2640
KRGLSDNELN RYRYDVVIHK APAPVRSVAA APTWSWTDCT DCAGLRDQLA ARRPAVVRVT        2700
DIPQAGVIDD VRVEAALAAG LPVADALAAA GSDTAAAVAE ELHRVGEATG YRVAVTWGAQ        2760
PGTLSAVFVQ DGDQAAEPLT DLYLPPAGAR QRTRHANDPR ANTKIAQVRE RLNAWLPEYM        2820
VPTHIVALDE FPMTTSGKLD RKALPAPDYQ DADRYRAPST AVEEILVGIY GQVLGLERVG        2880
VDDSFFDLGG DSLSMRLIA AVNASLNTDL GVRTVFEAPT AAELALRVGS EADRPEPLVA         2940
GERPAVIPLS FAQTRLWFID QFQGSPSMYN ITVALRLSGR LDADALRAAL ADVVARHESL        3000
RTVFATADGT PQQVVIPADR IGFACDVVDA RGWPEDRLRE AMSAAARYTF DLSAESPLHT        3060
ELFARGDDEH VLVVAVHHIA ADGWSITPFA RDLGVAYASR CAGRDPDWAP LPVQYADYTL        3120
WQRAHLGVDD DPGSRIAAQL DFWTDALAGL PERLQLPTDR PYPAVADHRG ARLAVDWPAE        3180
```

```
LQQRIGDVAH RHNATSFMVI QTALTVLLAK LGANPDVAVG FPIAGRRDPA LDDLVGFFVN   3240
TLVLRVDAAG DPSFTELLAR VRTRSLEAFE HQDVPFEVLV ERLNPTRSLT HHPLVQVMLA   3300
WQNFAGDDTG PAAGLSLGDV EITPIPVDTH TARMDLTFSV GERWCESGEP GGIGGTVEFR   3360
TDVFDPDSIQ TLIGRLRRVL EAMTDDPTQS VWSVDLLDAG EHARLDTLGN RAALTGPPPR   3420
FDSLPTLFAE QAARTPDAVA LVCGGRRMTY RELDEAANRV AHLLRVRGAG PGHTVALLFS   3480
RSAEAIVAIL GVLKSGAAYL PIDPALPGER IGFMLADAAP MVAISTAELA PRLHGQHDVP   3540
VIDVHDPAIE AAPSSALPPP GADDIAYLIY TSGTTGVPKG VAVSHRNVTQ LLTADSGLPR   3600
EGVWSQWHSL AFDVSVWEIF GALLHGGRLV VIPDSVVRSP DDFHALLLDE QVSVLSQTPS   3660
AAGTLSPEGL EDLTLVVAGE ACPAELVDRW APGRTMINAY GPTEATVYTA ISAPLQPGSP   3720
AGVPIGFPVP GAGLFVLDES LRPVPPGVVG ELYVGGAGVA CGYWRRGGLT ASWFVACPFG   3780
APGARMYRTG DLVCWRSDGQ LDYRGRADEQ VKVRGYRIEL GEVQAALAGL DDVEQAVVIA   3840
REDRPGGKRL VGYITGTADP AEVRTALAQR LPVYMVPAAV VALDAIPLTP NGKLDTRALP   3900
TPEYTGSRYR APSNAVEETV AGIYAHVLGV ERVGVDDSFF DLGGDSISAM RVITAINASL   3960
GVELAVRTLF EAPTVASLSW RAQTDTARGG QAEEIVPVQT LKEGTGAPLF CIHAAGGLSW   4020
SYQVLGNHLD CPIIGIQQAE PQHAAPRSIR EMAQSYADRI QETYPDGPYH LVGWSFGGVV   4080
AHELAIELQR RGCAIARLVL LDAQPGLDGS VTAPDAALAE QHMMEEALRS HLAAADHDQP   4140
HAHRQFNQLV REAGAEGMSR HKRLFDVLFG NARNNIERSK IHEPGVFLGD VTIFSAVRDH   4200
EDRSAFLAEN WRPYVAGDIV IHEIDCTHDE ILNADVVDSY GQRLGQLLGA QRRRELTPPQ   4260
RFGADPGDDE PPVR                                                    4274

SEQ ID NO: 17          moltype = AA  length = 4273
FEATURE                Location/Qualifiers
source                 1..4273
                       mol_type = protein
                       organism = Mycobacterium avium
SEQUENCE: 17
VKRGDRAYPV TRGQLDIWLA EQTGHLDVAW QLGVLVRIDG AIDPALLHQT MRHVVGEAES   60
LRASFFEADG QVFQKAVEYS DVDLTFYDLS GSSDPEREVR EMTASIQRTP MPLTGPMTKF   120
ALFRTGSAEY YWFTTCHHIA IDGMGIALVG RRIAAVYTAL ASGKPIPPAF FGSLQDLVGG   180
ELEYEASAKF LEDKDYWLAH RPGDGTAGHP PRPADDGRDP YSPSPPVQLD ESVIGSVKEL   240
SKALGIRRSS VLTAACALLV RGWCADGSDE VVLDFPVSRR VDPKSKTHPG MLAGVVPLVL   300
HAPAAATFAD FCRHVDQRSR EALRHQQFPT RTLDGEGDFS GPRQAPNRVV VNFVPARLTL   360
SLADVPATAT YTSFGPVGHF GLFFLGFGDQ QFLSTVGTGQ PLANFDATDL AERLQRILAA   420
MAADPARLLS SLDVLRDPEH AQLEALGNTA VLTRTPGPAV SVPELFATQV ARAPQDVALV   480
CEGRSLTYRQ LDEASNRLAH LLAGLGAGPG QSVALLFSRS AEAIVAILGV LKSGAAYLPI   540
DPALPGERIG FMLADAAPMV AISTAELAPR LHGQHDPVI DVHDPAIEAA PSSALPPPGA   600
DDIAYLIYTS GTTGVPKGVA VSHRNVTQLL TADSGLPREG VWSQWHSLAF DVSVWEIFGA   660
LLHGGRLVVI PDSVVRSPDD FHALLLDEQV SVLSQTPSAA GTLSPEGLED LTLVVAGEAC   720
PAELVDRWAP GRTMINAYGP TETTMCVAIS APLAPGMGSP PIGVPVDGAG LFVLDAWLRP   780
VPPGVVGELY VAGAGVACGY WRRGGLTASR FVACPFGAPG ARMYRTGDLV CWRSDGQLDY   840
RGRADEQVKV RGYRIELGEV QAALAALDDV DQAVVIARED RPGGKRLVGY ITGTADPAEV   900
RTALAQRLPV YMVPAAVVAL DAIPLTPNGK LDTRALPTNG EYRAPE SPTEEILAGI   960
YAEVLGVERV GVDESFFDLG GDSISAMRVV ARARAAGLTC RPRDVFVEQT VARLARVVGS   1020
GDRAAEVADE GVGPVPPTPI MRWLQAAERA GGATDQFNQT VLVQAPAGVT ETEVAIVLQA   1080
LVDRHAMLRL RVTDDGADGW SFEVPEAGSV QARDCLRSVD ALSDEALLAA RARLNPAAGT   1140
MLAALWVEAT GQLAVIIHHL AVDAVSWWIL LEDLNIAWAL HRAGQPVELA PAGTSFARWA   1200
RLLDEHARDP EVVGQLRWK TVTSTPAALP APRPDVDTYA SAGRLSVELD AETTAMLLGE   1260
VPAAFHAGIH DILLIAFGLA WTEFLGEPGA PIGIDVEGHG RHEELGADID LSRTVGWFTA   1320
KYPVSLDVAG LRWPQVAAGD PALGPVLKRA KEQLRTLPEP LTYGLLRYLN TDVDLAGADP   1380
PIAFNYLGRQ GAASDSAADG WRISQDMSLL GAAAAVPMPL MHAVELNAGT IDTGAGPHLH   1440
AEWTWAPSVL GAEQITRVSR LWFEALAGVC AHVRSGGGGL TPSDIAPARL TQQQIDELQS   1500
RHRIADILPL TPLQQGLLFH SSTAQGNDGM DDMYAVQLDF TLTGPLDADR LREAVRTVVH   1560
RHPHLAALFC DQYDEPVQII PADPAVEWRY VELDGTGAAD ADDLIEQLCA AERAAVADLA   1620
GQPVFRTALV RTGGDRHRFV LTSSHILLDG WSLPILLREI FAGYYGQRLP AAGSYRAFLT   1680
WLAERDLDAA RRAWGEVLSG FDTPTLVAPE GRLGQGRRGF EKSCVPEQTT RALGELARSC   1740
HTTLSTVLQA AWAVVLTSLT GRHDVVFGTP RSRVGQLEVD DAEQMVGLLI NAVPVRAEIT   1800
ATTTTAQLLA QLQNSHNDTL EHQHLALNEI HRVTGHDQLF DTLFVYENYP IDSGMTLGAD   1860
GLAIAEFTNR EYNHYPLTVE ALPGPELGLH IEFDTDVFDT ASIESLVQRL QRVLAMSTD   1920
PDRRLSSLDL LDRGERELVL STMSGAGVSA PIGVAPQLLA AAVAADPDAP AIVDGARELS   1980
YRELDDWSTR LARKLIQHGV GPEHAAGVAI ERCAELVVAW WAVTKAGGVY APVNLDYPVE   2040
RIASVLDTVN AVCVLTCGTD EVAGAGPRPI LRIDGLDLSG HSTEPITDAD RRSPLRADDT   2100
AYLIFTSGST GVPKGVAVSH TGLLGWAAAQ RELFGLGADA RVLMVASPTF DASVGELLLA   2160
AGSGAALIVA PPQVYAGEAL TALLHNQRVG TAILTPTVIS TLDRGRLDGL HTLVAVGEAC   2220
LPELVDGWAP GRQMFNGYGP SETTIWVTCA RLTAGHPVRI GAPIPGVCAR VLDGWLKPVP   2280
VGVVGELYLS GPALGHGYLG RVDLTAERFV ANPFGGPGER MYRTGDLVRW TPEGTLDYLG   2340
RADNQIKLRG QRIELGEIEN TLLACPQVTQ AAVTVQDSAA GSQLVAYVTL DHGPSDADVR   2400
HDTDDADDVA QWRHLYDDLY GADLAATFGE DFRGWNSSYT GEPIPLQEMA EWRSATVDRI   2460
MSLRPRRVLE IGAGSGLLLS QIAPRCDRYV ATDFSAVAID NLARSMEQLQ LPWRDRVELL   2520
TQPAHVTDGL PPGHFDTIVI NSVVQYFPNA GYLADVIDNA LELLAPGGSL FIGDVRNHAL   2580
QGAFQTGIAL ARGGADAAE IRQRVRHAML GETELLLAPE FFTNWADSRP AAAGLDIQLK   2640
RGLSDNELNR YRYDVVIHKA PAPVRSVAAA PTWSWTDCTD CAGLRDQLAA RRPAVVRVTD   2700
IPQAGVIDDV RVEAALAAGL PVADALAAAG SDTAAVAEE LHRVGEATGY RVAVTWGAQP   2760
GTLSAVFVQD GDQAAEPLTD LYLPPAGARQ RTRHANDPRA NTKIAQVRER LNAWLPEYMV   2820
PTHIVALDEF PMTTSGKLDR KALPADPDYQ ADRYRAPSTA VEEILVGIYG QVLGLERVGV   2880
DDSFFDLGGD SLSAMRLIAA VNASLNTDLG VRTVFEAPTA AELALRVGSE ADRPEPLVAG   2940
ERPAVIPLSF AQTRLWFIDQ FQGPSPMYNI TVALRLSGRL DADALRAALA DVVARHESLR   3000
TVFATADATP QQVVIPADRI GFACDVVDAR GWPEDRLREA MSAAARYTFD LSAESPLHTE   3060
LFARGDDEHV LVVAVHHIAA DGWSITPFAR DLGVAYASRC AGRDPDWAPL PVQYADYTLW   3120
QRAHLGDVDD PGSRIAAQLD FWTDALAGLP ERLQLPTDRP YPAVADHRGA RLAVDWPAEL   3180
```

```
QQRIGDVAHR HDATSFMVIQ TALTVLLAKL GANPDVAVGF PIAGRRDPAL DDLVGFFVNT    3240
LVLRVDAAGD PSFTELLARV RTRSLEAFEH QDVPFEVLVE RLNPTRSLTH HPLVQVMLAW    3300
QNFAGQDTGP AAGLSLGDVE ITPIPVDTHT ARMDLTFSVG ERWCESGEPG GIGGTVEFRT    3360
DVFDPDSIQT LIGRLRRVLE AMTDDPTQSV WSVDLLDAGE HARLDTLGNR AALTGPPPRF    3420
DSLPTLFAEQ AARTPDAVAL VCGGRRMTYR ELDEASNRLA HLLAGLGAGP GQSVALLFSR    3480
SAEAIVAILG VLKSGAAYLP IDPALPGERI GFMLADAAPM VAISTAELAP RLHGQHDVPV    3540
IDVHDPAIEA APSSALPPPG ADDIAYLIYT SGTTGVPKGV AVSHRNVTQL LTADSGLPRE    3600
GVWSQWHSLA FDVSVWEIFG ALLHGGRLVV IPDSVVRSPD DFHALLLDEQ VSVLSQTPSA    3660
AGTLSPEGLE DLTLVVAGEA CPAELVDRWA PGRTMINAYG PTEATVYTAI SAPLQPGSPA    3720
GVPIGFPVPG AGLFVLDESL RPVPPGVVGE LYVAGAGVAC GYWRRGGLTA SRFVACPFGA    3780
PGARMYRTGD LVCWRSDGQL DYRGRADEQV KVRGYRIELG EVQAALAALD DVDQAVVIAR    3840
EDRPGGKRLV GYITGTADPA EVRTALAQRL PVYMVPAAVV ALDAIPLTPN GKLDTRALPT    3900
PEYTGSRYRA PSNAVEETVA GIYAHVLGVE RVGVDDSFFD LGGDSISAMR VITAINASLG    3960
VELAVRTLFE APTVASLSWR AQTDTARGGQ AEEIVPVQTL KEGTGAPLFC IHAAGGLSWS    4020
YQVLGNHLDC PIIGIQQAEP QHAAPRSIRE MAQSYADRIQ ETYPDGPYHL VGWSFGGVVA    4080
HELAIELQRR GCAIARLVLL DAQPGLDGSV TAPDAALAEQ HMMEEALRSH LAAADHDQPH    4140
AHRQFNQLVR EAGAEGMSRH KRLFDVLFGN ARNNIERSKI HEPGVFLGDV TIFSAVRDHE    4200
DRSAFLAENW RPYVAGDIVI HEIDCTHDEI LNADVVDSYG QRLGQLLGAQ RRRELTPPQR    4260
FGADPGDDEP PVR                                                     4273

SEQ ID NO: 18           moltype = DNA   length = 21
FEATURE                 Location/Qualifiers
misc_feature            1..21
                        note = primer
source                  1..21
                        mol_type = other DNA
                        organism = synthetic construct
SEQUENCE: 18
cttgagcagc tcgtaaagcg t                                                    21

SEQ ID NO: 19           moltype = DNA   length = 25
FEATURE                 Location/Qualifiers
misc_feature            1..25
                        note = primer
source                  1..25
                        mol_type = other DNA
                        organism = synthetic construct
SEQUENCE: 19
gctgtatgag gaagtctatt catgg                                                25

SEQ ID NO: 20           moltype = DNA   length = 22
FEATURE                 Location/Qualifiers
misc_feature            1..22
                        note = primer
source                  1..22
                        mol_type = other DNA
                        organism = synthetic construct
SEQUENCE: 20
aacgagagga agaactaagc cg                                                   22

SEQ ID NO: 21           moltype = DNA   length = 24
FEATURE                 Location/Qualifiers
misc_feature            1..24
                        note = primer
source                  1..24
                        mol_type = other DNA
                        organism = synthetic construct
SEQUENCE: 21
ttacggagca ggaaggccag cggg                                                 24

SEQ ID NO: 22           moltype = DNA   length = 18
FEATURE                 Location/Qualifiers
misc_feature            1..18
                        note = primer
source                  1..18
                        mol_type = other DNA
                        organism = synthetic construct
SEQUENCE: 22
gtcaagggat cggcgagg                                                        18

SEQ ID NO: 23           moltype = DNA   length = 19
FEATURE                 Location/Qualifiers
misc_feature            1..19
                        note = primer
source                  1..19
                        mol_type = other DNA
                        organism = synthetic construct
SEQUENCE: 23
tggacttgag cacggtcat                                                       19
```

```
SEQ ID NO: 24           moltype = DNA  length = 20
FEATURE                 Location/Qualifiers
misc_feature            1..20
                        note = primer
source                  1..20
                        mol_type = other DNA
                        organism = synthetic construct
SEQUENCE: 24
cgttgcgatt tctgcgtagc                                                    20

SEQ ID NO: 25           moltype = DNA  length = 20
FEATURE                 Location/Qualifiers
misc_feature            1..20
                        note = primer
source                  1..20
                        mol_type = other DNA
                        organism = synthetic construct
SEQUENCE: 25
ggtgatggtc gtggtcatcc                                                    20

SEQ ID NO: 26           moltype = DNA  length = 20
FEATURE                 Location/Qualifiers
misc_feature            1..20
                        note = primer
source                  1..20
                        mol_type = other DNA
                        organism = synthetic construct
SEQUENCE: 26
catatctggc atggctccag                                                    20

SEQ ID NO: 27           moltype = DNA  length = 22
FEATURE                 Location/Qualifiers
misc_feature            1..22
                        note = primer
source                  1..22
                        mol_type = other DNA
                        organism = synthetic construct
SEQUENCE: 27
atcgtgttga ccccaaagaa at                                                 22

SEQ ID NO: 28           moltype = DNA  length = 20
FEATURE                 Location/Qualifiers
misc_feature            1..20
                        note = primer
source                  1..20
                        mol_type = other DNA
                        organism = synthetic construct
SEQUENCE: 28
acaacgaaac ctacctcgtc                                                    20

SEQ ID NO: 29           moltype = DNA  length = 18
FEATURE                 Location/Qualifiers
misc_feature            1..18
                        note = primer
source                  1..18
                        mol_type = other DNA
                        organism = synthetic construct
SEQUENCE: 29
gtgagctggc ggcctaac                                                      18

SEQ ID NO: 30           moltype = DNA  length = 18
FEATURE                 Location/Qualifiers
misc_feature            1..18
                        note = primer
source                  1..18
                        mol_type = other DNA
                        organism = synthetic construct
SEQUENCE: 30
gacgagcagc tgtccgag                                                      18

SEQ ID NO: 31           moltype = DNA  length = 18
FEATURE                 Location/Qualifiers
misc_feature            1..18
                        note = primer
source                  1..18
                        mol_type = other DNA
                        organism = synthetic construct
SEQUENCE: 31
```

```
gagagcgtgg ccatcgag                                                  18

SEQ ID NO: 32          moltype = DNA   length = 20
FEATURE                Location/Qualifiers
misc_feature           1..20
                       note = primer
source                 1..20
                       mol_type = other DNA
                       organism = synthetic construct
SEQUENCE: 32
ccacagggtt tttggtgaag                                                20

SEQ ID NO: 33          moltype = DNA   length = 20
FEATURE                Location/Qualifiers
misc_feature           1..20
                       note = primer
source                 1..20
                       mol_type = other DNA
                       organism = synthetic construct
SEQUENCE: 33
ggaaatccaa cagcaaggac                                                20

SEQ ID NO: 34          moltype = DNA   length = 22
FEATURE                Location/Qualifiers
misc_feature           1..22
                       note = primer
source                 1..22
                       mol_type = other DNA
                       organism = synthetic construct
SEQUENCE: 34
cgcggcgagc gggagctggt gc                                             22

SEQ ID NO: 35          moltype = DNA   length = 22
FEATURE                Location/Qualifiers
misc_feature           1..22
                       note = primer
source                 1..22
                       mol_type = other DNA
                       organism = synthetic construct
SEQUENCE: 35
cgcagcgggg agcgccggtc gg                                             22

SEQ ID NO: 36          moltype = DNA   length = 20
FEATURE                Location/Qualifiers
misc_feature           1..20
                       note = rpimer
source                 1..20
                       mol_type = other DNA
                       organism = synthetic construct
SEQUENCE: 36
ggcgttacag aattgccttg                                                20

SEQ ID NO: 37          moltype = DNA   length = 20
FEATURE                Location/Qualifiers
misc_feature           1..20
                       note = primer
source                 1..20
                       mol_type = other DNA
                       organism = synthetic construct
SEQUENCE: 37
gctcgaagtt ggagatcagg                                                20

SEQ ID NO: 38          moltype = DNA   length = 20
FEATURE                Location/Qualifiers
misc_feature           1..20
                       note = primer
source                 1..20
                       mol_type = other DNA
                       organism = synthetic construct
SEQUENCE: 38
gtacgtggtg accaatgtcg                                                20

SEQ ID NO: 39          moltype = DNA   length = 20
FEATURE                Location/Qualifiers
misc_feature           1..20
                       note = primer
source                 1..20
                       mol_type = other DNA
                       organism = synthetic construct
```

```
SEQUENCE: 39
tagaaggtgc gggaaagttg                                                    20

SEQ ID NO: 40           moltype = DNA  length = 20
FEATURE                 Location/Qualifiers
misc_feature            1..20
                        note = primer
source                  1..20
                        mol_type = other DNA
                        organism = synthetic construct
SEQUENCE: 40
gtctatctgg cggtgctctc                                                    20

SEQ ID NO: 41           moltype = DNA  length = 20
FEATURE                 Location/Qualifiers
misc_feature            1..20
                        note = primer
source                  1..20
                        mol_type = other DNA
                        organism = synthetic construct
SEQUENCE: 41
gtcgaagcag cgttgattgt                                                    20

SEQ ID NO: 42           moltype = DNA  length = 24
FEATURE                 Location/Qualifiers
misc_feature            1..24
                        note = primer
source                  1..24
                        mol_type = other DNA
                        organism = synthetic construct
SEQUENCE: 42
tgttcttcac cacccagggc cggg                                               24

SEQ ID NO: 43           moltype = DNA  length = 27
FEATURE                 Location/Qualifiers
misc_feature            1..27
                        note = primer
source                  1..27
                        mol_type = other DNA
                        organism = synthetic construct
SEQUENCE: 43
ttgagcgaca gcaggtagtc gtcggcg                                            27

SEQ ID NO: 44           moltype = DNA  length = 25
FEATURE                 Location/Qualifiers
misc_feature            1..25
                        note = primer
source                  1..25
                        mol_type = other DNA
                        organism = synthetic construct
SEQUENCE: 44
ttggtgcgcc gcaagagcgc aaccg                                              25

SEQ ID NO: 45           moltype = DNA  length = 23
FEATURE                 Location/Qualifiers
misc_feature            1..23
                        note = primer
source                  1..23
                        mol_type = other DNA
                        organism = synthetic construct
SEQUENCE: 45
atttcagctt gtacagcggt ggc                                                23

SEQ ID NO: 46           moltype = DNA  length = 18
FEATURE                 Location/Qualifiers
misc_feature            1..18
                        note = primer
source                  1..18
                        mol_type = other DNA
                        organism = synthetic construct
SEQUENCE: 46
gcagtacgcc gactacac                                                      18
```